(12) United States Patent
Wagner et al.

(10) Patent No.: US 8,257,931 B2
(45) Date of Patent: Sep. 4, 2012

(54) REGULATION OF PROTEIN SYNTHESIS

(75) Inventors: Gerhard Wagner, Chestnut Hill, MA (US); Michael Chorev, Chestnut Hill, MA (US); Nathan John Moerke, Brookline, MA (US); Bertal Huseyin Aktas, Newton, MA (US); José Halperin, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 655 days.

(21) Appl. No.: 11/795,078

(22) PCT Filed: Jan. 20, 2006

(86) PCT No.: PCT/US2006/002093
§ 371 (c)(1),
(2), (4) Date: Nov. 24, 2009

(87) PCT Pub. No.: WO2006/078942
PCT Pub. Date: Jul. 27, 2006

(65) Prior Publication Data
US 2010/0144805 A1 Jun. 10, 2010

Related U.S. Application Data

(60) Provisional application No. 60/646,219, filed on Jan. 21, 2005.

(51) Int. Cl.
C07D 277/20 (2006.01)
A61P 35/04 (2006.01)
G01N 33/53 (2006.01)
A61K 31/425 (2006.01)
C12Q 1/02 (2006.01)
C12N 5/02 (2006.01)

(52) U.S. Cl. .......... 435/7.1; 435/29; 435/375; 514/370; 548/194

(58) Field of Classification Search .................. None
See application file for complete search history.

(56) References Cited

FOREIGN PATENT DOCUMENTS

| JP | 2003-313168 A | 11/2003 |
|----|---------------|---------|
| WO | 2003/039451 A2 | 5/2003 |
| WO | 2005/007141 A2 | 1/2005 |

OTHER PUBLICATIONS

Moerke et al., Cell, 128 (2007), 257-267.*
Holla et al., caplus an 2003:236108.*
Examination Report relating to corresponding AU Application No. 2006206286.
Chen, et al., Synthesis and Biological Evaluation of Thiazolidine-2,4-Dione and 2,4-Thione Derivatives as Inhibitors of Translation Initiation Bioorganic & Medicinal Chemistry Letters 14 (2004) 5401-5405.
Chen, et al., Thiazolyl Hydrazones as Novel Inhibitors of EIF4E/EIF4G Interaction for Cancer Therapy, Abstract of Papers Am. Chem. Soc., 229(2):U196-U197 and 229th Nat. Mtg., Am. Chem. Soc., San Diego, CA (2005).
Fehrentz, et al., An Efficient Synthesis of Optically Active α-(t-Butoxy-carbonylamino)-aldehydes from α-Amino Acids, Synthesis 1983(8):676 (1983).
Ghosh, et al., Synthesis and Evaluation of Potential Inhibitors of eIF4E Cap Binding to 7-Methyl GTP, Bioorganic & Medicinal Chemistry Letters 15 (2005) 2177-2150.
Gutierrez, et al., TiCl(O'Pr)3 and NaBH(OAc)3: An Efficient Reagent Combination for the Reduction Amination of Aldehydes by Electron-Deficient Amines, Tetrahedron Letters 46 (2005) 3595-3597.
Haghighat, et al., eIF4G Dramatically Enhances the Binding of eIF4E to the mRNA 5'-Cap Structure, The Journal of Biological Chemistry, vol. 272, No. 35, Issue of Aug. 29, 21677-21680 (1997).
Kimball, et al., A Microtiter Plate Assay for Assessing the Interaction of Eukaryotic Initiation Factor eIF4E with eIF4G and eIF4E Binding Protein-1, Analytical Biochemistry 325 (2004) 364-368.
Natarajan, et al., Synthesis of Fluorescein Labeled 6-Methylguanosinemonophosphate, Bioorganic & Medicinal Chemistry Letters 14 (2004) 2657-2660.
Pozdnev, Activation of Carboxylic Acids by Pyrocarbonates. Application of DI-tert-BUTYLI Pyrocarbonate as Condensing Reagent In the Synthesis of Amides of Protected Amino Acids and Peptides, Tetrahedron Letters, vol. 36 No. 39 7115-7118 (1995).
Examination Report relating to corresponding CA Application No. 2,619,153.
Office Communication relating to corresponding EP Application No. 06719064.5.
Notice of Reasons for Rejection relating to corresponding JP Application No. 2007-552297, issued Mar. 7, 2012.
English Translation of Notice of Reasons for Rejection relating to corresponding JP Application No. 2007-552297, issued Mar. 7, 2012.
Hu, et al., "Identification of Selective Inhibitors for the Glycosyltransferase MurG via High-Throughput Sequencing," Chemistry & Biology, vol. 11, 703-711, May 2004. Examiner's Report relating to corresponding CA Application No. 2,619,153, issued Jan. 9, 2012.
Rousseau, et al., The eIF4E-binding Proteins 1 and 2 are Negative Regulators of Cell Growth, Oncogene (1996) 13, 2415-2420.
Avdulov, et al., Activation of Translation Complex eIF4F is Essential for the Genesis and Maintenance of the Malignant Phenotype in Human Mammary Epithelial Cells, Cancer Cell: Jun. 2004, vol. 553-563.
Turner, et al., Antihypertensive Thiadiazoles. 1. Synthesis for Some 2-Aryl-5-Hydrazino-1,3,4-Thiadiazoles with Vasodilator Activity, J. Med. Chem. 1988, 31, 902-906.
On the Anti-tumor Activity of Nitrogenous Cyclic β-Diketones, Chemical and Pharmaceutical Bulletin, vol. 8, No. 11, Nov. 1960.
Portoghese, Editorial—Medicinal Chemistry: 1989 and Beyond, J. Med. Chem., 1989, vol. 32, No. 1, 1 page.
Moerke, et al., Small-Molecule Inhibition of the Interaction Between the Translation Initiation Factors eIF4E and eIF4G, Cell 128, 257-267, Jan. 26, 2007.
English Abstract of JP2003313168 (A).
International Search Report and Written Opinion corresponding to PCT/US2006/002093.

* cited by examiner

*Primary Examiner* — Sun Jae Loewe
(74) *Attorney, Agent, or Firm* — Banner & Witcoff, Ltd.

(57) ABSTRACT

A composition and method for inhibiting proliferation of a tumor cell compared to a non-tumor cell. Also described are methods of screening for a composition that inhibits cap-dependent translation compared to cap-independent translation of proteins.

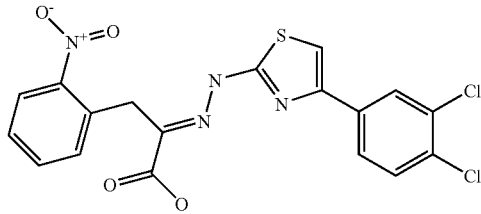

40 Claims, 37 Drawing Sheets

HITS FROM BIONET, PEAKDALE, AND
MAYBRIDGE LIBRARIES (16,000 SCREENED)

37629

21573

35197

21551

29578

| No. | R₁ = | IC₅₀(comp.)/IC₅₀(pept.) (FP) | GI₅₀(µM) HT29 | GI₅₀(µM) A549 | No. | R₁ = | IC₅₀(comp.)/IC₅₀(pept.) (FP) | GI₅₀(µM) HT29 | GI₅₀(µM) A549 |
|---|---|---|---|---|---|---|---|---|---|
| 4a | phenyl | >8 | 65 | 25 | 4f | biphenyl | 3 | <1 | 4 |
| 1 | 2,3-dichlorophenyl | 5.5 | 9 | 5 | 4g | 4-cyclohexylphenyl | 1.3 | 12 | 7 |
| 4c | naphthyl | 2.9 | 21 | 5 | 4h | 4-morpholinophenyl | >8 | 59 | 45 |
| 4d | benzodioxole | 2.3 | 9 | 14 | 4i | 4-pyrrolidinophenyl | >8 | 52 | >65 |
| 4e | benzodioxepine | 5.3 | 45 | 24 | 4j | 4-(phenyldiazenyl)phenyl | 2 | 3 | 37 |

```
                         SEQUENCE LISTING

<160> NUMBER OF SEQ ID NOS: 4

<210> SEQ ID NO 1
<211> LENGTH: 217
<212> TYPE: PRT
<213> ORGANISM: Homo sapiens

<400> SEQUENCE: 1

Met Ala Thr Val Glu Pro Glu Thr Thr Pro Thr Pro Asn Pro Pro Thr
1               5                   10                  15
```

```
Thr Glu Glu Glu Lys Thr Glu Ser Asn Gln Glu Val Ala Asn Pro Glu
            20                  25                  30

His Tyr Ile Lys His Pro Leu Gln Asn Arg Trp Ala Leu Trp Phe Phe
        35                  40                  45

Lys Asn Asp Lys Ser Lys Thr Trp Gln Ala Asn Leu Arg Leu Ile Ser
 50                  55                  60

Lys Phe Asp Thr Val Glu Asp Phe Trp Ala Leu Tyr Asn His Ile Gln
 65                  70                  75                  80

Leu Ser Ser Asn Leu Met Pro Gly Cys Asp Tyr Ser Leu Phe Lys Asp
                85                  90                  95

Gly Ile Glu Pro Met Trp Glu Asp Glu Lys Asn Lys Arg Gly Gly Arg
            100                 105                 110

Trp Leu Ile Thr Leu Asn Lys Gln Gln Arg Arg Ser Asp Leu Asp Arg
        115                 120                 125

Phe Trp Leu Glu Thr Leu Leu Cys Leu Ile Gly Glu Ser Phe Asp Asp
130                 135                 140

Tyr Ser Asp Asp Val Cys Gly Ala Val Val Asn Val Arg Ala Lys Gly
145                 150                 155                 160

Asp Lys Ile Ala Ile Trp Thr Thr Glu Cys Glu Asn Arg Glu Ala Val
                165                 170                 175

Thr His Ile Gly Arg Val Tyr Lys Glu Arg Leu Gly Leu Pro Pro Lys
            180                 185                 190

Ile Val Ile Gly Tyr Gln Ser His Ala Asp Thr Ala Thr Lys Ser Gly
        195                 200                 205

Ser Thr Thr Lys Asn Arg Phe Val Val
    210                 215

<210> SEQ ID NO 2
<211> LENGTH: 11
<212> TYPE: PRT
<213> ORGANISM: Artificial Sequence
<220> FEATURE:
<223> OTHER INFORMATION: eIF2-derived peptide made using standard
      synthesis methods

<400> SEQUENCE: 2

Lys Tyr Thr Tyr Asp Glu Leu Phe Gln Leu Lys
1               5                   10

<210> SEQ ID NO 3
<211> LENGTH: 17
<212> TYPE: PRT
<213> ORGANISM: Artificial Sequence
<220> FEATURE:
<223> OTHER INFORMATION: eIF2-derived peptide made using standard
      synthesis methods

<400> SEQUENCE: 3

Lys Lys Gln Tyr Asp Arg Glu Phe Leu Leu Asp Phe Gln Phe Met Pro
1               5                   10                  15

Ala

<210> SEQ ID NO 4
<211> LENGTH: 11
<212> TYPE: PRT
<213> ORGANISM: Artificial Sequence
<220> FEATURE:
<223> OTHER INFORMATION: eIF2-derived peptide made using standard
      synthesis methods

<400> SEQUENCE: 4
```

-continued

```
Lys Arg Tyr Asp Arg Glu Phe Leu Leu Gly Phe
1               5                   10
```

REGULATION OF PROTEIN SYNTHESIS

RELATED APPLICATIONS

This application is a national stage application, filed under 35 U.S.C. §371, of PCT/US2006/002093, filed on Jan. 20, 2006, which claims priority to USSN 60/646,219, filed on Jan. 21, 2005, each of which is herein incorporated by reference in its entirety.

STATEMENT AS TO FEDERALLY SPONSORED RESEARCH

This invention was funded in part by the U.S. Government under grant numbers U19-CA87427 and RO1-CA68262 awarded by the National Institutes of Health. The Government has certain rights in the invention.

BACKGROUND

The regulation of protein synthesis at the level of translation initiation plays a key role in the control of cell growth, proliferation, and apoptosis. The interaction between the initiation factors eIF4E and eIF4G is a major component of this process. eIF4E binds the 7-methylguanosine cap structure found at the 5' ends of most messenger RNAs. Its binding partner eIF4G, a scaffold protein, provides a docking site for other initiation factors, including the RNA helicase eIF4A. Collectively, eIF4E, eIF4G, and eIF4A forms a ternary complex referred to as eIF4F. Once assembled, this complex recruits the 40S ribosomal subunit to the 5' end of the mRNA molecule as a result of the interaction of eIF3 with eIF4G, followed by scanning of the 40S subunit to the initiation codon where it joins with the 60S subunit. This process is facilitated by eIF4A, with the requirement for its helicase activity being directly proportional to the amount of secondary structure in the 5' UTR that must be melted for scanning to occur.

Biosynthesis of many growth-promoting proteins is suppressed on the translation-initiation level, and several forms of cancer exhibit an out-of-balance translation initiation machinery. Although inhibitors of translation exist, most, if not all, act nonspecifically on all translation.

SUMMARY OF THE INVENTION

The invention features inhibitors of translation initiation that selectively suppress synthesis of growth factors and oncogene products. The invention includes a number of small molecule inhibitors of the protein-protein interaction between the eukaryotic translation initiation factors eIF4E and eIF4G. The molecular mass of the inhibitory compounds is 600 daltons or less, e.g., 500 daltons, 400 daltons, 300 daltons, 200 daltons, 100 daltons. Preferably, the inhibitor is not a peptide or proteinaceous in nature.

For example, compounds of the invention include those that modulate eIF4E/eIF4G interactions and have the formula

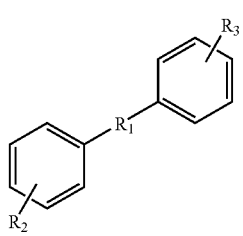

(I)

where $R_1$ is a hydrazone thiazole moiety of the structure

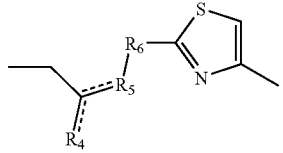

(II)

or a barbituric acid moiety (or derivative thereof) of the structure

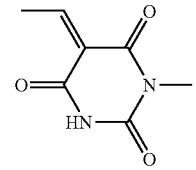

(III)

$R_2$ is hydrogen, hydroxyl, CN, $CF_3$, $CO_2H$, $SO_3H$, $PO_3H_2$, $SO_2R$, $SO_2NHR$, $SONH_2$, $CONH_2$, CONHR and NHCOR, or a nitro group present in one, two, or three locations on the ring to which it is attached; where R is an alkyl of 1-4 carbones or aryl.

$R_3$ is a group individually present in one, two, or three locations on the ring, wherein the group may be halo, CN, $CF_3$, $CO_2H$, $SO_3H$, $PO_3H_2$, $SO_2R$, $SO_2NHR$, $SONH_2$, —N═NR, $CONH_2$, CONHR and NHCOR, hydrogen, conjugated or unconjugated aryl or heteroaryl, a alicyclic, heterocyclic or polycyclic group, or $R_3$, taken with the ring to which it is attached, forms a conjugated ring structure, e.g., a naphthalene, benzodioxine or benzodioxepine ring; where R is lower alkyl, e.g., C1-C4, or aryl.

R4 is hydrogen, hydroxyl or lower hydroxyalkyl, carboxyl, a lower alkyl ester, e.g.,

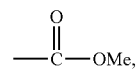

or oxygen (in which case the dotted bond is present, i.e., forming a carbonyl group); tetrazole, $SO_3H$, or $PO_3H_2$;

$R_5$ is N (in which case the dotted bond is present), NH, or carbonyl; and $R_6$ is NH or carbonyl.

In formula II, $R_4$ is desirably a carboxylate group or a pharmaceutically acceptable salt thereof; $R_5$ is desirably N; and $R_6$ is desirably NH. In embodiments, $R_5$ and $R_6$ may desirably respectively be carbonyl and $CH_2$; $CH_2$ and carbonyl; NH and $CH_2$; or $CH_2$ and NH.

Examples of compounds of the invention include the following:

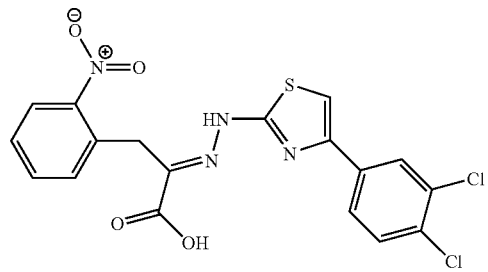

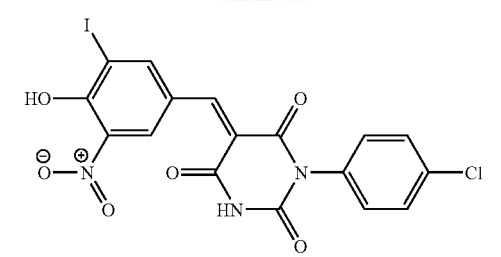
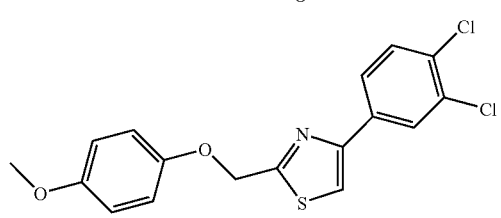
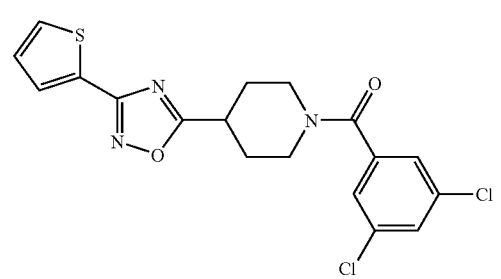
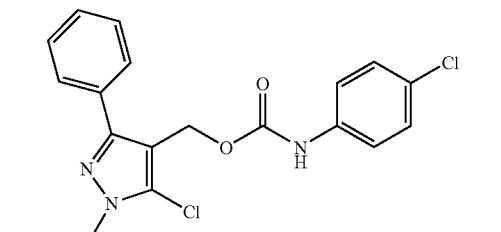
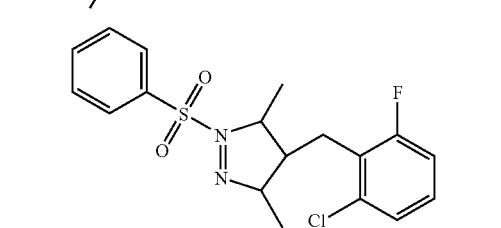
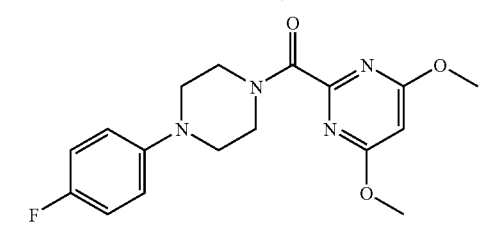
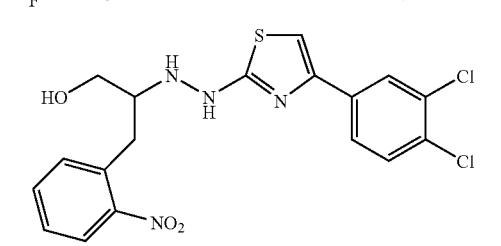
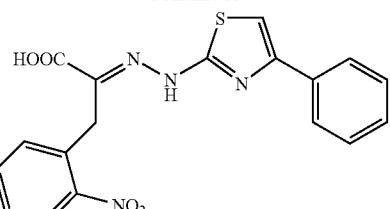
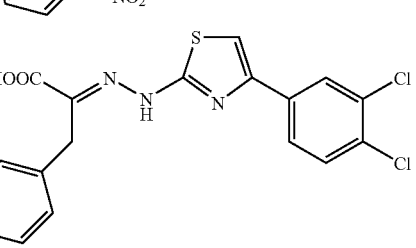
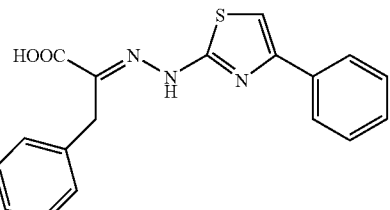
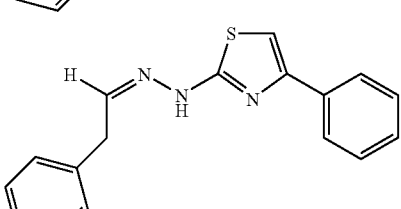
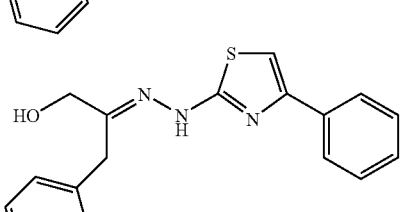
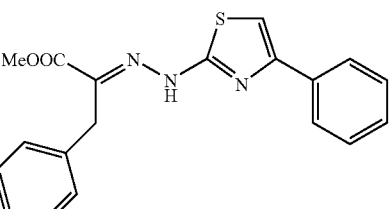
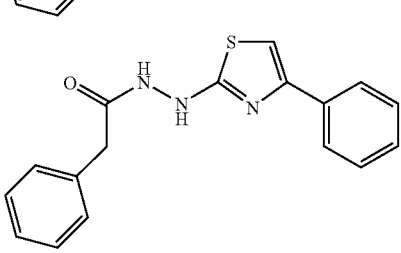

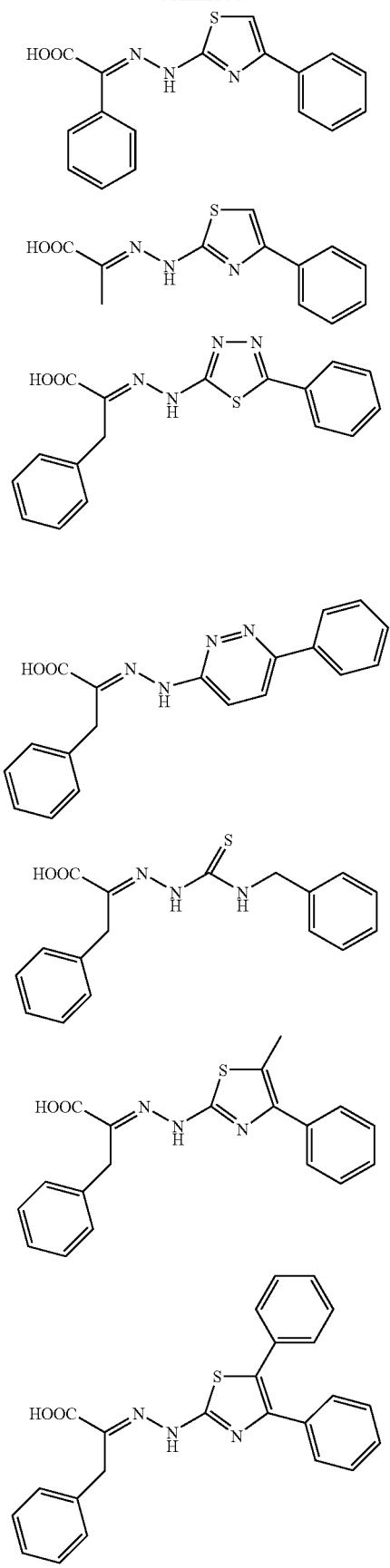

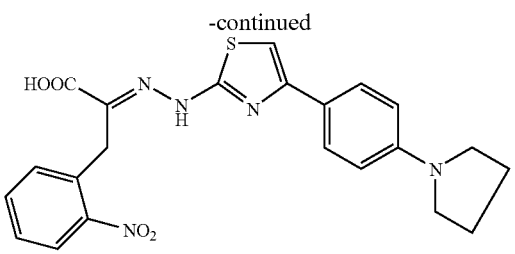

Desirably, the compound is EGI-1, referred herein as compound 154300, ICCB Compound 1, or ICCB-15644. The chemical structure of EGI-1 is shown below.

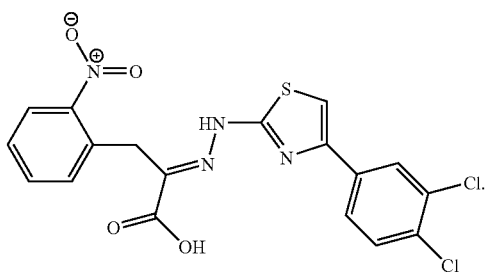

The present invention also features a method of inhibiting cap-dependent protein synthesis in a cell by contacting the cell with one or more of the compound described above. This inhibition in turn causes apoptosis, which results from the down-regulation of growth-promoting proteins as well as the up-regulation of apoptosis-promoting proteins and IRES-dependent proteins (e.g., Apaf-1, c-myc, XIAP, and DAP5). The compounds described herein bind a hydrophobic groove of eIF4E formed by the polypeptide segments 68-84 and 120-140 of human eIF4E (SEQ ID NO:1). The compounds inhibit the binding of eIF4G to eIF4E by blocking the eIF4G-binding site on eIF4E, displacing eIF4G from eIF4E by competitive binding or both. The different compounds investigated bind at slightly different but adjacent positions within the groove formed by segments 37-39, 68-84, and 120-140. EGI-1 (Compound 154300) for example binds near residues L81, S82 and S83, whereas compound 600628 binds at an adjacent site near residues V69, F72, W73 and Y76. The adjacent binding sites also include H37, P38, L39, D127, L131, L135 and L138. These residues are in boldface in the sequence of human eIF4E below.

thetic peptides containing the eIF4E-binding motif fused to a penetratin sequence has been shown to induce apoptosis.

By "adjacent to" is meant within 1, 2, 3, 4, or 5 positions upstream ($NH_2$) or downstream (COOH) of the reference amino acid in the reference sequences.

The invention further features a method of identifying a composition that reduces protein synthesis. This method involves contacting an eIF4E polypeptide with a candidate compound and a eIF4G polypeptide and detecting a reduction in the level of eIF4E/eIF4g interaction in the presence of the compound compared to that in the absence of the compound. A reduction of eIF4E/eIF4g interaction indicates that the compound reduces protein synthesis. Optionally, the eIF4E polypeptide comprises residues 68-84 of SEQ ID NO:1; residues 120-140 of SEQ ID NO:1; residues 37-39 of SEQ ID NO:1; or residues 37-39, 68-84 and 120-140 of SEQ ID NO:1. The eIF4E polypeptide can also include at least 6 contiguous residues of SEQ ID NO:1, such that the polypeptide includes at least one of the following residue: residue 37, 38, 39, 69, 72, 73, 76, 81, 82, 83, 127, 131, 135, and 138 of SEQ ID NO:1. The eIF4E polypeptide is murine or human. The IF4E polypeptide can also include a $Y(X)_4L\Phi$ motif, where X is any amino acid and where $\Phi$ is hydrophobic amino acid. Alternatively, the method is carried out by detecting binding of the candidate compound to an eIF4E polypeptide alone or an eIF4g polypeptide alone. The latter method is carried out in fluid phase or with either the initiation factor or candidate compound immobilized on a solid support.

The method features a method of identifying a composition that preferentially inhibits tumor cell proliferation, that involves contacting a cell with any of the compounds described herein. The detection of a reduction in the level of proliferation of a tumor cell in the presence of the compound compared to a non-tumor cell in the presence of this compound indicates that the compound preferentially inhibits tumor cell proliferation. Tumor cell proliferation is preferably at least 10% more compared to non-tumor cells and if desired, the compound is a 2-thiazolyl hydrazone.

The compounds described herein are useful to inhibit protein synthesis thereby inhibiting proliferation of a cell such as a tumor cell or an abnormal cell (benign or malignant cell). An abnormal cell is a cell having an increased proliferation index, a decreased apoptotic index, or both relative to a normal non-cancerous cell. For example, the compounds preferentially or selectively inhibit tumor cell growth compared to normal cell growth. For example, protein synthesis and/or cell proliferation is inhibited at least 10%, 25%, 50%, 75%, 100%, and up to 5-fold, 10-fold and more in tumor cells

```
                                                                     (SEQ ID NO: 1)
  1 MATVEPETTP TPNPPTTEEE KTESNQEVAN PEHYIKHPLQ NRWALWFFKN DKSKTWQANL

61 RLISKFDTVE DFWALYNHIQ LSSNLMPGCD YSLFKDGIEP MWEDEKNKRG GRWLITLNKQ

121 QRRSDLDRFW LETLLCLIGE SFDDYSDDVC GAVVNVRAKG DKIAIWTTEC ENREAVTHIG

181 RVYKERLGLP PKIVIGYQSH ADTATKSGST TKNRFVV
```

During apoptosis, 4E-BP1 undergoes caspase-dependent cleavage of its first 24 amino acids. The N-terminal segment that is eliminated contains a RAIP motif which is needed to start phosphorylation. Thus, the truncated form of 4E-BP1 binds tightly to eIF4E but is not efficiently phosphorylated. The ectopic expression of eIF4E protects cells from apoptosis whereas the overexpression of 4E-BP1 can induce apoptosis in transformed cells. Treatment of cultured cells with syncompared to non-tumor cells. The method is carried out by administering to a patient in need thereof a pharmaceutical composition containing the inhibitory compound. The patient or animal to be treated is identified as one that has a tumor cell containing an increased level of a cap-dependent translation initiation factor compared to the level in a normal non-tumor cell. For example, the patient is diagnosed as having a tumor or abnormal proliferating cells which is characterized by anincreased amount of a cap-dependent translation factor compared to the level in a normal non-tumor cell. For example, the tumor cell contains an aberrantly high amount of eIF4E and/or eIF4G. Such tumor types include tumors of the lung, breast, skin, bone, head (neurological tissues such as brain and spinal cord), neck, bladder, colon, prostate, ovaries, uterus, cervix, larynx, gallbladder, pancreas, rectum, parathyroid, thyroid, adrenal gland, kidney, bronchi, liver, gastrointestinal tract, lymphomas, and neuroblastomas.

As used herein, the term "aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles," "heterocycles," "heteroaryls," or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including, for example, alkylamino, dialkylamino, arylamino, diarylamino, and alkylarylamino), acylamino (including, for example, alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, and methylenedioxyphenyl).

The terms "heterocyclyl" or "heterocyclic group" include closed ring structures, e.g., 3- to 10-, or 4- to 7-membered rings, which include one or more heteroatoms. Heterocyclyl groups can be saturated or unsaturated and include pyrrolidine, oxolane, thiolane, piperidine, piperazine, morpholine, lactones, lactams such as azetidinones and pyrrolidinones, sultams, sultones, and the like. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety.

The term "ether" includes compounds or moieties, which contain oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties, which contain a carbon or a heteroatom bound to an oxygen atom, which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "hydroxy" or "hydroxyl" includes groups with an —OH or —O$^-$.

The term "carboxyl" or "carboxy" includes groups with an —CO$_2$H or —CO$_2^{31}$.

The term "halogen" includes fluorine, bromine, chlorine, iodine, etc. The term "perhalogenated" generally refers to a moiety wherein all hydrogens are replaced by halogen atoms.

"Heteroatom" includes atoms of any element other than carbon or hydrogen. Examples of heteroatoms include nitrogen, oxygen, sulfur and phosphorus.

The structure of some of the compounds of the invention includes asymmetric carbon atoms. It is to be understood accordingly that the isomers arising from such asymmetry (e.g., all enantiomers and diastereomers) are included within the scope of the invention, unless indicated otherwise. Such isomers are obtained in substantially pure form by classical separation techniques and by stereochemically controlled synthesis. Furthermore, the structures and other compounds and moieties discussed in this application also include all tautomers thereof. Alkenes and imines can include either the E- or Z-geometry, where appropriate.

Combination therapy" (or "co-therapy") includes the administration of a modulator compound of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, inhalation, oral routes, intravenous routes, intramuscular routes, subcutaneous, rectal, intraperitoneal, parenteral, transdermal, gastrointestinal, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, therapeutic agents may be administered orally or by intravenous injection. The sequence in which the therapeutic agents are administered is not narrowly critical. "Combination therapy" also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

In accordance with certain other examples, the exemplary compounds provided here can be used in the treatment of cellular proliferation disorders, such as cancer. Treatment of cellular proliferation disorders is intended to include inhibition of proliferation including rapid proliferation. As used herein, the term "cellular proliferation disorder" includes disorders characterized by undesirable or inappropriate proliferation of one or more subset(s) of cells in a multicellular organism. The term "cancer" refers to various types of malignant neoplasms, most of which can invade surrounding tissues, and may metastasize to different sites (see, for example, PDR Medical Dictionary 1st edition (1995)). The terms "neoplasm" and "tumor" refer to an abnormal tissue that grows by cellular proliferation more rapidly than normal and continues to grow after the stimuli that initiated proliferation is removed (see, for example, PDR Medical Dictionary 1st edition (1995)). Such abnormal tissue shows partial or complete lack of structural organization and functional coordination with the normal tissue which may be either benign (i.e., benign tumor) or malignant (i.e., malignant tumor). Treating a disorder characterized by abnormal cellular proliferation is intended to include the prevention of the growth of neoplasms in a subject or a reduction in the growth of pre-existing neoplasms in a subject. Such inhibition also includes the inhibition of the metastasis of a neoplasm from one site to another. The neoplasms are preferably sensitive to the exemplary compounds disclosed here and/or interferon. Examples of types of neoplasms include but are not limited to those neoplasms associated with cancers of the breast, skin, bone, prostate, ovaries, uterus, cervix, liver, lung, brain, larynx, gallbladder, pancreas, rectum, parathyroid, thyroid, adrenal gland, immune system, neural tissue, head and neck, colon, stomach, bronchi, kidneys.

In accordance with another example, certain exemplary compounds provided here can be used in the treatment of viral infections. Treatment of viral infections is intended to include the use of the compounds disclosed here to prevent, or substantially inhibit, the initiation of viral protein synthesis. Treatment of viral infections is also intended to include the use combination of an interferon and the novel compounds disclosed here to inhibit initiation of viral protein synthesis, inhibit elongation of viral protein synthesis, inhibit primary viral RNA transcription, reduce viral infectivity, and reduce budding and release of virions. The term "viral infection," as used herein, refers to one or more cells, which have been, infected with a virus, preferably a DNA or RNA virus. As used herein, RNA viruses include, but are not limited to, virus families such as picornaviridae (e.g., polioviruses), reoviridae (e.g., rotaviruses), togaviridae (e.g., encephalitis viruses), yellow fever virus, rubella virus), orthomyxoviridae (e.g., influenza viruses), paramyxoviridae (e.g., respiratory syncytial virus, measles virus, mumps virus, parainfluenza virus), rhabdoviridae (e.g., rabies virus), coronaviridae, bunyaviridae, flaviviridae, filoviridae, arenaviridae, bunyaviridae, and retroviridae (e.g., human T-cell lymphotropic viruses (HTLV), human immunodeficiency viruses (HIV)). As used herein, DNA viruses include, but are not limited to, virus families such as papovaviridae (e.g., papilloma viruses), adenoviridae (e.g., adenovirus), herpesviridae (e.g., herpes simplex viruses), and poxviridae (e.g., variola viruses). In at least some examples, the viral infection is caused by hepatitis B virus, hepatitis C virus, and/or HIV. Other suitable RNA and DNA viruses will be readily selected by the person of ordinary skill in the art, given the benefit of this disclosure.

In accordance with additional examples, the compounds disclosed here can be used in the treatment of non-proliferative, degenerative disorders associated with aberrant translation initiation. Treatment of non-proliferative, degenerative diseases is intended to include the use of small molecules to inhibit translation initiation. As used herein, the term "non-proliferative degenerative disorder" is intended to include diseases characterized by a loss of function of cells, tissues, and/or organs due to aberrant translation initiation. Non-proliferative degenerative disorders include, but are not limited to, disorders such as Alzheimer's disease and insulin resistance. Other non-proliferative degenerative disorders will be recognized by the person of ordinary skill in the art, given the benefit of this disclosure.

An "anionic group," as used herein, refers to a group that is negatively charged at physiological pH. Preferred anionic groups include carboxylate, sulfate, sulfonate, sulfinate, sulfamate, tetrazolyl, phosphate, phosphonate, phosphinate, or phosphorothioate or functional equivalents thereof. "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. *The Organic Chemistry of Drug Design and Drug Action*, Academic Press, Inc. San Diego, Calif, 1992, pp.19-23). A particularly preferred anionic group is a carboxylate.

The compounds of the invention and the other pharmacologically active agent may be administered to a patient simultaneously, sequentially, or in combination. It will be appreciated that when using a combination of the invention, the compound of the invention and the other pharmacologically active agent may be in the same pharmaceutically acceptable carrier and therefore administered simultaneously. They may be in separate pharmaceutical carriers such as conventional oral dosage forms, which are taken simultaneously. The term "combination" further refers to the case where the compounds are provided in separate dosage forms and are administered sequentially.

A method of synthesizing a compound of Formula I:

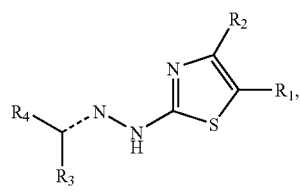

involves:

reacting thiosemicarbazide with an α-bromoketone of Formula II:

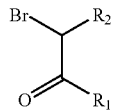

to produce a compound of Formula III:

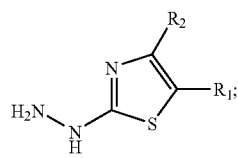

reacting a compound of formula III with a compound of Formula IV:

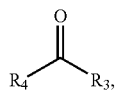

to produce a compound of Formula I, where - - - - - - represents a single bond to form

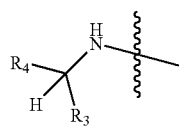

or a double bond to form

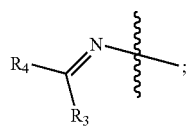

$R_1$ is selected from hydrogen, $C_1$-$C_6$ alkyl, phenyl, substituted phenyl, benzyl, and substituted benzyl;

$R_2$ is selected from methyl, phenyl, substituted phenyl, benzyl, and substituted benzyl; or together $R_1$ and $R_2$ form a phenyl ring;

at least one of $R_3$ and $R_4$ is selected from hydrogen, COOH, COOR$_a$, CH$_2$OH, and CONH$_2$, and the other of $R_3$ and $R_4$ is selected from $C_1$-$C_6$ alkyl, phenyl, substituted phenyl, benzyl and substituted benzyl, and further where:

$R_a$ is $C_1$-$C_6$ alkyl, substituted benzyl and substituted phenyl are benzyl and phenyl moieties, respectively, wherein at least one hydrogen has been replaced with substituent selected from F, Cl, Br, I, NO$_2$, CN, COR$_a$, COOR$_a$, COOH, and C(O)H.

If desired, - - - represents a double bond, $R_1$ is hydrogen, $R_2$ is phenyl or substituted phenyl, one of $R_3$ or $R_4$ is COOH, one of $R_3$ or $R_4$ is CH$_2$OH, or $R_4$ is benzyl. Optionally, COOH is reacted to produce COOCH$_3$, or CH$_2$OH.

A method of synthesizing a compound of Formula V:

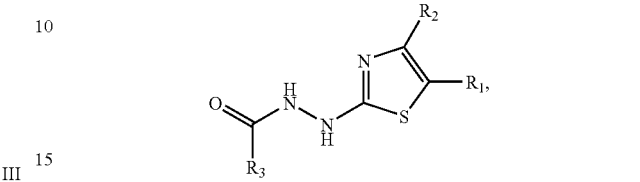

involves:

reacting thiosemicarbazide with an α-bromoketone of Formula II:

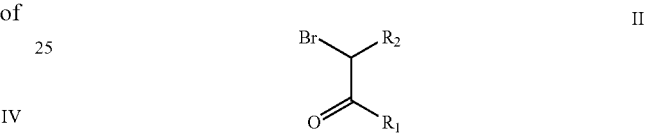

to produce a compound of Formula III:

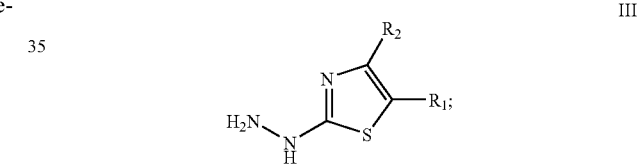

reacting a compound of formula III with a compound of Formula VI:

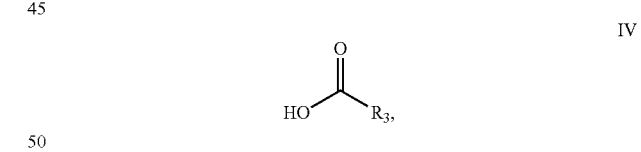

to produce a compound of Formula V, where $R_1$ is selected from hydrogen, $C_1$-$C_6$ alkyl, phenyl, substituted phenyl, benzyl, and substituted benzyl;

$R_2$ is selected from phenyl, substituted phenyl, benzyl, and substituted benzyl; or together $R_1$ and $R_2$ form a phenyl ring;

$R_3$ is selected from $C_1$-$C_6$ alkyl, phenyl, substituted phenyl, benzyl and substituted benzyl, further wherein:

substituted benzyl and substituted phenyl are benzyl and phenyl moieties, respectively, where at least one hydrogen has been replaced with any one of the substituent selected from F, Cl, Br, I, NO$_2$, CN, COR$_a$, COOR$_a$, COOH, and C(O)H, where $R_a$ is $C_1$-$C_6$ alkyl.

Optionally, $R_3$ is benzyl or $R_2$ is phenyl.

A method of synthesizing a compound of Formula B;

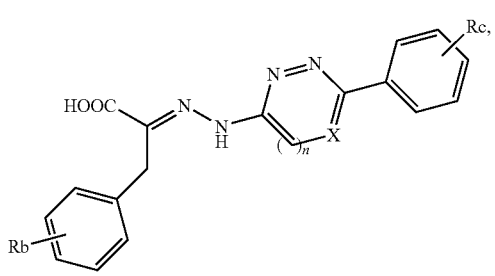

involves reacting a compound of Formula B1:

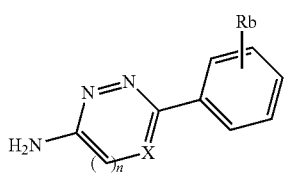

with hydrochloric acid to form a compound of Formula B2:

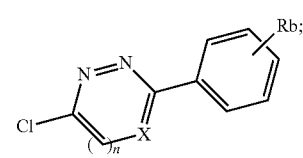

reacting a compound of Formula B2 with hydrazine hydrate to form a compound of Formula B3:

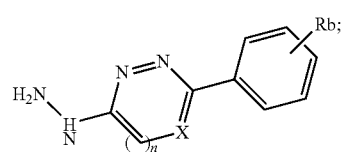

reacting a compound of Formula B3 with a compound of Formula B4:

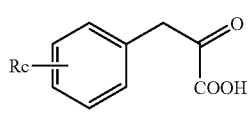

to form a compound of Formula B, where:
n is 0 or 1,
X is S or C, such that when n is 0, X is S; and
$R_b$ and $R_c$ are independently selected from H, $C_1$-$C_6$ alkyl, F, Cl, Br, I, $NO_2$, CN, $COR_a$, $COOR_a$, COOH, and C(O)H, where $R_a$ is $C_1$-$C_6$ alkyl.
Optionally, n is 0 and X is S or n is 1 and X is C. If desired, $R_b$ and $R_c$ are each H.

A method of synthesizing a compound of Formula C,

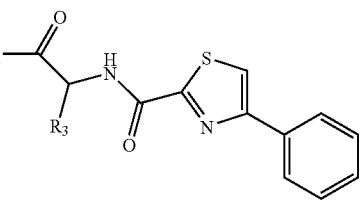

involves: reacting 2-bromo-1-phenylethanone with a carbamoylcarbamate of Formula C1

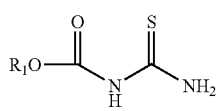

to produce a compound of Formula C2:

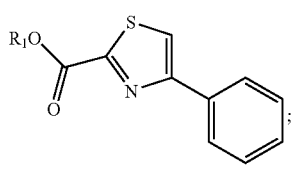

reacting a compound of Formula C2 with base to produce a compound of Formula C3:

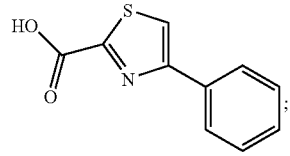

reacting of compound of Formula C3 with 1-[3-(dimethylamino)propyl]-3-ethylcarbodiimide hydrochloride and phenylalanine methyl ester to produce a compound of Formula C, where
$R_1$ is selected from $C_1$-$C_6$ alkyl, phenyl, substituted phenyl, benzyl, and substituted benzyl;
$R_2$ is selected from OH, and $OR_a$, wherein $R_a$ is $C_1$-$C_6$ alkyl; and
$R_3$ is selected from phenyl, substituted phenyl, benzyl, substituted benzyl, and $C_1$-$C_6$ alkyl, further where:
substituted benzyl and substituted phenyl are benzyl and phenyl moieties, respectively, wherein at least one hydrogen has been replaced with substituent selected from F, Cl, Br, I, $NO_2$, CN, $COR_a$, $COOR_a$, COOH, and C(O)H,
Optionally, $R_2$ is OH or $OR_a$. If desired, $R_a$ is methyl or $R_3$ is benzyl. $R_1$ may be ethyl.

A method of synthesizing a compound of Formula D:

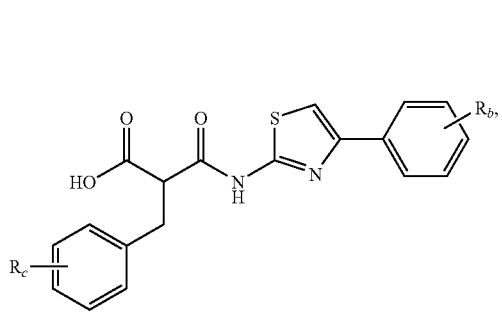

involves a reacting a compound having the formula:

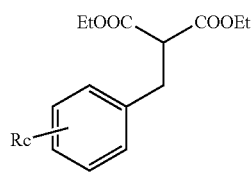

with ethanolic base to form a compound having the formula:

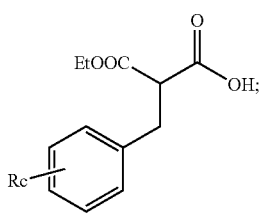

reacting a compound having the formula

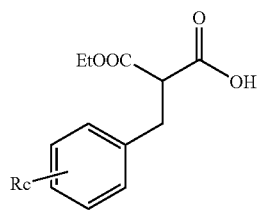

with a compound having the formula

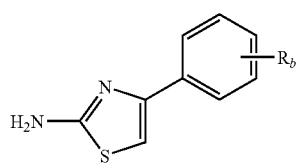

and 1-[3-(dimethylamino)propyl]-3-ethylcarbodiimide hydrochloride to form a compound of Formula D1:

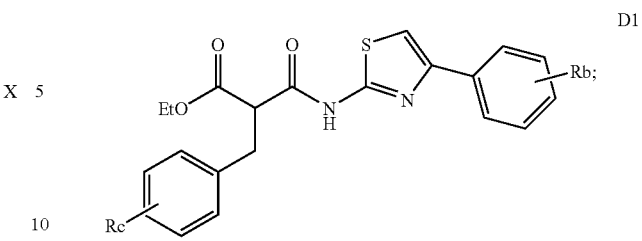

and reacting a compound of formula D1 with base to form a compound of Formula D; wherein $R_b$ and $R_c$ are independently selected from H, $C_1$-$C_6$ alkyl, F, Cl, Br, I, $NO_2$, CN, $COR_a$, $COOR_a$, COOH, and C(O)H, where $R_a$ is $C_1$-$C_6$ alkyl.

Optionally, $R_b$ and $R_c$ are each H.

A method of synthesizing a compound of Formula E:

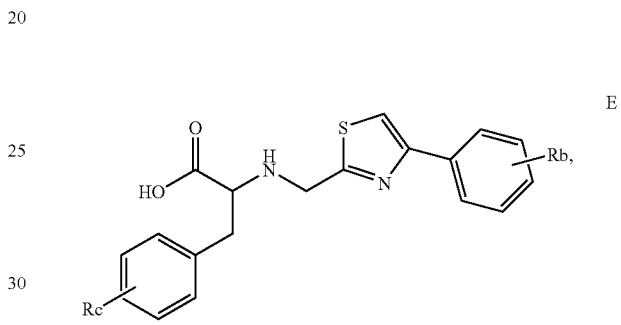

involves reacting a compound having the formula

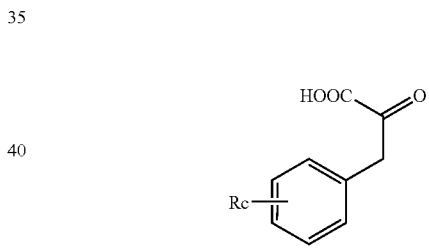

with a compound having the formula

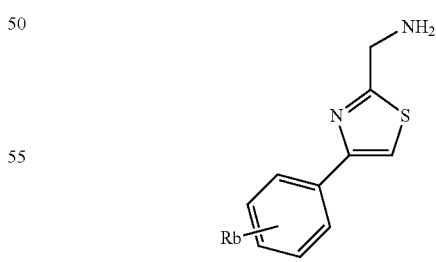

in sodium borohydride, thereby producing a compound of Formula E, wherein $R_b$ and $R_c$ are independently selected from H, $C_1$-$C_6$ alkyl, F, Cl, Br, I, $NO_2$, CN, $COR_a$, $COOR_a$, COOH, and C(O)H, where $R_a$ is $C_1$-$C_6$ alkyl.

Optionally, $R_b$ and $R_c$ are each H.

A method of synthesizing a compound of Formula F:

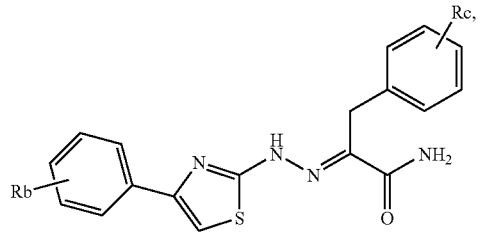

involves reacting a compound of Formula F1,

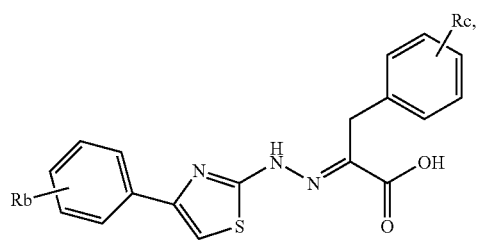

with N-methylmorpholine and isobutylchloroformate to produce a compound of Formula F, wherein $R_b$ and $R_c$ are independently selected from H, $C_1$-$C_6$ alkyl, F, Cl, Br, I, $NO_2$, CN, $COR_a$, $COOR_a$, COOH, and C(O)H, where $R_a$ is $C_1$-$C_6$ alkyl.

Optionally, $R_b$ and $R_c$ are each H.

A method of synthesizing a compound of Formula G:

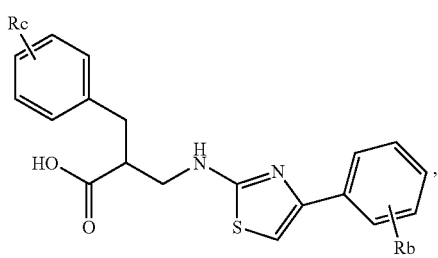

involves reacting a compound having the Formula G1,

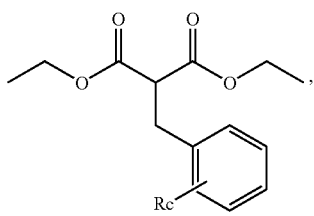

with base to form a compound having the Formula G2,

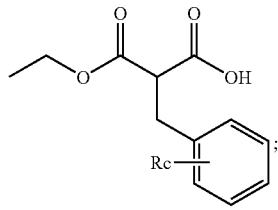

(reacting a compound of formula G2 with benzotriazole-1-yl-oxy-tris-pyrrolidino-phosphonium hexafluorophosphate, diisopropylethylamine, and N, O-dimethylhydroxylamine hydrochloride to form a compound of Formula G3,

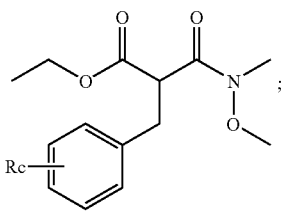

reacting a compound of Formula G3 with lithium aluminum hydride to form a compound G4,

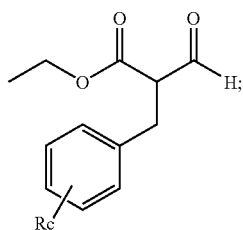

reacting a compound of Formula G4 with a compound of formula G5,

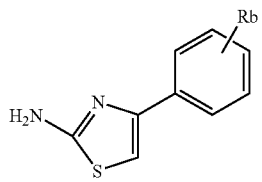

to form a compound of Formula G6,

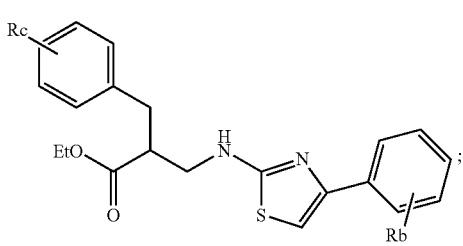

and reacting a compound of Formula G6 with base to form a compound of Formula G, wherein $R_b$ and $R_c$ are independently selected from H, $C_1$-$C_6$ alkyl, F, Cl, Br, I, $NO_2$, CN, $COR_a$, $COOR_a$, COOH, and C(O)H, where $R_a$ is $C_1$-$C_6$ alkyl.

Optioanlly, $R_b$ and $R_c$ are each H.

Other features and advantages of the invention will be apparent from the following description of the preferred embodiments thereof, and from the claims.

BRIEF DESCRIPTION OF THE FIGURES

FIG. 7A is a graph showing a titration with emetine; FIG. 3B is a graph showing a titration with m7GDP; and FIG. 7C is a graph showing titration with EGI-1 (154300).

DETAILED DESCRIPTION

Figure 1A:
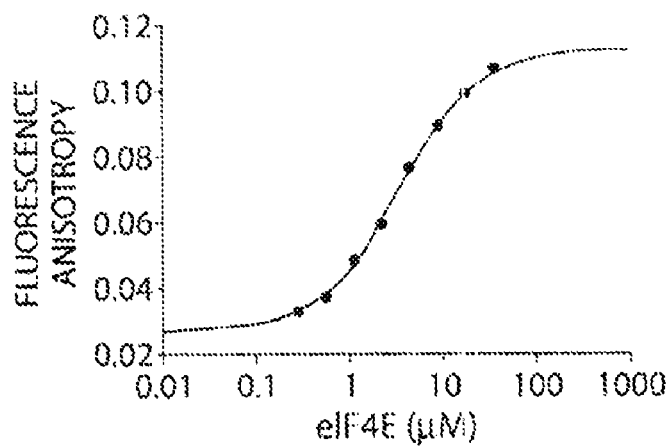
FIG. 1A is a graph showing titration of a fluorescein-labeled eIF4G peptide with eIF4E causes increased fluorescence anisotropy indicating binding of the peptide. The data is fit to a two state binding model.

Many types of tumor cells are characterized by aberrant protein translation initiation mechanisms, e.g., association or binding of certain translation initiation factors. For example, the interaction of the cap-binding protein eIF4E with the mRNA cap, the scaffold protein eIF4G, and the regulatory 4E-BPs, are involved in cell transformation. Small-molecule inhibitors of the eIF4E/eIF4G interaction have been identified and found to possess anti-tumor activity.

Recruitment of the capped 5' end of an mRNA to the small ribosomal subunit is thought to be the major rate limiting step in eukaryotic translation initiation. This process is tightly regulated and requires the stepwise assembly of a large multiprotein complex centered around the trimeric complex eIF4F, comprised of the translation initiation factors eIF4E, eIF4G, and eIF4A. Cap-bound eIF4F recruits the 40S ribosomal subunit through the interaction of eIF3 with eIF4G, which initiates scanning to the initiation codon where it joins with the 60S subunit. This process is facilitated by eIF4A, with the requirement for its helicase activity directly proportional to the amount of secondary structure in the 5' UTR that must be melted for scanning to occur. All eIF4G proteins bind eIF4E through a motif of sequence $Y(X)_4LΦ$, where X is variable and Φ is hydrophobic. This motif forms a helical peptide structure which binds a conserved surface of hydrophobic residues on the dorsal side of eIF4E.

Cellular mRNAs differ greatly in their requirement for eIF4F for efficient translation and in the composition of the 5' UTR. The majority of growth and proliferation related proteins are encoded by "weak" mRNAs containing long highly structured 5' UTRs which have lower translational efficiency than "strong" mRNAs, which contain relatively short and unstructured 5' UTRs. Translation of weak mRNAs is highly eIF4F dependent and is preferentially enhanced when the level of eIF4F complex is increased by eIF4E overexpression. The amount of eIF4E available for complex formation is controlled by a class of small proteins termed 4E-BPs which contain the $Y(X)_4LΦ$ motif and bind to the same surface as eIF4G. In response to stimuli such as nutrients and growth factors 4E-BPs undergo a set of hierarchical phosphorylation events. Hyperphosphorylated forms of 4E-BPs bind eIF4E much more weakly than hypophosphorylated forms, and thus 4E-BP phosphorylation acts as a switch to up-regulate the level of eIF4F and cap-dependent translation. Misregulation of cap-dependent translation due to overexpression of eIF4E and the other components of the eIF4F complex is thought to play an important role in the development of many forms of cancer. In cultured mammalian cells overexpression of eIF4E or eIF4G induces malignant transformation while overexpression of 4E-BP1 partially reverses transformation by eIF4E. In addition, etopic expression of nonphosphorylatable forms of 4E-BP1 can inhibit proliferation and/or induce apoptosis in cancer cell lines. Inhibition of the eIF4F complex is useful for cancer therapy.

Various small molecule inhibitors of this protein interaction were discovered using a fluorescence polarization screening assay. Inhibitors described herein selectively suppress synthesis of growth factors and oncogene products. These molecules specifically bind to a conserved region of hydrophobic residues on the surface of eIF4E that is recognized by a conserved helical peptide motif in eIF4G, thus blocking the interaction of these two proteins. In contrast to traditional inhibitors of translation (e.g., cyclohexamide) which act non-specifically, these molecules are selective inhibitors of cap-dependent translation, a significant improvement over existing general inhibitors of protein synthesis.

The compounds described herein were identified by screening the ChemBridge library (16,000 compounds), which block the binding of a fluorescently labeled eIF4G-derived peptide to eIF4E in a fluorescence polarization assay. Three of the candidate inhibitors have estimated $K_D$ values of 10 µM or more: ICCB-5582 (10 µM), EGI-1 or ICCB-15644 (2 µM), and ICCB-6737 (1 µM). NMR titration experiments demonstrate competitive binding of EGI-1 to a surface region of eIF4E which interacts with a conserved peptide motif in eIF4G. This compound displaces full-length eIF4G from eIF4E, causes increased binding of 4E-BP1 to eIF4E, and specifically inhibits cap-dependent translation. In cultured cells, EGI-1 appears to specifically inhibit production of malignancy-related proteins with mRNAs containing highly structured 5' UTRs. All three of these compounds inhibited cap-dependent translation in vitro in the rabbit reticulocyte lysate system. Compounds ICCB-5582 and ICCB-15644 inhibited the proliferation of cultured A549 cells (a lung cancer cell line), both with approximate IC50 values of 6 µM. EGI-1 induces apoptosis in the human Jurkat lymphoma cell line, and also inhibits the growth of the A549 lung cancer and HT29 colon cancer cell lines. The identification of EGI-1 provides a novel tool for the study of translationally regulated cellular processes and a potential starting point for the development of more potent inhibitors.

Identification of Small Molecules

Figure 1B:
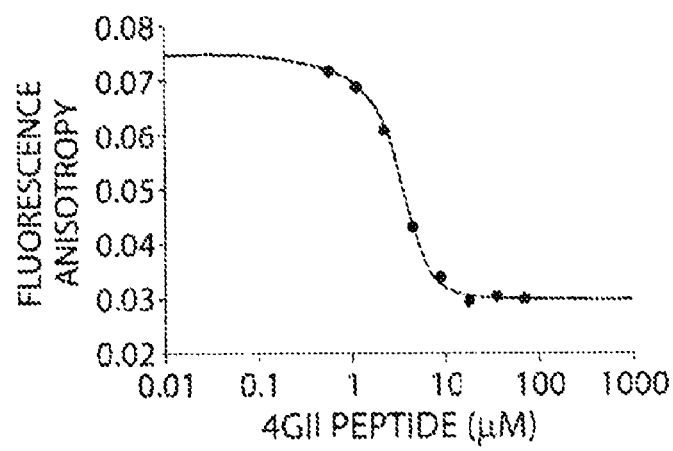
FIG. 1B is a graph showing competitive inhibition of labeled peptide binding to eIF4E by an unlabeled eIF4GII peptide as measured by decrease in fluorescence polarization. The data is fit to a three state competitive binding model.
Figure 1C:
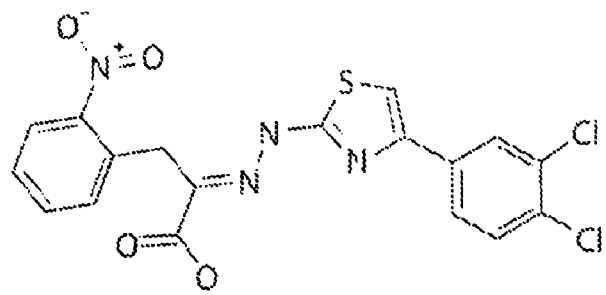
FIG. 1C shows the chemical structure of EGI-1.

We have undertaken a reverse chemical genetic screen to identify small molecules that selectively target the eIF4F complex by inhibiting the interaction between eIF4E and eIF4G. We developed a fluorescence polarization (FP) assay to measure binding of a fluorescein tagged peptide containing the $Y(X)_4L\Phi$ motif to eIF4E. Titration of this peptide with eIF4E caused the fluorescence anisotropy of the label to increase almost three-fold (FIG. 1A). Addition of an unlabeled competitor eIF4GII peptide to the labeled peptide/eIF4E complex caused anisotropy to decrease to the level of free labeled peptide (FIG. 1B), validating the assay as a method for identification of inhibitors. We adapted this assay to a microwell plate format and used it to screen the 16,000 compound Chembridge DiverSet E library. A hit compound from this screen (referred to as EGI-1) was chosen for further characterization based on its relatively potent inhibition of peptide binding (FIG. 1D) and drug-like structure (FIG. 1C). By fitting the anisotropy data to equations describing the competitive equilibria in this assay, the binding affinity of EGI-1 for eIF4E was estimated to be lower than 24.5+/−9.6 µM.

EGI-1 Competitively Inhibits Binding of eIF4G to eIF4E

NMR spectroscopy was employed to characterize the interaction of EGI-1 with eIF4E Although backbone chemical shift assignments for a complex of murine eIF4E with an eIF4G peptide have been determined, assignments for the unbound form of eIF4E were next determined. Murine eIF4E is identical to the human protein in its structured portion, except for a D174E replacement at a structurally and functionally unimportant position. As murine eIF4E is unstable at the concentration levels required for triple resonance NMR experiments, a more soluble form of the protein was developed by fusing a solubility enhancement tag (SET), the 56 residue GB1 domain of protin G, to the amino terminus of eIF4E. The fusion protein exhibited significantly enhanced solubility and analysis of the HSQC spectra of native and tagged proteins confirmed that the tag had no affect on the structure of eIF4E. Using this construct, the majority of backbone chemical shift assignments for uncomplexed murine eIF4E was determined using standard NMR methods. The protein was titrated with EGI-1 or the conserved peptide from eIF4GII and resulting changes in the $^{15}N$ HSQC spectrum were analyzed. Titration of GB1-eIF4E with EGI-1 had no effect on the GB1 resonances but caused selective line broadening of a subset of eIF4E peaks in the HSQC spectrum. This indicates intermediate chemical exchange on the NMR timescale, which is typical of ligands that bind with low-micromolar affinities. There was significant overlap between those peaks most strongly affected by EGI-1 binding (FIG. 1F) and those that shift in position upon eIF4GII peptide binding (FIG. 1E), indicating the compound inhibits binding of the peptide by interacting with the same surface of eIF4E.

EGF-1 Inhibits eIF4F Complex Formation and Cap-Dependent Translation

Figure 2A:
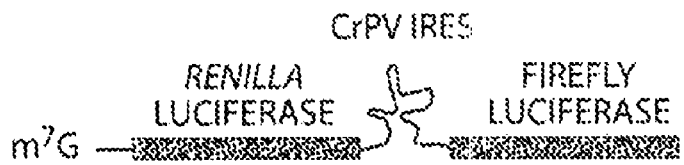
FIG. 2A is a diagram showing the dual luciferase mRNA reporter construct containing *Renilla* luciferase (translated in cap-dependent fashion) and firefly luciferase (translation driven by cricket paralysis virus IRES).
Figure 2B:
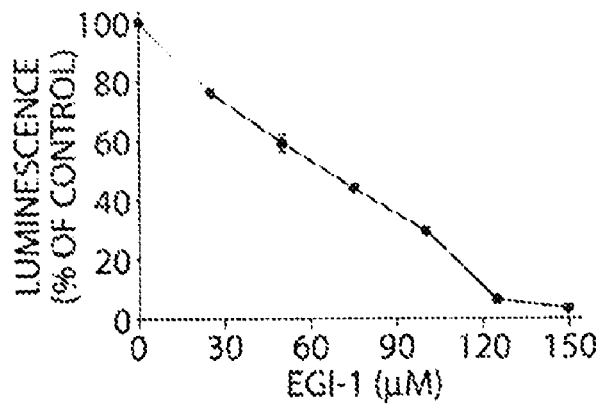
FIG. 2B is a graph showing that EGI-1 inhibits cap-dependent translation in rabbit reticulocyte lysate as measured by synthesis of *Renilla* luciferase. Error bars correspond to standard error of the mean.
Figure 2C:
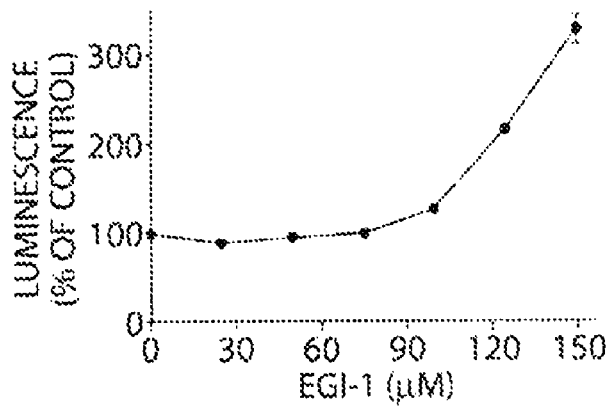
FIG. 2C is a graph showing that EGI-1 does not inhibit IRES driven translation in rabbit reticulocyte lysate as measured by synthesis of firefly luciferase. Error bars correspond to standard error of the mean.
Figure 2D:
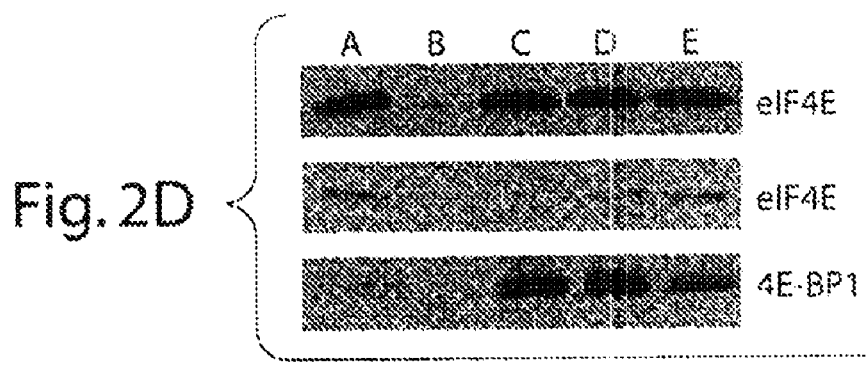
FIG. 2D is a photograph of a series of immunoblots showing the effect of EGI-1 on association of eIF4E with eIF4G and 4E-BP1 in rabbit reticulocyte lysate, as determined by a m⁷GTP Sepharose pull-down assay and Western blotting. A: Untreated, B: 200 μm GDP, C: 200 μm EGI-1, D: 100 μm EGI-1, E: 50 μm EGI-1.

The effect of EGI-1 in rabbit reticulocyte lysate, a model system for the mammalian translation, was next examined. To determine the relative effects of the compound on cap dependent and independent translation, we utilized a bicistronic mRNA construct containing the gene for *Renilla* luciferase under the control of the cap and the message for firefly luciferase under the control of the cricket paralysis virus IRES (FIG. 2A). Translation of proteins driven by this IRES does not require initation factors. The in vitro translation of the cap-dependent message is inhibited in a dose-dependent manner by EGI-1 (FIG. 2B), while cap-independent translation is not inhibited and in fact significantly enhanced (presumably due to increased availability of ribosomes as cap-dependent translation is shut down) (FIG. 2C). To determine if this is due to disruption of eIF4F complexes in reticulocyte lysate, we used an $m^7GTP$ Sepharose pull-down assay to measure the state of association of eIF4E with its binding partners (FIG. 2D). This shows that EGI-1 displaces full-length eIF4G from eIF4E while causing increased binding of 4E-BP1. These results indicate that 4E-BP1 is still able to bind to eIF4E due to additional intermolecular contacts not disrupted by compound binding, and thus dissociation of eIF4E/eIF4G complexes allows increased formation of 4E-BP1/eIF4E complexes.

Figure 3A:
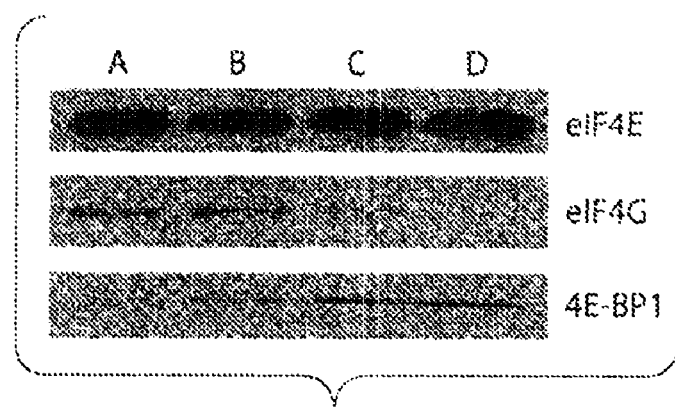
FIG. 3A is a photograph of a series of immunoblots showing the effect of 6 hrs EGI-1 treatment on association of eIF4E with eIF4G and 4E-BP1 in Jurkat cells as determined by a m⁷GTP Sepharose pull-down assay and Western blotting. A: Untreated, B: 25 μM EGI-1, C: 50 μM EGI-1, D: 100 μM EGI-1. EGI-1 inhibits eIF4F complex formation and the expression of proteins encoded by mRNAs with highly structured 5' UTRs in cells.
Figure 3B:
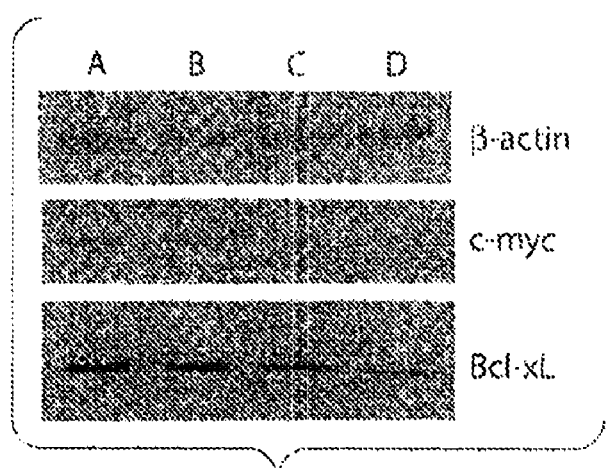
FIG. 3B is a photograph of a series of immunoblots showing the effect of EGI-1 treatment over 8 hours on protein levels as measured by Western blotting of Jurkat cell extracts. A: Untreated, B: 25 μM EGI-1, C: 50 μM EGI-1, D: 100 μM EGI-1.
Figure 3C:
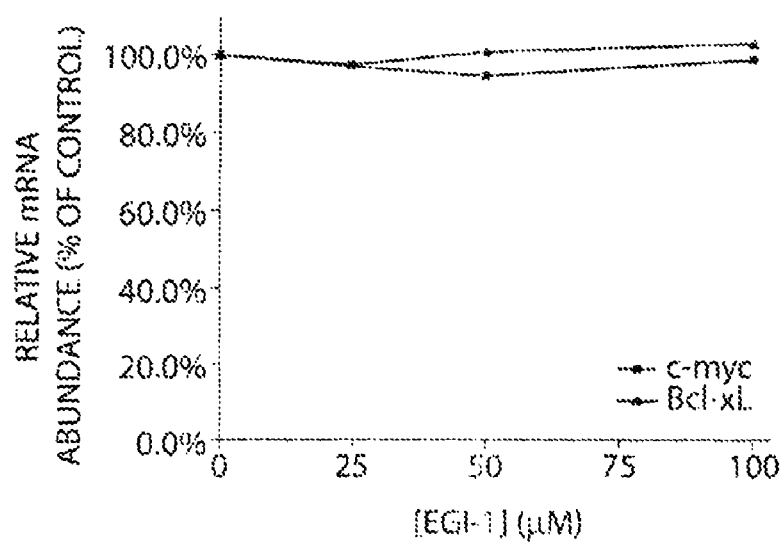
FIG. 3C is a graph showing that EGI-1 does not affect nucleocytoplasmic transport or stability of c-myc and Bcl-xL mRNA in Jurkat cells. Cells were treated with compound for 8 hrs and relative abundance of the two mRNAs relative to β-actin was determined by quantitative real-time PCR.

EGF-1 Inhibits eIF4F Complex Formation and the Expression of Proteins Encoded by mRNAs with Highly Structured 5′ UTRs in Cells Having characterized the activity of EGI-1 in vitro, the effect of the compound in living cells was next examined. This inhibitor disrupts the eIF4F complex in human Jurkat T cells: after a 6 hour treatment with the compound eIF4G is displaced from eIF4E while binding of 4E-BP1 is increased, similar to the effect in vitro (FIG. 3A). The total level of eIF4G or 4E-BP1 is not significantly affected by the compound treatment. EGI-1 likely inhibits the production of proteins encoded by weak mRNAs with highly structured 5′ UTRs in a preferential manner (e.g, Bcl-xL and c-myc) while having little or no effect on strong mRNAs such as β-actin. Analysis of extracts from Jurkat cells treated for 8 hours with the compound shows that this is the case (FIG. 3B). Importantly, analysis of mRNA abundance in the cytoplasm by real time PCR shows that EGI-1 does not affect the transcriptional level, transport, or stability of these mRNAs, indicating that production of these proteins is inhibited at the level of translation (FIG. 3C).

EGI-1 Exhibits Activity against Cancer Cell Lines

Figure 4A:
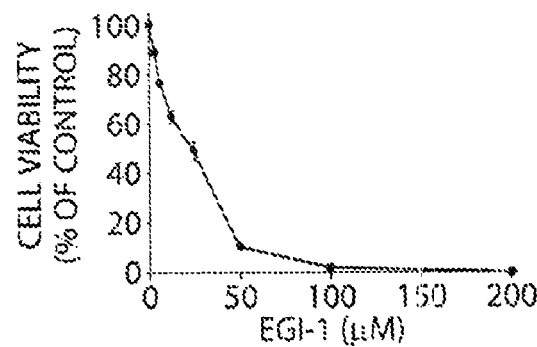
FIG. 4A is a graph showing that EGI-1 induces loss of cell viability in Jurkat cells as measured by decrease in intracellular ATP level. Bars correspond to standard error of the mean.
Figure 4B:
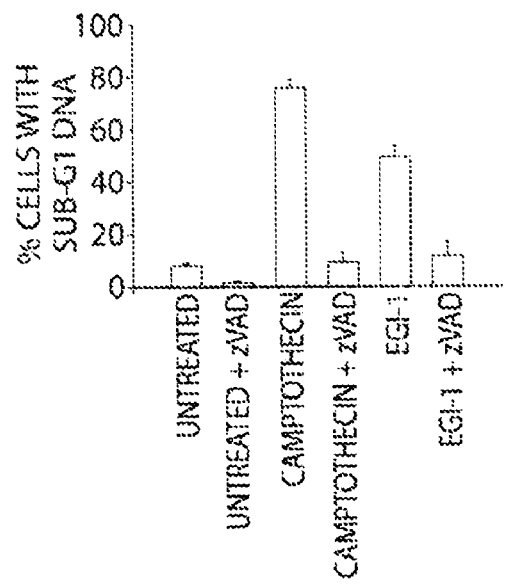
FIG. 4B is a bar graph showing that EGI-1 induces DNA fragmentation in Jurkat cells. Jurkat cells were treated with 60 μM EGI-1 or 6.65 μM camptothecin for 24 hours with or without 100 μM zVAD-FMK. The percentage of cells having sub-G1 DNA content was determined via FACS analysis. Bars correspond to standard error of the mean.
Figure 4C:
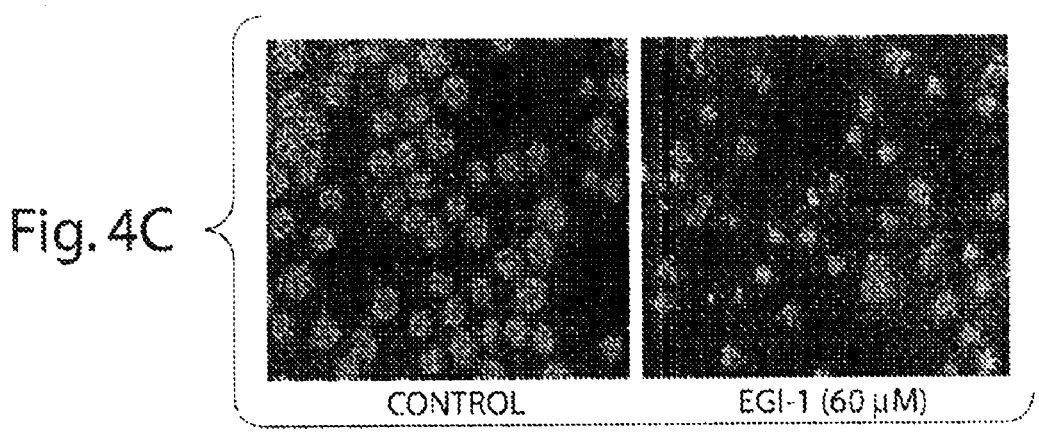
FIG. 4C is a series of photographs showing that EGI-1 induces fragmented nuclear morphology in Jurkat cells. Cells were treated with 60 μM EGI-1 for 24 hours, stained with Hoechst 33342 dye, and visualized by fluorescence microscopy.
Figure 4D:
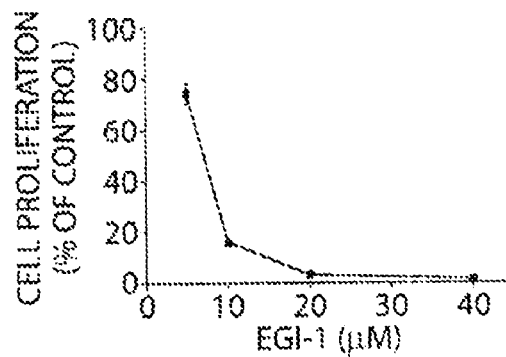
FIG. 4D is a graph showing that EGI-1 inhibits proliferation of A549 lung cancer cells as measured by the SRB assay after a five day growth period. Error bars correspond to standard error of the mean.

Further characterization of EGI-1 in Jurkat cells showed that this compound has pro-apoptotic activity. After 24 hours, cells treated with the compound exhibit dose-dependent loss of cell viability as measured by cellular ATP level (FIG. 4A). Flow cytometry analysis of cellular DNA content shows that EGI-1 causes a large increase in the sub-G1 fraction (corresponding to fragmented DNA) (FIG. 4B), which can be suppressed by co-treatment with the broad spectrum caspase inhibitor zVAD-FMK. Furthermore, the treated cells exhibit a fragmented nuclear morphology that is characteristic of apoptosis (FIG. 4C). EGI-1 also exhibits activity against other cancer cell lines. The compound inhibits the growth of A549 lung cancer cells as measured by an SRB assay, with an $IC_{50}$ of approximately 6 μM (FIG. 4D). In addition, EGI-1 inhibits the growth of HT29 colon cancer cells with an $IC_{50}$ of 9 μM. Such results can result from pro-apoptotic and/or anti-proliferative activity in these cell lines.

In summary, we have developed a reverse chemical genetic screen to identify small molecule inhibitors of the eIF4E/eIF4G interaction and have successfully identified as one such inhibitor the compound EGI-1. This compound is a competitive inhibitor of binding of the conserved eIF4G recognition peptide to eIF4E and disrupts this protein complex both in vitro and in cells. EGI-1 is an inhibitor of cap-dependent translation and selectively downregulates the expression of proteins encoded by mRNAs with highly structured 5′ UTRs, many of which have key roles in malignancy. The compound can induce apoptosis in Jurkat lymphoma cells and exhibits activity against other human cancer cell lines. The identification of EGI-1 provides a new tool for targeting the eIF4F complex which can be used in the study of numerous biological processes which depend on translational control. It also provides a starting point for development of more potent inhibitors.

Synthesis of 2-thiazolyl Hydrazones I

The general synthetic approach to the synthesis of the 2-thiazolyl hydrazones is described in Scheme 1. Substituted 2-thiazolyl hydrazines (2) were prepared by Hantzsch-typed cyclodehydration of thiosemicarbazide with appropriate bromoacetones (1) in dioxane at room temperature. The condensation reactions between 2-thiazolyl hydrazines (2) with appropriated ketones or a-keto acid (3) in the presence of 5% acetic acid yielded the substituted 2-thiazolyl hydrazones (4).

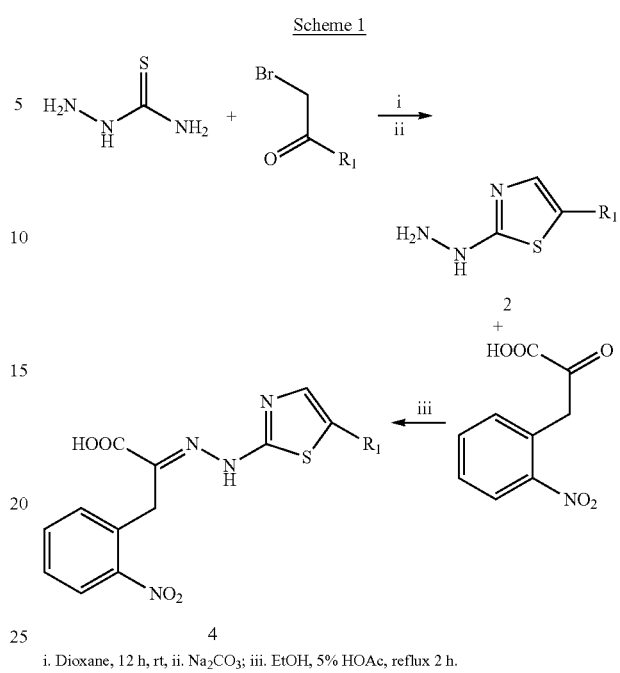

Scheme 1 i. Dioxane, 12 h, rt, ii. Na₂CO₃; iii. EtOH, 5% HOAc, reflux 2 h.

¹H NMR spectra were recorded at 500 MHz on a Varian VX500 or at 400 MHz on a Varian VX400 instrument in d-DMSO as solvents. TLC analyses were performed on Kieselgel 60 F254 silica gel plates purchased from EMD chemicals, Inc. with UV illumination at 254 nm. Column chromatography was performed on Baker 7024 flash silica gel. Melting points were measured in Pyrex capillary tubes in a Mel-Temp "Electronthermal" apparatus and are not corrected. LC-MS was performed in Waters LC-MS (APCI mode) with XTerra C₈ 30×100 mm column. Elemental analyses were obtained only for the final products, and were performed by Robertson Laboratories, Madison, N.J., and were within ±0.4% of theoretical values. All the starting materials were purchased commercially available and used without further purification.

Procedure for synthesis 2-{[4-(3,4-Dichloro-phenyl)-thiazol-2-yl]-hydrazono}-3-(2-nitro-phenyl)-propionic acid Step 1

4-(3,4-Dichloro-phenyl)-thiazol-2-yl-hydrazine

A solution of a thiosemicarbazide (10 mmol, 0.91 g) and 3,4-dichlorophenylacetyl bromide (10 mmol, 2.68 g) in dioxane (20 mL) was stirred at room temperature for 16 h. The precipitate of hydrobromide salt was filtered and washed with dioxane (3×10 mL) basified with 2N Na₂CO₃ (20 mL). The product was filtered, washed with water and dried (2.08 g, 80%). The product was generally satisfactory for further reaction. ¹H NMR (400 MHz) δ 8.67 (s, 1H, NH), 8.00 (d, J=1.6 Hz, 1H), 7.76 (dd, J=1.6 Hz, J=8.4 Hz, 1H), 7.60 (d, J=8.4 Hz, 1H), 7.31 (s), 1H MS⁺(APCI), 259.68, (M+1; calcd 258.97 (M+)

Step 2

2-{[4-(3,4-Dichloro-phenyl)-thiazol-2-yl]-hydrazono}-3-(2-nitro-phenyl)-propionic acid 3-(2-Nitro-phenyl)-2-oxo-propionic acid (1.0 mmol, 209 mg) in 5% acetic acid (2 mL) was added in to solution of 4-(3,4-dichloro-phenyl)-thiazol-2-yl-hydrazine (1.0 mmol, 259 mg) in ethanol (4 mL). The reaction mixture was stirred at 90° C. for 1 h and cooled to 0° C.; the orange solid was precipitated out, filtered and washed by water. Recrystallization from MeOH—H$_2$O afford the final product as a yellow powder (600 mg, 66.7%). mp ; Z/E isomer was further separated by HPLC-MS, using gradient eluting solvents: 0.05% HOAc in acetonitrile 50%: 0.05% HOAc in water 50% to 0.05% HOAc in acetonitrile 75%: 0.05% HOAc in water 25% in 20 min. $^1$H NMR (400 MHz) δ 12.85 (br, 1H), 12.10 (br, 1H), 8.06 (d, J=8.4 Hz, 1H), 8.03(s, 1H), 7.78 (d, J=8.4 Hz, 1H), 7.64 (d, J=6.0 Hz, 2H), 7.61(s, 1H), 7.50 (t, J=7.6 Hz, 1H), 7.06 (d, J=7.6 Hz, 1H), 4.28 (s, 2H). $^{13}$C NMR (125.78 MHz) δ 166.097, 164.759, 149.785, 134.607, 134.281, 133.663, 132.596, 132.182, 131.543, 130.680, 129.559, 128.927, 127.854, 126.318, 125.795, 125.299, 108.552, 36.896. Z-isomer: $^1$H NMR (400 MHz) δ 12.35 (br, 1H), 12.10 (br, 1H), 8.06 (dd, J=8.4 Hz, 1H), 8.03(s, 1H), 7.78 (d, J=8.4 Hz, 1H), 7.64 (d, J=6.0 Hz, 2H), 7.61(s, 1H), 7.50 (t, J=7.6 Hz, 1H), 7.06 (d, J=7.6 Hz, 1H), 4.12 (s, 2H).

MS$^+$(APCI) m/z 450.84 (M+), calcd: 450.84 (M+). Anal. Calcd for C$_{18}$H$_{14}$N$_4$O$_4$S.0.2H$_2$O: C, 47.53; H, 2.75; N, 12.32; Found: C, 47.41; H, 2.59; N, 11.98.

2-[(4-phenyl)-thiazol-2-yl)-hydrazono]-3-(2-nitro-phenyl)-propionic acid (4a)

Z/E isomer was further separated by HPLC-MS, using a 30 min linear gradient of 50-75% of 0.05% HOAc in acetonitril 50% in 0.05% HOAc in water. The gradient eluting solvents included 0.05% NH$_4$OAc in acetonitrile 50%: 0.05% NH$_4$OAc in water 50% to 0.05% NH$_4$OAc in acetonitrile 75%: 0.05% NH$_4$OAc in water 25% in 30 min. $^1$H NMR (500 MHz) δ 12.90 (br, 1H), 12.15 (br, 1H), 8.01 (d, J=8.5 Hz, 1H), 7.80(d, J=6.5 Hz, 2H), 7.61 (t, J=8.0 Hz, 1H), 7.46 (t, J=8.5 Hz, 1H), 7.37 (t, J=8.0 Hz, 2H), 7.28 (s, 1H), 7.25 (t, J=7.5 Hz, 1H), 7.15 (d, J=7.5 Hz, 1H), 4.26 (s, 2H). MS$^+$(APCI) m/z 383.04 (M+1), calcd: 382.07 (M$^+$). Anal. Calcd for C$_{18}$H$_{14}$N$_4$O$_4$S: C, 56.54; H, 3.69; N, 14.65; Found: C, 56.35; H, 3.51; N, 14.45.

2-[(4-Biphenyl-4-yl-thiazol-2-yl)-hydrazono]-3-(2-nitro-phenyl)-propionic acid (4f)

E isomer was further separated by HPLC-MS using a 30 min linear gradient of 50-75% of 0.05% HOAc in acetonitril 50% in 0.05% HOAc in water. The gradient eluting solvents included. Gradient eluting solvents included 0.05% NH$_4$OAc in acetonitrile 50%: 0.05% NH$_4$OAc in water 50% to 0.05% NH$_4$OAc in acetonitrile 75%: 0.05% NH$_4$OAc in water 25% in 30 min. $^1$H NMR (400 MHz) δ 12.90 (br, 1H), 12.15 (br, 1H), 8.01 (dd, J=1.2 Hz, J=8.0 Hz, 1H), 7.88(d, J=8.8 Hz, 2H), 7.69 (m, 4H), 7.60 (dt, J=0.8 Hz, J=7.6 Hz, 1H), 7.44 (m, 3H), 7.34 (m, 2H), 7.13 (d, J=8.0 Hz, 1H), 4.24 (s, 2H). MS$^+$(APCI) m/z 458.91 (M+1), calcd: 458.10 (M$^+$). Anal. Calcd for C$_{24}$H$_{18}$N$_4$O$_4$S: C, 62.87; H, 3.96; N, 12.22; Found: C, 62.52; H, 3.96; N, 12.22; Found C, 62.52; H, 4.01;N, 12.02.

2-[(4-Naphthalen-2-yl-thiazol-2-yl)-hydrazono]-3-(2-nitro-phenyl)-propionic acid (4c)

E isomer was further separated by HPLC-MS, using gradient eluting solvents: 0.05% NH$_4$OAc in acetonitrile 50%: 0.05% NH$_4$OAc in water 50% to 0.05% NH$_4$OAc in acetonitrile 75%: 0.05% NH$_4$OAc in water 25% in 30 min. $^1$H NMR (400 MHz) δ 12.90 (br, 1H), 12.10 (br, 1H), 8.32 (s, 1H), 8.04(d, J=8.0 Hz, 1H), 7.96 (d, J=9.2H, 2H), 7.60 (dt, J=0.8 Hz, J=7.6 Hz, 2H), 7.44 (m, 3H), 7.34 (m, 2H), 7.88 (t, J=8.4 Hz, 3H), 7.62 (t, J=7.6 Hz, 1H), 7.48(m, 4H), 4.27 (s, 2H). MS$^+$(APCI) m/z 432.88 (M+1); 432.09 (M$^+$). calcd: Anal. Calcd for C$_{22}$H$_{16}$N$_4$O$_4$S.0.3H$_2$O: C, 60.35; H, 3.82; N, 12.80; Found: C, 60.14; H, 3.80; N, 12.63.

3-(2-Nitro-phenyl-2-{[4-(4-phenylazo-phenyl)-thiazol-2-yl]-hydrazono}-propionic acid (4j)

E isomer was further separated by HPLC-MS, using gradient eluting solvents: 0.05% NH$_4$OAc in acetonitrile 50%: 0.05% NH$_4$OAc in water 50% to 0.05% NH$_4$OAc in acetonit 75%: 0.05% NH$_4$OAc in water 25% in 30 min. $^1$H NMR (400 MHz) δ 12.80 (br, 1H), 12.10 (br, 1H), 8.07 (d, J=8.4 Hz, 1H), 8.03(d, J=8.8 Hz, 2H), 7.92(d, J=8.4 Hz, 2H), 7.91 (d, J=8.4 Hz, J=2 Hz, 2H), 7.88 (dd, J=8.4 Hz, J=2 Hz, 2H), 7.87 (dd, J=0.8 Hz, J=7.6 Hz, 1H), 7.65 (t, J=9.6 Hz, 2H), 7.55 (m, 4H), 7.08 (d, J=8.0 Hz, 1H), 4.31 (s, 2H). MS$^+$(APCI) m/z 486.98 (M+1), calcd: 486.11 (M$^+$). Anal. Calcd for C$_{24}$H$_{18}$N$_6$O$_4$S.0.5H$_2$O: C, 58.17; H, 3.86; N, 16.96; Found: C, 58.47; H, 3.76; N, 16.68.

Synthesis of 2-thiazolyl Hydrazones II

The general synthetic approach to the synthesis of the 2-thiazolyl hydrazones is described in Scheme 3. Substituted 2-thiazolyl hydrazines (2) were prepared by Hantzsch-typed cyclodehydration of thiosemicarbazide with appropriate bromoacetones (1) in dioxane at room temperature. The condensation reactions between 2-thiazolyl hydrazines (2) with appropriated ketones or α-keto acid (3) in the presence of 5% acetic acid yielded the substituted 2-thiazolyl hydrazones (4).

2-Phenyl-5-hydrazineo-1,3,4-thiadiazole (2k) were obtained by diazotization of 2-amino-5-phenyl-1,3,4-thiadiazoles in hydrochloric acid with copper catalysis followed by treatment with hydrazine hydrate. The final product (4k) was synthesized by condensation with α-keto acid. 3-Phenyl-2-[(6-phenyl-pyridazin-3-yl)-hydrazono]-propionic acid (4l) was synthesized by a similar fashion.

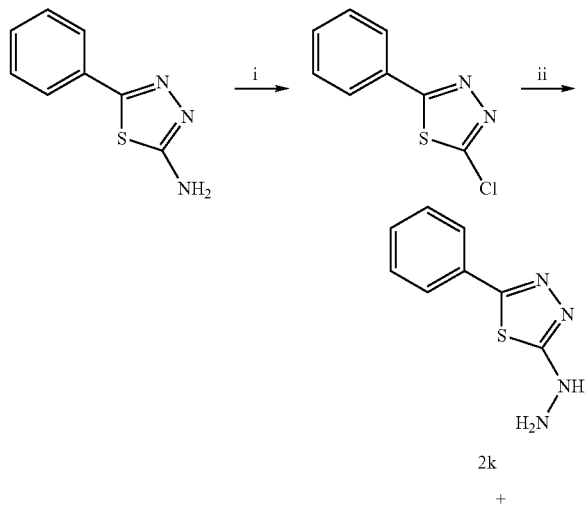

Scheme 2

-continued

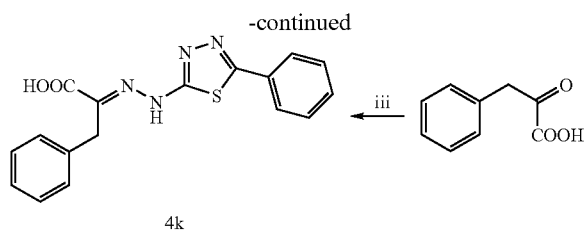

4k i. NaNO$_2$/HCl/Cu; ii. N$_2$H$_4$; iii. EtOH, 5% HOAc, reflux 2 h

Assignment of Z- and E-Isomers

High-resolution 1H NMR spectroscopy revealed that the condensation product that in DMSO-d6 existed as a mixture of E and Z isomers pertaining to the stereochemistry of the carbon-nitrogen double bond. In most of the cases (except 4m) the pure E or Z isomers can be separated by using preparative HPLC with a C$_{18}$ reverse phase column. Assignment of the stereochemistry was based upon the consideration that in the E isomer, the NH group and the CH$_2$(Z-4c, $\delta_H$=3.75 ppm attached to C=N are in proximity, resulting in an upfield shift compared to the chemical shift of Z isomer (E-4c, $\delta_H$=4.04 ppm, this shift being due to the known γ-steric affect. In this case (4c) E is the predominant isomer. Variation in isomeric rations might be due to the different sizes of R$_3$ and R$_4$ group. This result is consistent with the report by Dimmock and Rezessy. However, they also both reported that the pure E isomers underwent E to Z isomerization after standing in solutions. In order to check the stability of the pure isomers to determine if there is transformation into Z/E mixtures in physiological condition, solution were prepared in deuterated eIF4E buffer and spectra were recorded by high resolution $^1$H NMR after dissolution of pure isolated isomers as well as 1 h, 1 day. Interestingly, the testing revealed that they are stable configurationally.

2-[(4-phenyl)-thiazol-2-yl)-hydrazono]-3-(2-nitrophenyl)-propionic acid

Z/E isomer was further separated by HPLC-MS, using gradient eluting solvents: 0.05% NH$_4$OAc in acetonitrile 50%: 0.05% NH$_4$OAc in water 50% to 0.05% NH$_4$OAc in acetonitrile 75%: 0.05% NH$_4$OAc in water 25% in 30 min. E-isomer: $^1$H NMR (500 MHz) δ 8.01 (d, J=8.5 Hz, 1H), 7.80 (d, J=6.5 Hz, 2H), 7.61 (t, J=8.0 Hz, 1H), 7.46 (t, J=8.5 Hz, 1H), 7.37 (t, J=8.0 Hz, 2H), 7.28 (s, 1H), 7.25 (t, J=7.5 Hz, 1H), 7.15 (d, J=7.5 Hz, 1H), 4.26 (s, 2H). Z-isomer: $^1$H NMR (500 MHz) δ 8.03 (d, J=8.0 Hz, 1H), 7.80 (d, J=7.0 Hz, 2H), 7.69 (t, J=8.0 Hz, 1H), 7.52 (m, 2H), 7.38 (t, J=8 Hz, 2H), 7.29 (t, J=7.5 Hz, 1H), 7.26 (s, 1H), 4.15 (s, 2H).

MS$^+$(APCI) m/z 382.07 (M$^+$), calcd: 383.04 (M+1). Anal. Calcd for C$_{18}$H$_{14}$N$_4$O$_4$S: C, 56.54; H, 3.69; N, 14.65; Found: C, 56.35; H, 3.51; N, 14.45.

2-{[4-(3,4-Dichloro-phenyl)-thiazol-2-yl]-hydrazono}-3-phenyl-propionic acid

Z/E isomer was further separated by HPLC-MS, using gradient eluting solvents: 0.05% NH$_4$OAc in acetonitrile 50%: 0.05% NH$_4$OAc in water 50% to 0.05% NH$_4$OAc in acetonitrile 75%: 0.05% NH$_4$OAc in water 25% in 30 min. E-isomer: $^1$H NMR (500 MHz) δ 8.01 (d, J=8.5 Hz, 1H), 7.80 (d, J=6.5 Hz, 2H), 7.61 (t, J=8.0 Hz, 1H), 7.46 (t, J=8.5 Hz, 1H), 7.37 (t, J=8.0 Hz, 2H), 7.28 (s, 1H), 7.25 (t, J=7.5 Hz, 1H), 7.15 (d, J=7.5 Hz, 1H), 4.26 (s, 2H). Z-isomer: $^1$H NMR (500 MHz) δ 8.03 (d, J=8.0 Hz, 1H), 7.80 (d, J=7.0 Hz, 2H), 7.69 (t, J=8.0 Hz, 1H), 7.52 (m, 2H), 7.38 (t, J=8 Hz, 2H), 7.29 (t, J=7.5 Hz, 1H), 7.26 (s, 1H), 4.15 (s, 2H).

MS$^+$(APCI) m/z 382.07 (M$^+$), calcd: 383.04 (M+1). Anal. Calcd for C$_{18}$H$_{13}$Cl$_2$N$_4$O$_4$S: C, 52.21; H, 3.23; N, 10.34; Found: C, 53.34; H, 3.45; N, 10.40.

Formulations and Methods of Administering Therapeutic Formulations

Subjects diagnosed as having or at risk of developing a condition (e.g., tumor) in which eIF4E, F, or G are elevated are treated using the compounds described herein. Exemplary conditions include, e.g., tumors of the lung, breast, head (neurological tissues such as brain and spinal cord), neck, bladder, colon, prostate, liver, gastrointestinal tract, lung, lymphomas, and neuroblastomas. Treatment with these compounds may also be beneficial for other cancers that overexpress other translation initiation or for non-cancerous proliferative disorders such as vein craft rejection and restinosis, as well as for non-proliferative degenerative disorders, disorders associated with aberrant apoptosis, and disorders associated with viral and bacterial infections in human and other mammals.

A therapeutic regimen is carried out by identifying a mammal, e.g., a human patient suffering from (or at risk of developing) a cancer or metastases or other proliferative disorders, non-proliferative degenerative disorders and disorders associated with viral and bacterial infections using standard methods. For example, inhibitory compounds are administered to an individual diagnosed with a cancer.

The compounds are preferably administered intravenously or orally. For example, EGI-1 or compound 154300 is formulated into a salt to enhance its solubility and absorbance, and compound 600628 is formulated with an emulsifier for oral administration or with a pharmaceutically-acceptable solvent for intravenous administration.

For oral administration, the compounds are formulated by combining the active compound(s) with pharmaceutically acceptable carriers, which are readily selected by those skilled in the art, given the benefit of this disclosure. Such carriers enable the exemplary compounds disclosed here to be formulated as tablets, pills, dragees, capsules, liquids, gels, syrups, slurries, suspensions and the like, for oral ingestion by a patient to be treated. Pharmaceutical preparations for oral use are formulated with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents are added, such as the cross-linked polyvinyl pyrrolidone, agar, or alginic acid or a salt thereof such as sodium alginate. In certain examples, dragee cores are provided with suitable coatings. For this purpose, concentrated sugar solutions can be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

In accordance with other examples, pharmaceutical preparations for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner. For administration by inhalation, the compounds can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin, for example, for use in an inhaler or insufflator can be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

In accordance with certain other examples, pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use. The compounds can also be formulated in rectal compositions such as suppositories or retention enemas, e.g., containing conventional suppository bases such as cocoa butter or other glycerides.

In yet other examples and in addition to the formulations described above, the compounds can also be formulated as a depot preparation. Such long acting formulations can be administered by implantation or transcutaneous delivery (for example subcutaneously or intramuscularly), intramuscular injection or a transdermal patch. For example, the compounds can be formulated with suitable polymeric or hydrophobic materials (for example as an emulsion in an acceptable oil) or ion exchange resins, or as sparingly soluble derivatives, for example, as a sparingly soluble salt. The pharmaceutical compositions also can include suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

In accordance with other examples, pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In all cases, the composition preferably is sterile and is fluid to the extent that it may be drawn into and/or delivered using a syringe. Such compositions preferably are stable under the conditions of manufacture and storage and are be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

In certain other examples, the compounds are prepared as oral compositions. Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In other embodiments, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These materials may be prepared according to methods known to those skilled in the art, for example, as described in U.S. Pat. No. 4,522,811.

An appropriate dosage level is generally be about 0.001 to 50 mg/kg patient body weight per day, which may be administered in single or multiple doses. If given orally, the dosage level may be about 0.01 to about 30 mg/kg per day, e.g., 0.01 to about 1, 3, 5, 7, 10, 15, 20, 25 or 30 mg/kg per day. If given intravenously, the dosage levels may be somewhat lower, e.g., 0.01 to about 0.3, 1, 3, 5, 7 or 10 mg/kg per day. For example, in the treatment or prevention of a disorder of the central nervous system, a suitable oral dosage level may be about 0.01 to about 30 mg/kg per day, e.g., 0.01 to about 1, 3, 5, 7, 10, 15, 20, 25 or 30 mg/kg per day. The compounds may be administered on a regimen of 1 to 4 times per day, preferably once or twice per day.

It will be appreciated that the amount of the compound of the invention required for use in any treatment will vary not only with the particular compounds or composition selected but also with the route of administration, the nature of the condition being treated, and the age and condition of the patient, and will ultimately be at the discretion of the attendant physician.

The compositions and combination therapies of the invention may be administered in combination with a variety of pharmaceutical excipients, including stabilizing agents, carriers and/or encapsulation formulations as described herein.

Aqueous compositions of the present invention comprise an effective amount of the compounds of the invention, dissolved or dispersed in a pharmaceutically acceptable carrier or aqueous medium.

"Pharmaceutically or pharmacologically acceptable" include molecular entities and compositions that do not produce an adverse, allergic or other untoward reaction when administered to an animal, or a human, as appropriate. "Pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. For human administration, preparations meet sterility, pyrogenicity, general safety and purity standards as required by FDA Office of Biologics standards.

The compositions and combination therapies of the invention are generally formulated for parenteral administration, e.g., formulated for injection via the intravenous, intramuscular, subcutaneous, intralesional, or even intraperitoneal routes. The preparation of an aqueous composition that contains a composition of the invention or an active component or ingredient will be known to those of skill in the art in light of the present disclosure. Typically, such compositions are prepared as injectables, either as liquid solutions or suspensions; solid forms suitable for using to prepare solutions or suspensions upon the addition of a liquid prior to injection can also be prepared; and the preparations can also be emulsified. Other formulations include an ointment, paste, spray, patch, cream, gel, resorbable sponge, or foam. Such formulations are produced using methods well known in the art.

In some cases, the compound is administered topically. For example, to treat urinary bladder cancer, the compound is administered to the bladder using methods well known in the art, e.g., using a catheter to inflate the bladder with a solution containing the compound. For treatment of skin malignancies, a cream or ointment is applied to the area of skin affected by the tumor. Tumor cells in the liver are treated by infusing into the liver vasculature a solution containing the compound. Alternatively, the compounds are administered by implanting (either directly into an organ such as the liver or subcutaneously) a solid or resorbable matrix which slowly releases the compound into adjacent and surrounding tissues of the subject. For treatment of cancers of the CNS, the compound is systemically administered or locally administered directly into CNS tissue. The compound is administered intravenously or intrathecally (i.e., by direct infusion into the cerebrospinal fluid). For local administration, a compound-impregnated wafer or resorbable sponge is placed in direct contact with CNS tissue. Alternatively, the compound is infused into the brain or cerebrospinal fluid using known methods.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. For administration by injection into a tissue, the form is sterile and fluid to the extent that easy syringability exists. It remains stable under the conditions of manufacture and storage and must be preserved against the contaminating action of microorganisms, such as bacteria and fungi.

Solutions of active compounds as free base or pharmacologically acceptable salts are prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Therapeutic or pharmacological compositions of the present invention will generally comprise an effective amount of the component(s) of the combination therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including cremes, lotions, mouthwashes, inhalants and the like.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for intramuscular injection is also contemplated. In this regard, the use of DMSO as solvent is preferred as this will result in extremely rapid penetration, delivering high concentrations of the active compound(s) or agent(s) to a small area.

The use of sterile formulations, such as saline-based washes, by surgeons, physicians or health care workers to cleanse a particular area in the operating field may also be particularly useful. Therapeutic formulations in accordance with the present invention may also be reconstituted in the form of mouthwashes, or in conjunction with antifungal reagents. Inhalant forms are also envisioned. The therapeutic formulations of the invention may also be prepared in forms suitable for topical administration, such as in cremes and lotions.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

Upon formulation, therapeutics are administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. An exemplary dosage is dissolved in 1 ml of isotonic NaCl solution and either added to 1000 ml of hypodermolysis fluid or injected at the proposed site of infusion, (see for example, *Remington's Pharmaceutical Sciences* 15th Edition, pages 1035-1038 and 1570-1580).

In certain embodiments, active compounds are administered orally. This is contemplated for agents which are generally resistant, or have been rendered resistant, to proteolysis by digestive enzymes. Such compounds are contemplated to include chemically designed or modified agents; dextrorotatory peptides; and peptide and liposomal formulations in time release capsules to avoid peptidase and lipase degradation.

Pharmaceutically acceptable salts include acid addition salts and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier is optionally a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze drying techniques which yield a powder of the active ingredient plus any additional desired ingredient from a previously sterile-filtered solution thereof.

The preparation of more, or highly, concentrated solutions for direct injection is also contemplated, where the use of DMSO as solvent is envisioned to result in extremely rapid penetration, delivering high concentrations of the active agents to a small area.

Additional formulations suitable for other modes of administration include suppositories. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders.

In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabensas preservatives, a dye and flavoring, such as cherry or orange flavor.

The liquid forms in which the compositions of the invention may be incorporated for administration orally or by injection include aqueous solution, suitably flavored syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For treating clinical conditions and diseases noted above, the compound of this invention is administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

Translation Initiation Factors and Efficiency of Protein Translation

Figure 5A:
FIG. 5A is a diagram of the structure of eIF4E bound to eIF4G.

The majority of growth and proliferation proteins are encoded by "weak" mRNAs containing long highly structured 5' UTRs: in quiescent cells these are translated with much lower efficiency than "strong" mRNAs, which contain relatively short and unstructured 5' UTRs. Translation of these weak mRNAs has a much greater dependence on eIF4F and is preferentially enhanced when the level of eIF4F complexes is increased by eIF4E overexpression. The level of available eIF4E in the cell is regulated by a class of small proteins termed 4E-BPs. All eIF4G proteins contain a conserved motif of sequence $Y(X)_4L\Phi$, where X is variable and $\Phi$ is hydrophobic. This motif forms a helix which binds a conserved surface of hydrophobic residues on the dorsal side of eIF4E (FIG. 5A). The 4E-BPs also contain this motif and compete with eIF4G for available eIF4E. Hierarchical phosphorylation of the 4E-BPs controls their activity: hypophosphorylated 4E-BPs bind to eIF4E with full affinity while hyperphosphorylated states have greatly reduced affinity. This level of phosphorylation thus acts as a switch which increases the level of eIF4E available to form translationally active eIF4F complexes in response to extracellular stimuli such as nutrients and growth factors. These signals are primarily transduced through the PI3/Akt pathway to activate the kinase mTOR, which phosphorylates 4E-BPs both directly and possibly indirectly through the action of downstream mTOR-dependent kinases.

eIF4E/eIF4G Interaction and Tumorigenesis

The disruption of proper translational regulation by elevated levels of eIF4F complexes is an important factor in carcinogenesis. A wide variety of tumors have been found to have abnormally elevated eIF4E levels, and eIF4G is amplified in some lung cancers. The overexpression of eIF4E in cultured cells can cause them to exhibit a malignant transformed phenotype: rapid proliferation, loss of contact inhibition, and anchorage-independent growth. This transformation is dependent on eIF4E's ability to bind eIF4G, as co-expression of 4E-BP1 in these cells can partially reverse their malignant properties. Elevated eIF4E levels are detected in cancers of the breast, head, neck, bladder, colon, prostate, gastrointestinal tract and lung, Hodgkin's lymphomas, and neuroblastomas. In breast cancer patients, the risk of cancer recurrence and cancer-related death is correlated with the level of eIF4E overexpression. The other components of eIF4F are overexpressed in specific types of cancer: eIF4G in squamous cell lung carcinomas, and eIF4A in melanomas and primary hepatocellular carcinomas.

Loss of proper regulation of the eIF4E-eIF4G interaction plays an important role in the development of many cancers. The protein-protein interaction between eIF4E and eIF4G is an essential step in cap-dependent translation initiation. Because the translation of the mRNAs encoding most proteins involved in cellular growth and proliferation is highly cap-dependent, regulation of the level of complex formation between eIF4E and eIF4G plays an important role in the control of these processes. The interaction between these proteins is inhibited by the 4E binding proteins (4E-BPs), which compete with eIF4G for binding to the same surface on eIF4E. Phosphorylation of specific sites on 4E-BPs in response to growth and proliferation signals inhibits their ability to bind eIF4E.

The level of eIF4E/eIF4G complex formation also plays a role in the control of apoptosis. 4E-BP1 has been found to undergo a caspase cleavage of its N-terminus which removes a motif necessary for it to undergo phosphorylation, leading to increased 4E-BP1 binding to eIF4E and inhibition of cap-dependent translation. This inhibition causes a shift in the levels of pro and anti apopoptic proteins to favor apoptosis. Experiments in cultured cells have shown that peptides containing the eIF4E recognition motif of eIF4G fused to a penetratin sequence can induce apoptosis.

Identification of Inhibitors of Translation Factor Protein-Protein Interactions

Chemical library synthesis and fluorescence assay technologies were used to identify small molecule inhibitors of protein-protein interactions by screening large numbers of compounds. These compounds provide tools for "reverse chemical genetics", in which a small molecule which selectively regulates the activity of a protein is used to elucideat its role in biological processes. A chemical inhibitor of the eIF4E/eIF4G interaction specifically inhibits cap-dependent translation, and inhibits tumor growth and progression in tumor types that are characterized by eIF4E or eIF4G overexpression.

The following reagents and methods were used to identify small molecule inhibitors.

Protein Cloning, Expression, and Purification

The fusion protein GB1-meIF4E was constructed by cloning the full coding sequence of murine eIF4E into a GB1 expression vector using the BamHI and EcoRI sites. Both tagged and native eIF4E was expressed in *E. coli* using standard methods and purified using affinity chromatography on m7GDP or m7GTP agarose resin.

Fluorescence Polarization Assay

The C-terminal fluorescein labeled peptide has sequence KYTYDELFQLK (SEQ ID NO:2) and was synthesized by Research Genetics using standard methods. This sequence contains the $Y(X)_4L\Phi$ motif and was optimized for solubility and binding to eIF4E. The unlabeled competitor eIF4GII peptide has the sequence KKQYDREFLLDFQFMPA (SEQ ID NO:3) and was synthesized by Tufts University Core Facility using standard methods. For screening and subsequent peptide binding assays measurements of fluorescence polarization were made using an LJL Analyst plate reader. For the screening assay a solution containing approximately 5 µM meIF4E, 60 nM labeled peptide, 0.05% bovine γ-globulin, and 2 mM DTT in a buffer composed of 50 mM sodium phosphate and 50 mM potassium chloride at pH 6.5 was used. Approximately 17 nM fluorescein-eIF4G peptide was used in the assay. For measurements of fluorescence anisotropy to be used in curve fitting the labeled peptide concentration was increased to 1 µM and γ-globulin was omitted. The curve fitting for estimation of binding constants used equations derived by Roehrl et al.[22] Measurements of fluorescence polarization and anisotropy were made in black 384-well plates (Corning) using an Analyst plate reader (LJL Biosystems) Compounds were transferred to plates during the screening using a custom-built Seiko pin transfer robot at the Institute for Chemistry and Cell Biology (ICCB) at Harvard Medical School.

NMR Spectroscopy

All protein samples for NMR were in a buffer composed of 50 mM sodium phosphate, 50 mM potassium chloride, and 2 mM DTT at pH 6.5. For high concentration protein samples the DTT concentration was increased to 20 mM. For the backbone assignment experiments 15N, 13C, and 85% or 90% deuterated GB1-meIF4E was used. The standard three pairs of triple resonance experiments were recorded: HNCAIHN(CO)CA, HNCO/HN(CA)CO, and HNCACB/HN(CO)CACB. The HNCAIHN(CO)CA dataset was recollected using a higher protein concentration and TROSY versions of the experiments in order to get better sensitivity. In addition, an $^{15}$N-HSQC-NOESY experiment, HSQCs of specific $^{15}$N Lys, Ile, Leu, and Val labeled samples of GB1-meIF4E, and an HSQC of a reverse Arg labeled sample were recorded to facilitate the backbone assignments. For titration experiments, 300 µM GB1-meIF4E was mixed with 300 µM EGI-1, or 100 µM protein was mixed with 70 µM eIF4GII peptide (same sequence as used in FP assay)

Computational Docking

The program TreeDock (Fahmy et al., 2002, J. Am. Chem. Soc. 124(7): p. 1241-50, hereby incorporated by reference) was used for computational docking.

In vitro Translation

A dicistronic reporter construct containing the *Renilla reniformis* luciferase sequence after the 5' UTR followed by the CrPV IRES and the firefly luciferase sequence was used to build a reporter construct plasmid. The reporter construct plasmid was linearized with BamHI and transcribed in vitro with an ARCA cap using the mMessage Machine T7 Ultra Kit (Ambion). In vitro translation reactions were carried out using Red Nova reticulocyte lysate (Novagen) with 2 mM magnesium acetate and 153 mm potassium acetate, incubated at 30 degrees C. for 90 minutes. Translation of reporter genes was measured using the Dual-Glo luciferase assay (Promega) in a Wallac Victor$^2$ plate reader.

Alamar Blue Assay

Adherent human solid tumor cells were plated and maintained for 3 days in the presence of increasing concentration of the compounds, and cell proliferation was measured by alamar blue assay, where 10% of commercially available solution is added to the cell medium and measure fluorescence in 96-well plates at wavelength of 530 nm excitation and 590 nm emission. The data calculations were carried out as previously described.

m$^7$GTP Pull-Down Assay

For the in vitro version of the assay, aliquots of Red Nova reticulocyte lysate with the same salt and buffer concentrations as in the translation reactions were incubated with compound or 200 µM m$^7$GDP) for 1 hour at 37 degrees C. Following incubation the lysate was incubated with m$^7$GTP-Sepharose beads for 1 hour at 4 degrees C. After extensive washing bound proteins were eluted with free m$^7$GTP, resolved by SDS-PAGE, and subjected to Western blotting using a polyclonal antibody against 4E-BP1 (Cell Signaling Technology), and monoclonal antibodies against eIF4E and eIF4G (Transduction Laboratories). For the cell based version of the assay Jurkat cells were grown for 6 hours in the presence of the compound, harvested by centrifugation, and lysed by multiple freeze-thaw cycles. Extracts prepared by this method were analyzed using the same pull-down protocol as with the reticulocyte lysates.

Cell Culture Experiments

For analysis of cellular protein and mRNA levels, Jurkat cells were grown for 8 hours in the presence of the compound. Extracts for Western blotting were prepared from half of the cells by multiple freeze-thaw cycles. β-actin, Bcl-xL, and c-myc were detected using polyclonal antibodies (Cell Signaling). For the remaining cells the PARIS kit (Ambion) was used to isolate total nuclear and total cytoplasmic RNA fractions. The integrity of the fractionation was confirmed by agarose gel electrophoresis (as prescribed by Ambion). Contaminating DNA was removed using the DNA-free kit (Ambion), and cDNA was prepared using MMLV reverse transcriptase (Promega). The relative abundance of the c-myc and Bcl-xL messages compared to β-actin was determined by real-time PCR with validated QuantiTec probes and the QuantiTec SYBR Green Kit (Qiagen), using a thermocycler from Applied Biosystems.

Cell viability was measured by treatment of Jurkat cells with compound for 24 hours and determination of intracellular ATP using the CellTiterGlo assay (Promega). For measurement of apoptotic DNA fragmentation cells were treated for 24 hours with 60 µM EGI-1 or 6.65 µM camptothecin in the presence or absence of 100 µM zVAD-FMK, a broad-spectrum caspase inhibitor. After fixation and staining with PI cellular DNA content was determined by FACS analysis in a FACSCalibur machine (Beckton Dickinson). Nuclear morphology after 24 hour EGI-1 treatment was visualized by staining of cells with Hoechst 33342 dye and fluorescence microscopy.

A lung cancer cell line, A549, was used in a proliferation assay known in the art, e.g., Fan et al. Bioorg. Med. Chem. Lett. 14: 2547-50, 2004. The cytotoxicity assaying was carried out by incubating plated cells in the presence of compound for 16 hours and determining cell viability using the CellTiter-Glo luminescence cell assay (Promega). For the A549 lung cancer cells cell growth in the presence of EGI-1 was determined using the SRB staining method as previously described. For the HT29 colon cancer cells cell growth was determined using an Alamar Blue assay.

Screening and Structural Characterization of Inhibitory Compositions

Figure 5B:
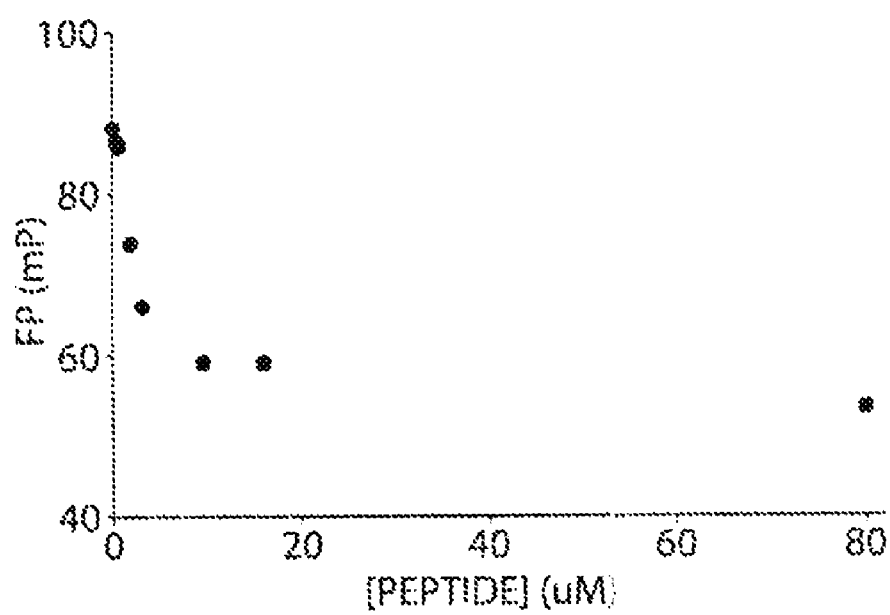
FIG. 5B is a dot plot showing loss of FP signal on titration with unlabeled eIF4G peptide.

A fluorescence polarization (FP) assay was developed to measure binding of a peptide containing the conserved eIF4E-binding motif to eIF4E. The peptide is conjugated to fluorescein at its carboxyl terminus, and when titrated with purified eIF4E its fluoresence polarization, increases almost three-fold as the fraction of bound labeled peptide increases. When a competitor unlabeled eIF4G peptide is added to the mixture of labeled peptide and eIF4E the FP goes down to the basal level observed with the free peptide (FIG. 5B). This system thus provided a simple and sensitive assay for detecting small molecules which can disrupt the protein-protein interaction between eIF4E and eIF4G by competitively binding to the same conserved hydrophobic surface as the consensus peptide.

Figure 1D:
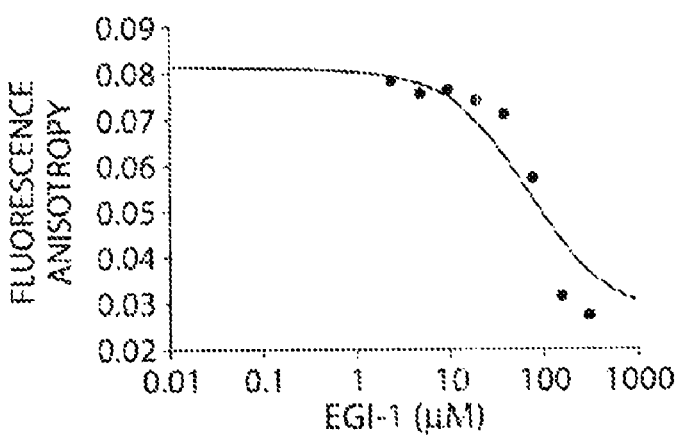
FIG. 1D is a graph showing competitive inhibition of labelled peptide binding to eIF4E by the compound EGI-1 as measured by decrease in fluorescence polarization. The data is fit to a three state competitive binding model.
Figure 1E:
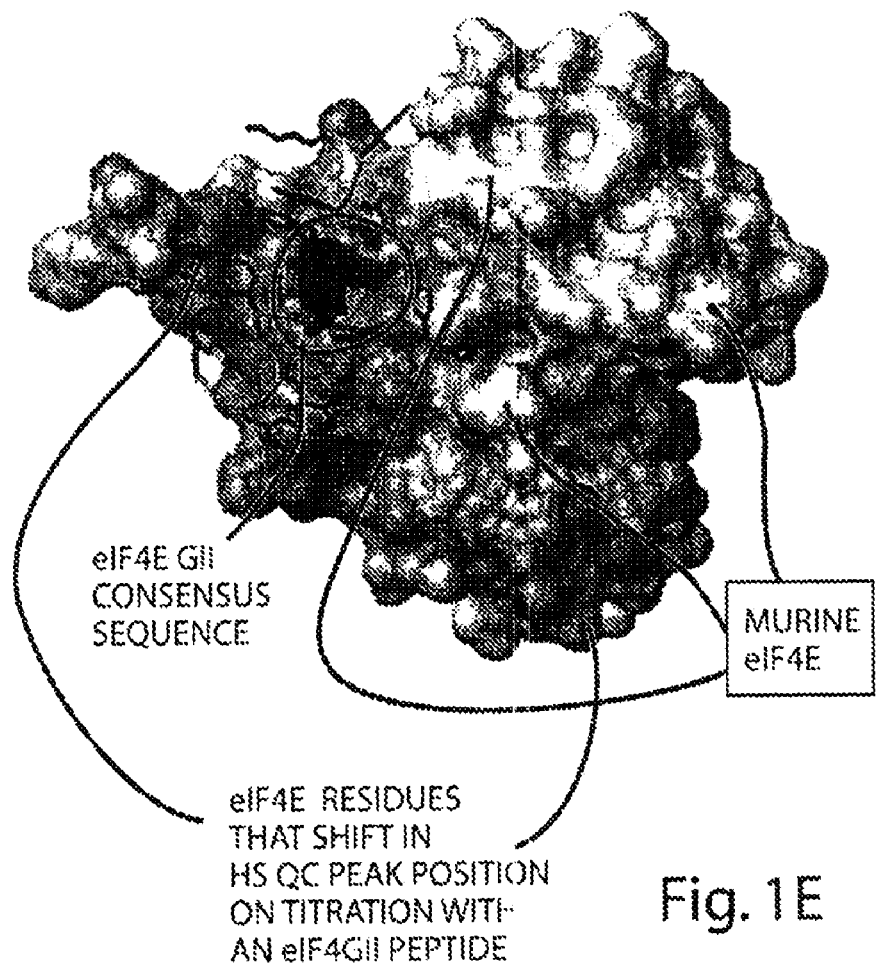
FIG. 1E is a schematic showing chemical shift perturbations of eIF4E induced by eIF4G peptide binding. The surface representation structure of the crystal structure murine eIF4E (light areas) in complex with the eIF4GII consensus peptide (circled) is shown: eIF4E residues which shift in HSQC peak position on titration with an eIF4GII peptide are shaded.
Figure 1F:
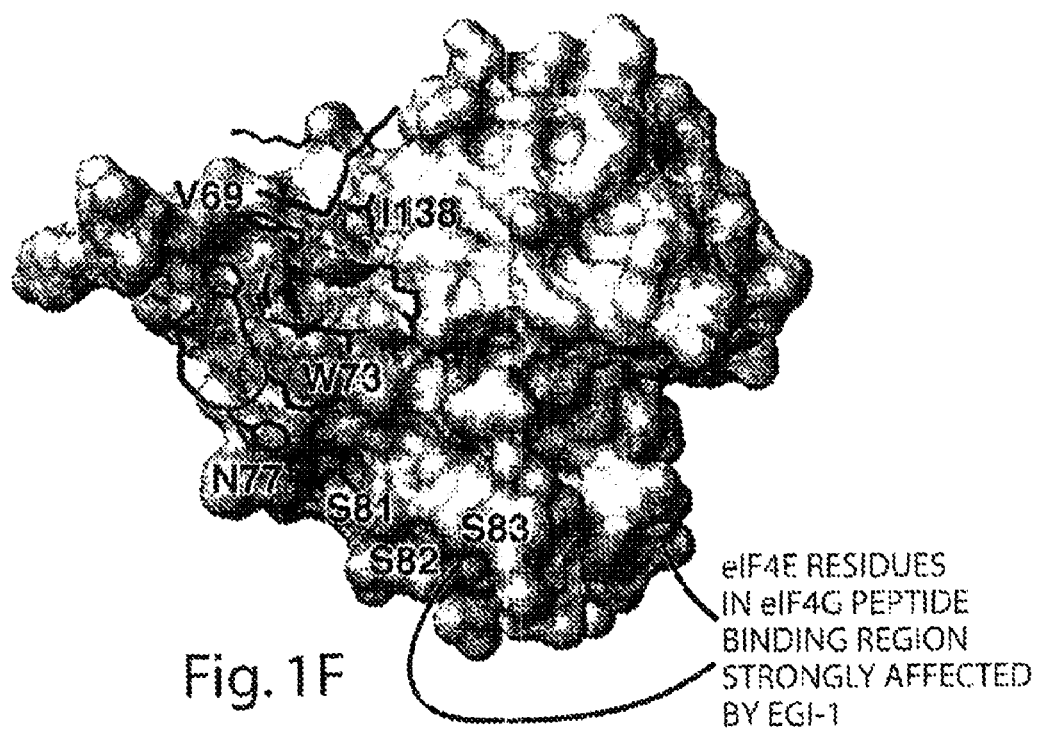
FIG. 1F is a schematic showing that EGI-1 interacts with the eIF4G recognition surface of eIF4E. The same structure as FIG. 1E is shown, with eIF4E residues in the eIF4G peptide binding region strongly affected by EGI-1 (shift in peak position or greater than 35% signal attenuation) labelled and shaded.
Figure 5C:
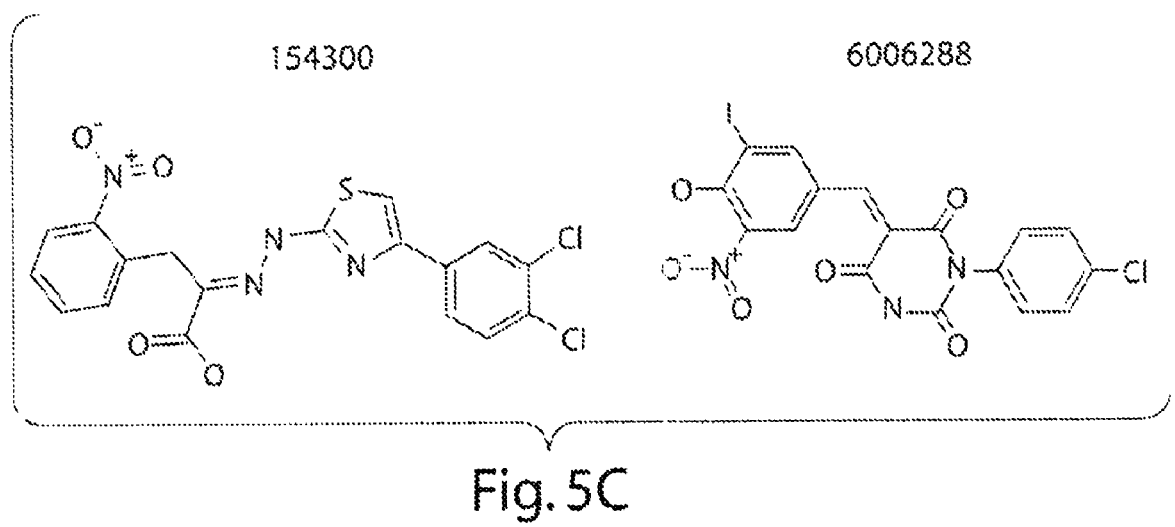
FIG. 5C is a diagram of the chemical structure of hit compounds, EGI-1 (compound 154300) and 6006288.
Figure 5D:
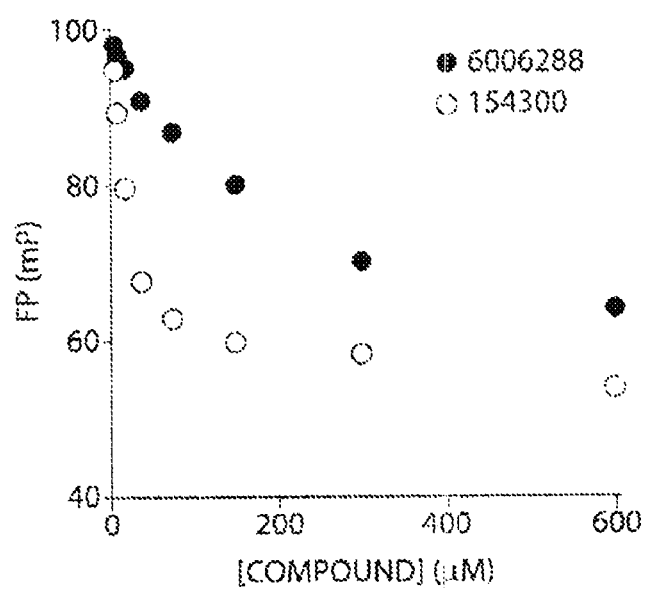
FIG. 5D is a dot plot showing inhibition of labeled peptide binding by hit compounds.

The assay was adapted to a microwell plate format and used to screen a number of libraries comprised of small molecule libraries for potential eIF4E/eIF4G interaction inhibitors. Because screens for inhibitors of protein-protein interactions typically have very low hit rates (on the order of 0.01-0.1%), the strategy taken was to carry out a large initial screen comprising the Chembridge Diverset E library (16,000 compounds), the Bionet library (4,800), the Maybridge library (8,800), the Peakdale library (2,816), and a portion of the Chembridge Microformat library for a total of 42,416 compounds. Two hit compounds with drug-like structures were selected from this screen for further characterization: EGI-1 (compound 154300) and 6006288 (FIG. 5C). FIG. 1D shows inhibition of labeled peptide binding for these two compounds: by comparison of the potency of inhibition to that of an eIF4G peptide of known binding affinity the affinities of these compounds are estimated at 1 uM for EGI-1 (compound 154300) and 10 uM for 6006288.

In order to structurally characterize the interaction of these compounds with eIF4E by NMR spectroscopy, the backbone N and H chemical shift assignment for the unbound form of mammalian eIF4E was determined. Although backbone assignments have been determined for the complex of mammalian eIF4E with an eIF4G peptide (Miura et al., 2003, J. Biomol. NMR 27(3): p. 279-80.30, the assignments for the free protein were determined in order to characterize its interaction with compounds binding to the peptide-binding surface. Because the poor solubility of free eIF4E makes it unsuitable for multidimensional NMR analysis, solubility was improved by constructing a fusion of this protein with the 56-residue GB1 domain of protein G. This domain has been found to act as a solubility enhancement tag for heterologous proteins to which it is fused. This construct has dramatically improved solubility and stability, and inspection of the HSQC spectra of the native and fusion proteins shows that the presence of this tag does not have any affect on the native structure of eIF4E.

Figure 6A:
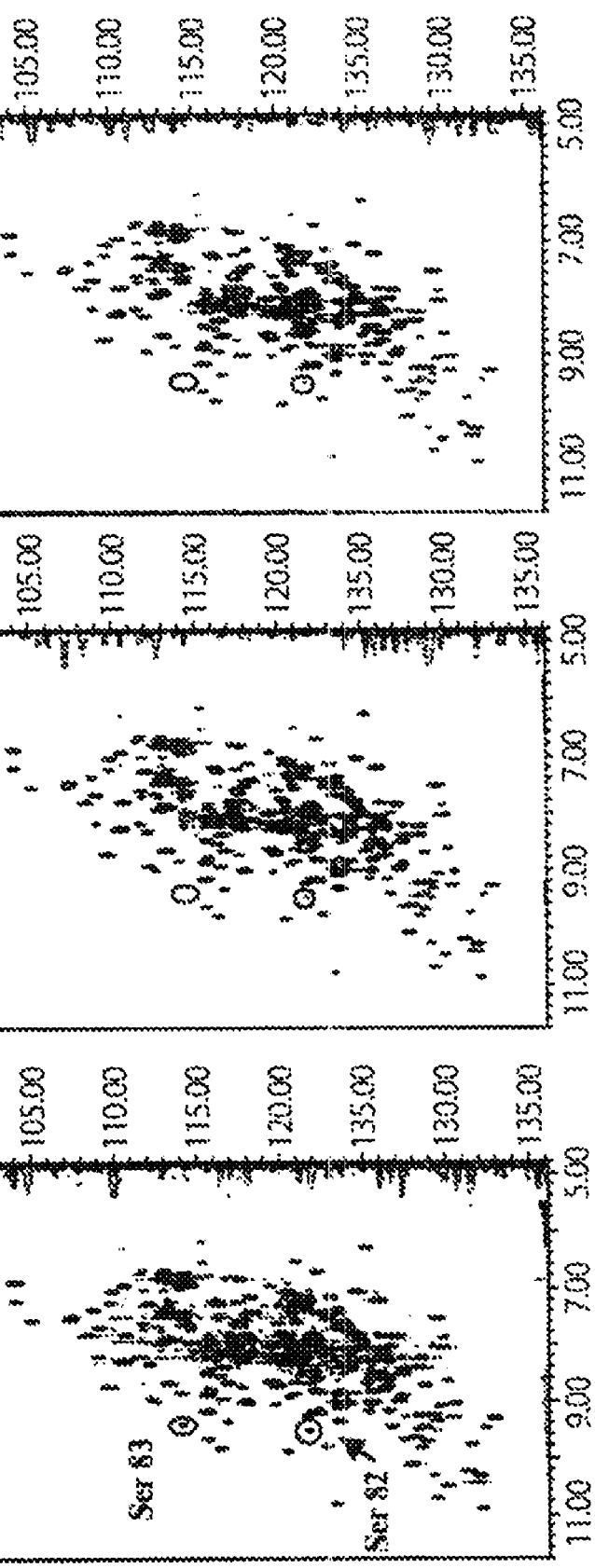
FIG. 6A is a series of graphs showing data from a titration of 50 μM eIF4E with EGI-1 (compound154300) using multidimensional NMR.
Figure 6B:
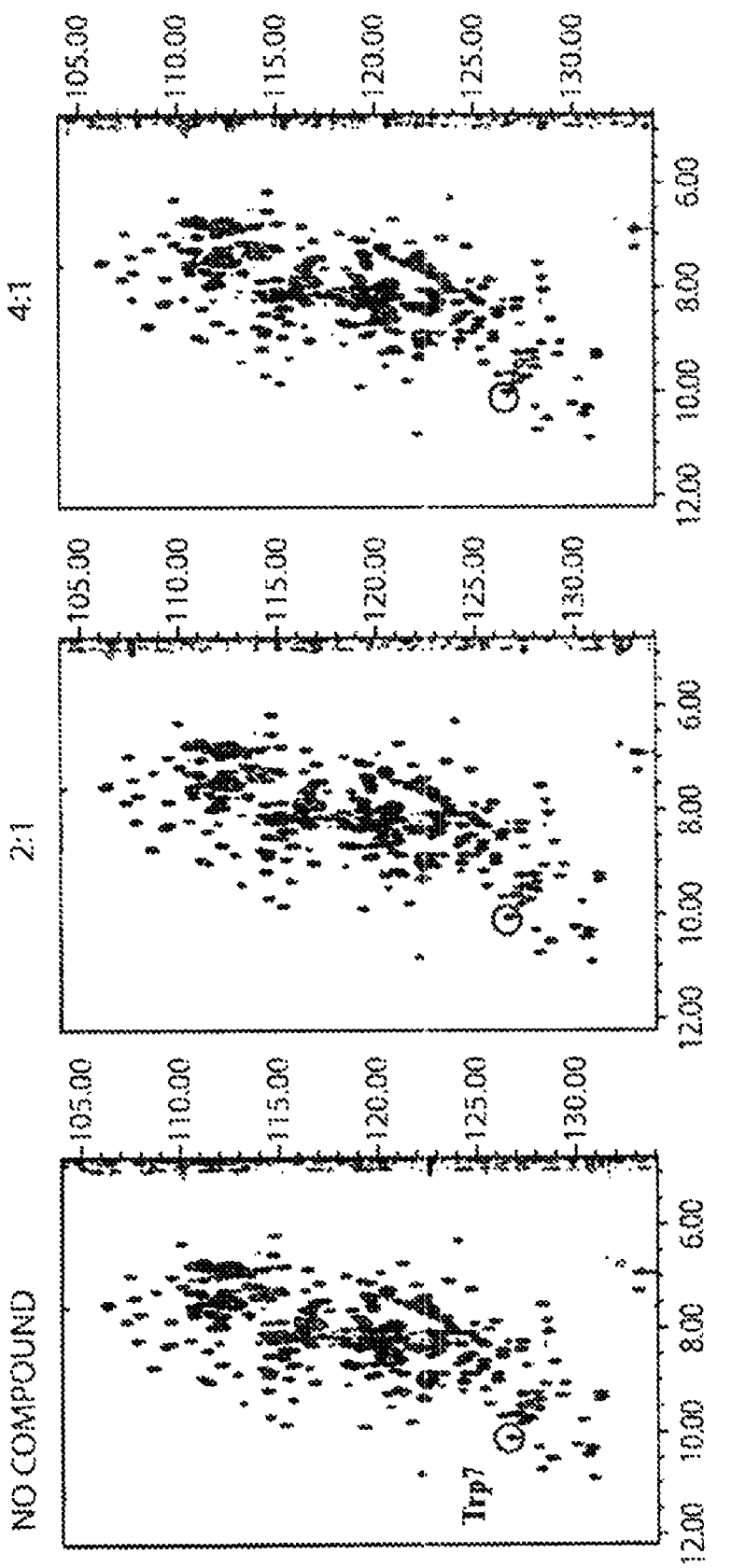
FIG. 6B is a series of graphs showing data from a titration of 50 μM eIF4E with compound 60062880 using multidimensional NMR.
Figure 6C:
FIG. 6C is a diagram of a docked model of EGI-1 (compound 154300) bound to eIF4E.

Using the GB1-meIF4E construct, 90% of the backbone assignments were determined using standard multidimensional NMR methods. HSQC titration experiments were carried out to confirm binding of compounds to eIF4E, map out the location of compound binding, and evaluate the specificity of compound binding. Titration of eIF4E with EGI-1 (compound 154300) (FIG. 6A) induced broadening of a number of peaks in the spectrum due to intermediate exchange between the ligand-bound and free states of the protein on the NMR time scale, which is consistent with relatively tight binding. The strongest broadening is that of the peaks corresponding to Ser82 and Ser 83, which are adjacent to the peptide binding site of eIF4E. Since a significant number of peaks are broadened in the spectrum it is possible that conformational change accompanies the binding of this compound. Titration with the compound 6006288 (FIG. 6B) induces a shift in the position of the side chain indole NH peak of Trp73, which is at the center of the peptide binding site of eIF4E. No other significant effects on the spectrum were observed. This shift indicated fast chemical exchange on the NMR time scale, which is consistent with the weaker binding of this compound.

Figure 7A:
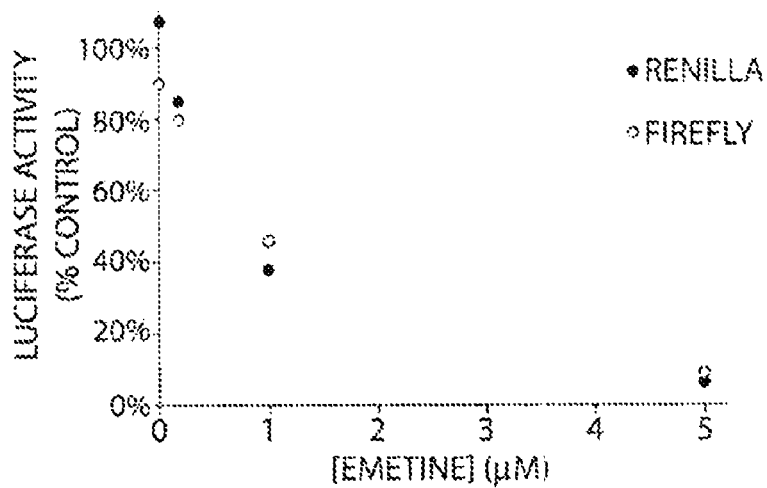
FIGS. 7A-C are a series of graphs showing the results of in vitro translation assays with in the presence of titrated concentrations (μM) of compounds.
Figure 7B:
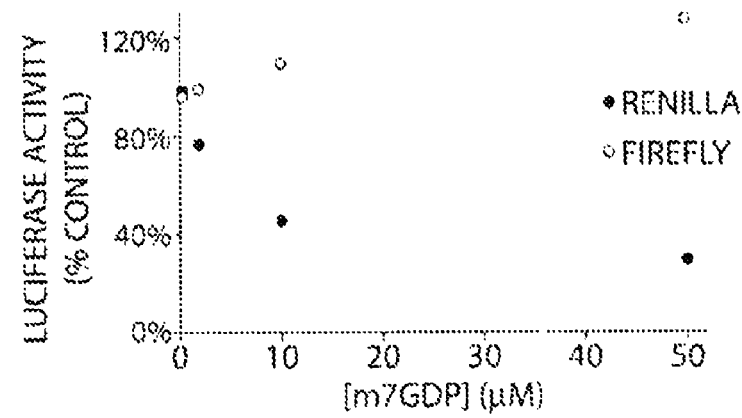
Figure 7C:
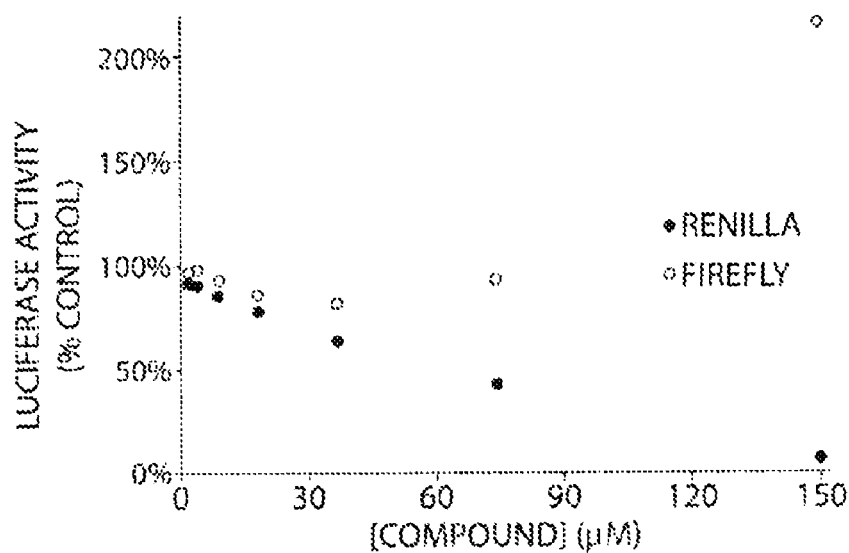

The information on the site of compound binding acquired by NMR provides a basis for modeling the binding of these molecules to eIF4E using computational methods. The program TreeDock (A. Fahmy, G. Wagner: TreeDock: A Tool for Protein Docking Based on Minimizing van der Waals Energies, J. Am. Chem. Soc., 124, 1241-1250 (2002)), predicts favorable conformations of a protein bound to a ligand by exhaustively docking the ligand in all possible orientations and using calculations of the Lennard-Jones potential to evaluate the free energy. The binding of EGI-1 (compound 154300) was modeled by running a TreeDock calculation with the compound restricted to being proximal to Ser82 and Ser83. This predicts that this compound can bind to the surface of eIF4E in a conformation that blocks the eIF4G peptide from binding. A representative low energy structure is shown in FIG. 7C.

In addition to structurally characterizing the binding of our hit compounds, biological activities of the compounds was evaluated. Based on the foregoing modeling, it was expected that a specific inhibitor of the eIF4E/4G interaction will inhibit cap-dependent translation of mRNA but should have no affect on cap-independent translation, such as from an IRES. To test this hypothesis in vitro, a translation assay in rabbit reticulocyte lysate was carried out. A dicistronic reporter construct containing a cap-dependent *Renilla* luciferase and a cricket paralysis virus IRES driven firefly luciferase was utilized to measure the relative affect of a compound on both translation mechanisms. To validate the assay it was demonstrated that emetine inhibits translation of both messages equally well (FIG. 7A) and m7GDP specifically inhibits the cap-dependent message (FIG. 7B). Titration of EGI-1 (compound 154300) in this assay inhibited translation of the cap-dependent luciferase but actually enhanced translation from the CrPV IRES (FIG. 7C). Thus, the compounds described herein selectively inhibit cap-dependent but not IRES-dependent translation. This enhancement was attributed to competition of the IRES with the capped 5' ends of the reporter and endogenous mRNAs for available ribosomes.

Figure 8A:
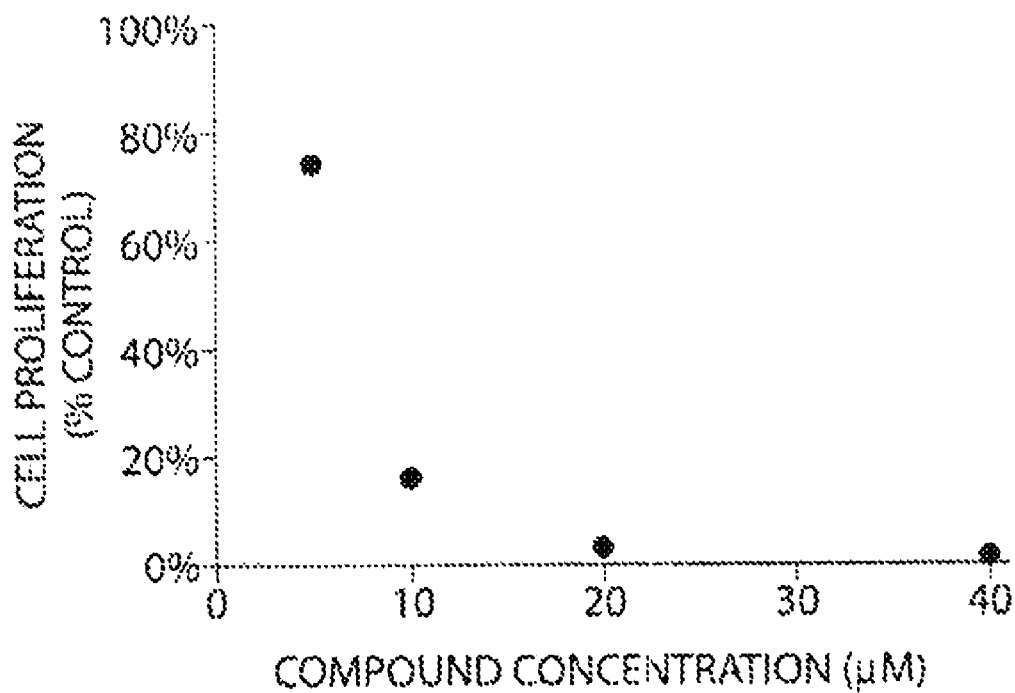
FIG. 8A is a graph showing the results of a proliferation assay using A549 cells in the presence of various concentrations (μM) of compound.
Figure 8B:
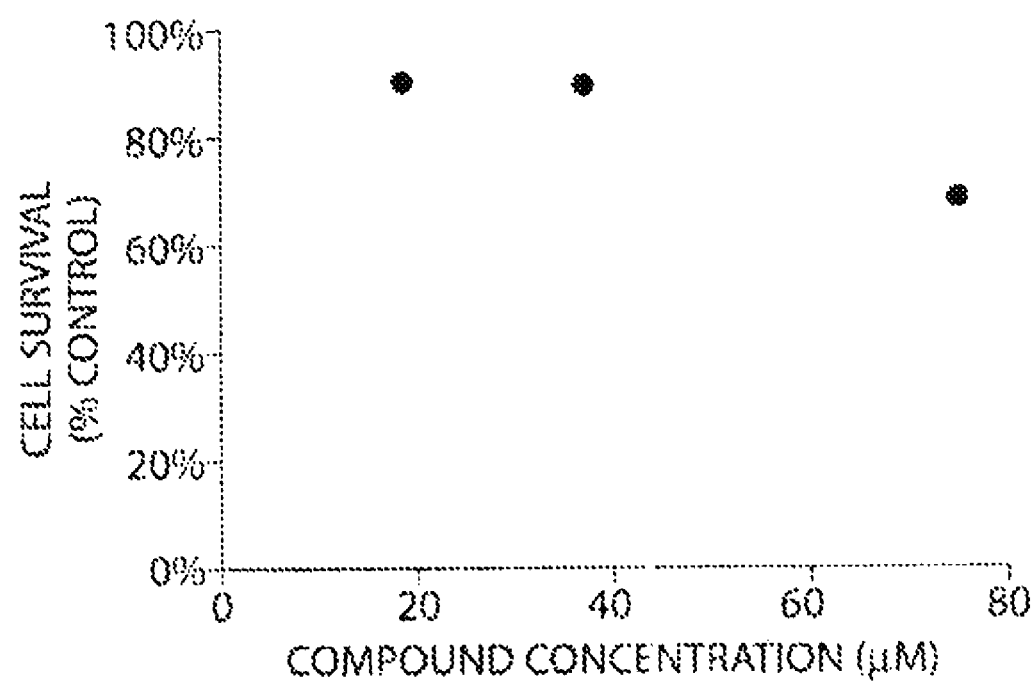
FIG. 8B is a graph showing the results of a survival assay using A549 cells in the presence of various concentrations (μM) of compound.
Figure 9:
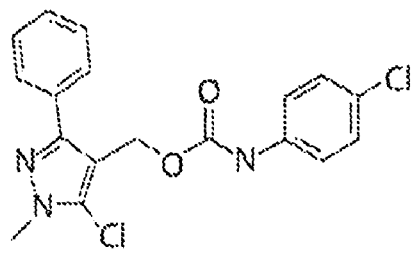
FIG. 9 is a series of diagrams showing the chemical structure of inhibitory compounds identified from Bionet, Peakdale and Maybridge Libraries (compounds 37629, 21573, 35197, 21551, and 29578).
Figure 9:
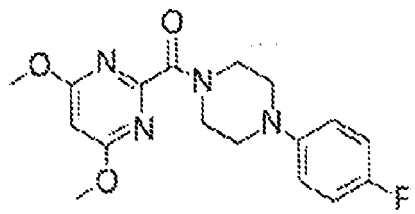
Figure 9:
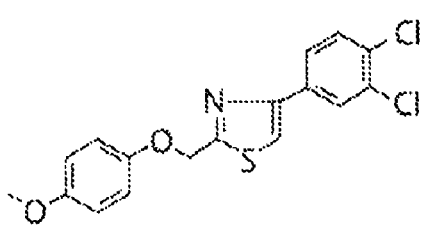
Figure 9:
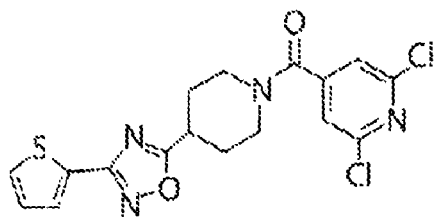
Figure 9:
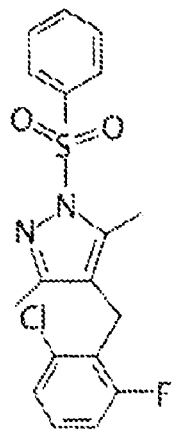
Figure 10:
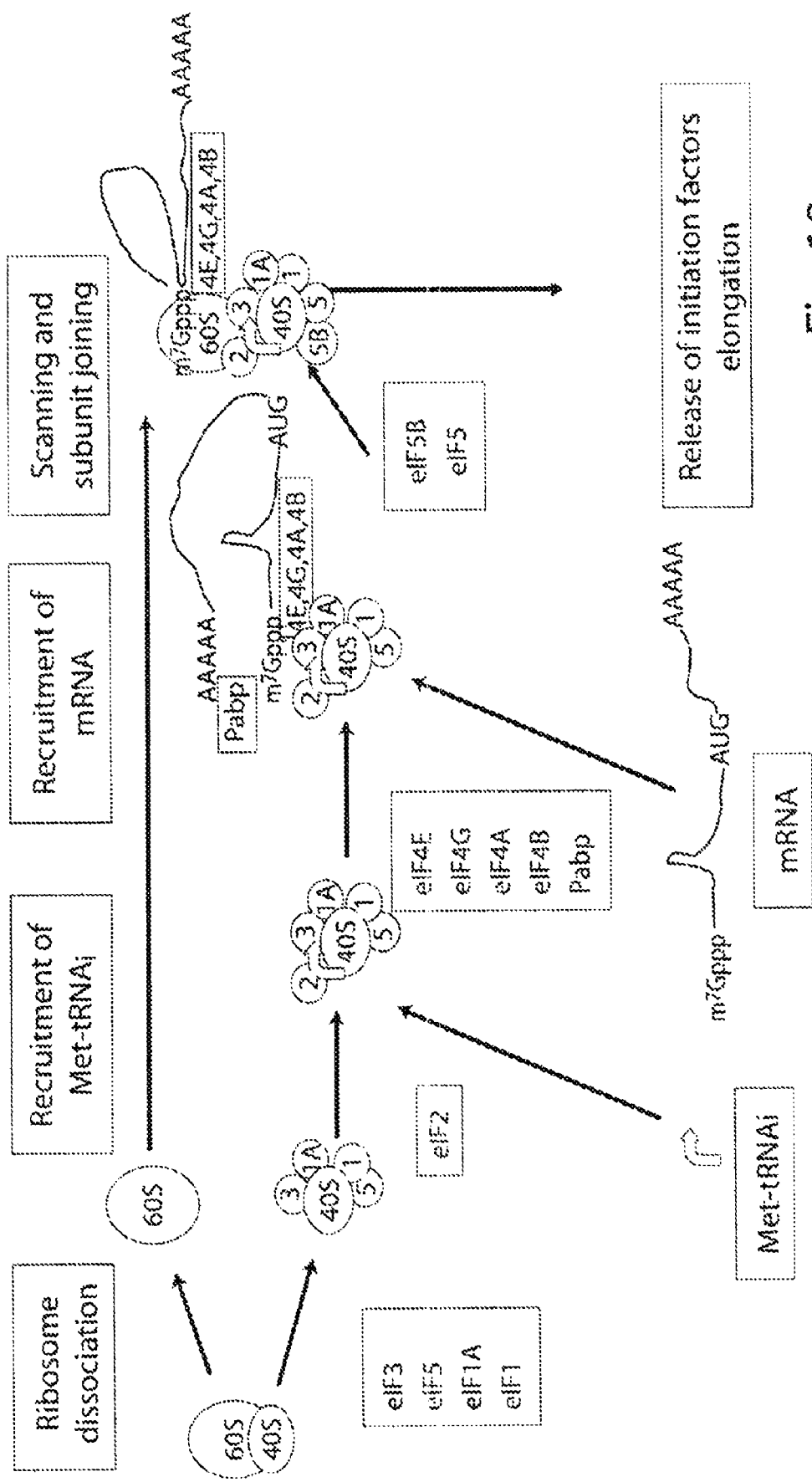
FIG. 10 is a diagram showing eukaryotic translation initiation.
Figure 11:
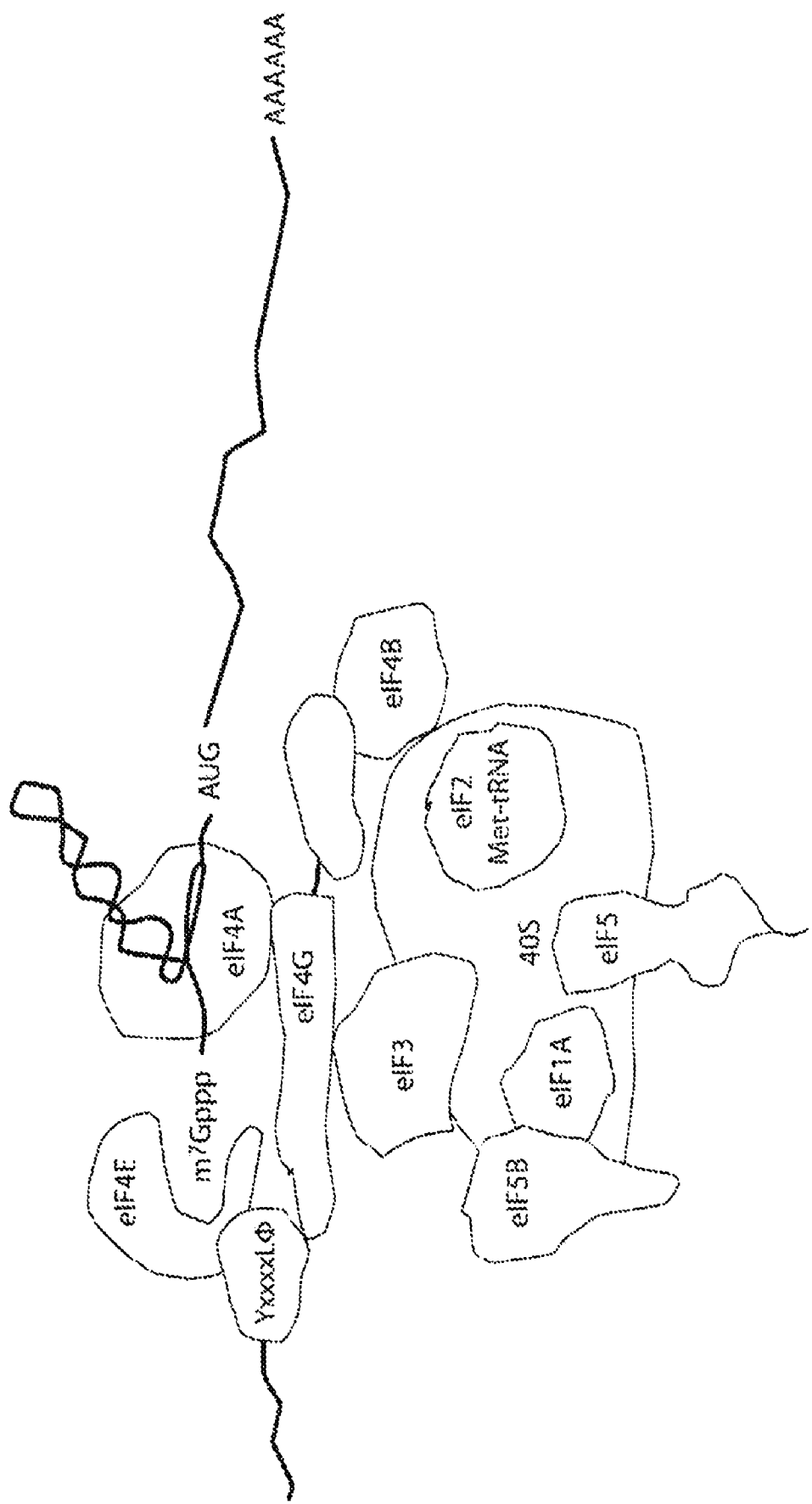
FIG. 11 is a diagram showing cap-dependent recruitment of mRNA to the 43S ribosomal subunit.
Figure 12:
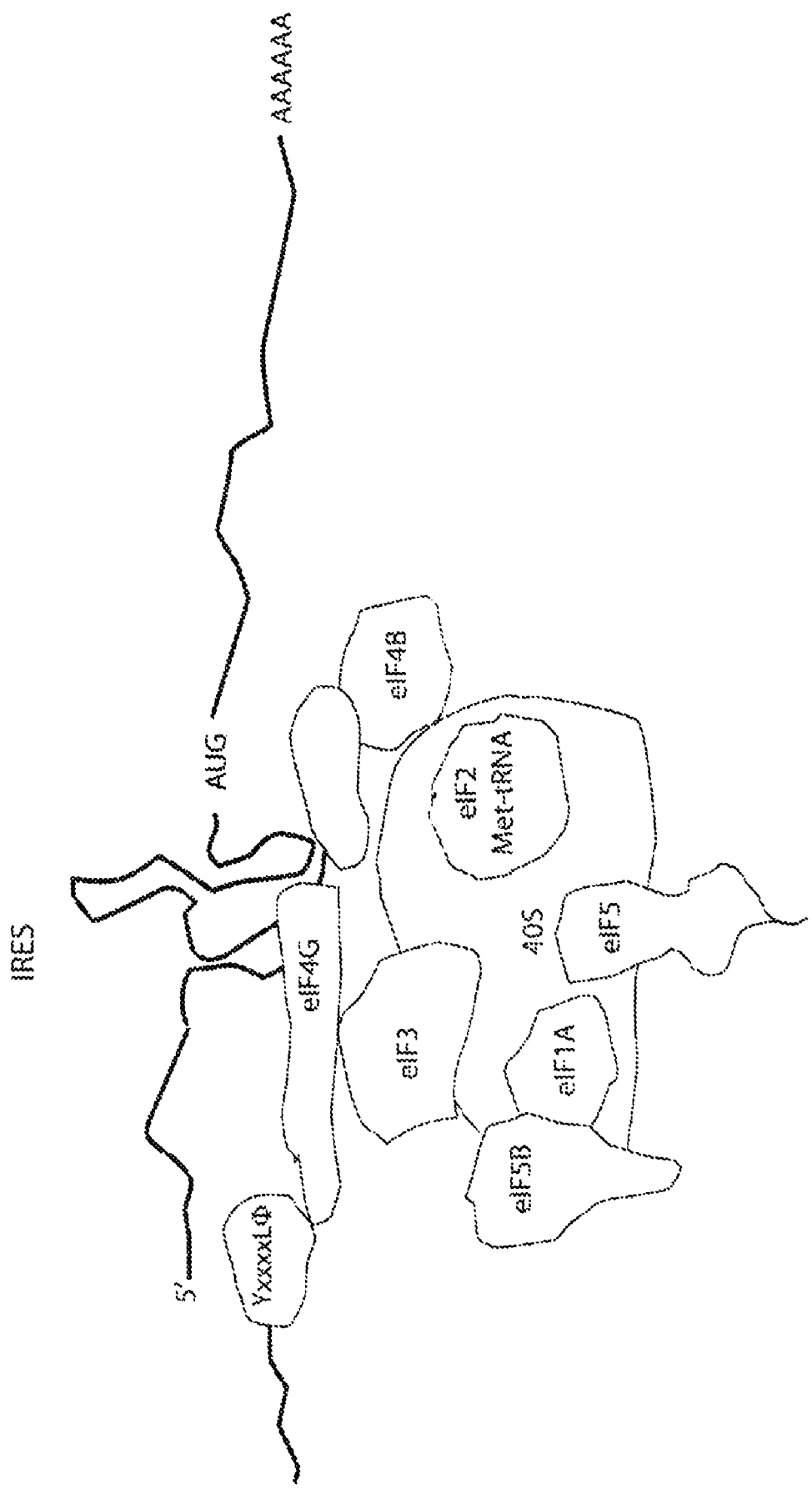
FIG. 12 is a diagram showing that translation can also be initiated via an internal ribosome entry site (IRES) in a cap-independent way. Housekeeping proteins such as eIF4G and some pro-apoptotic proteins such as Apaf-1 are synthesized via IRES-dependent initiation.
Figure 13:
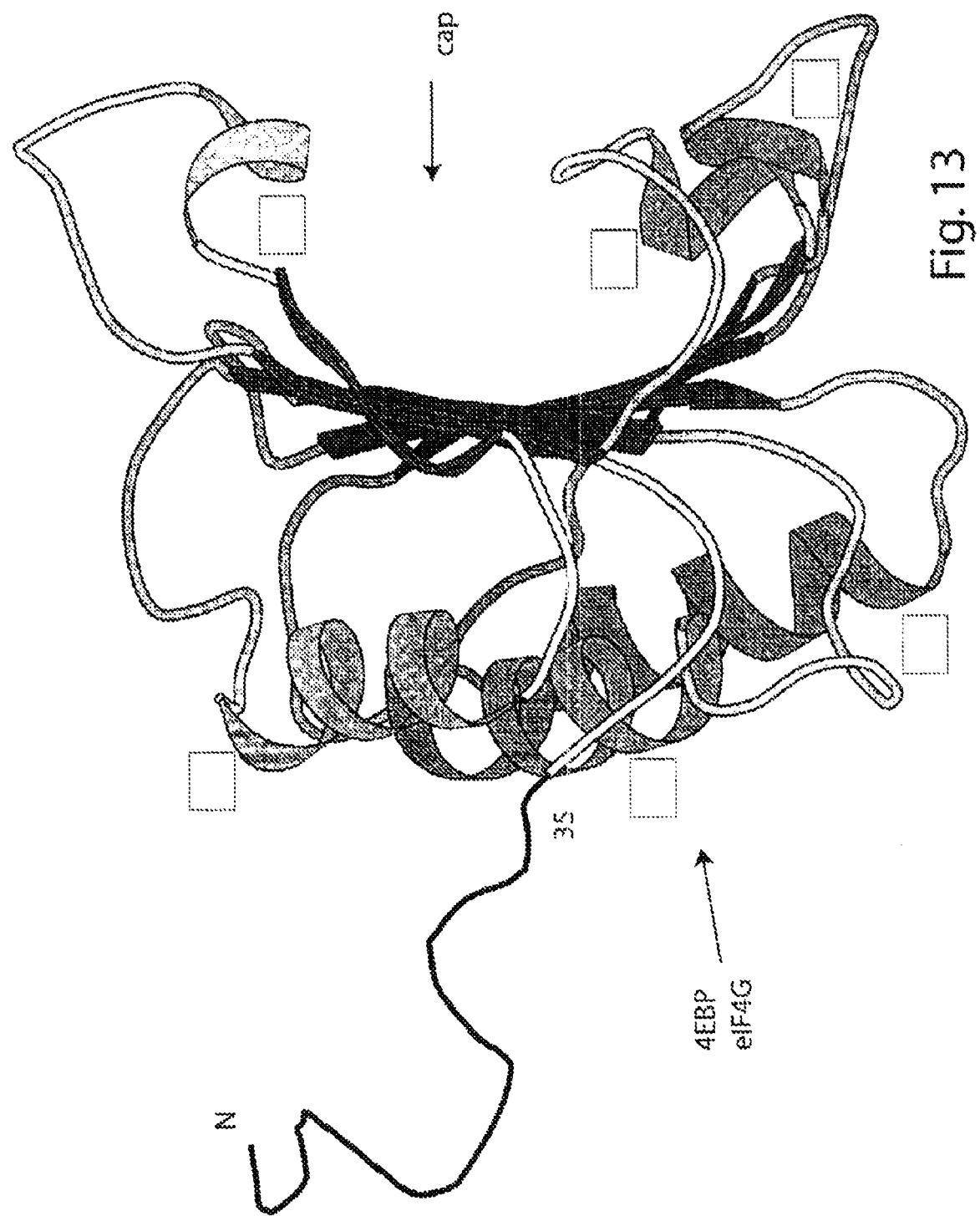
FIG. 13 is a diagram showing the structure of eIF4E.
Figure 14:
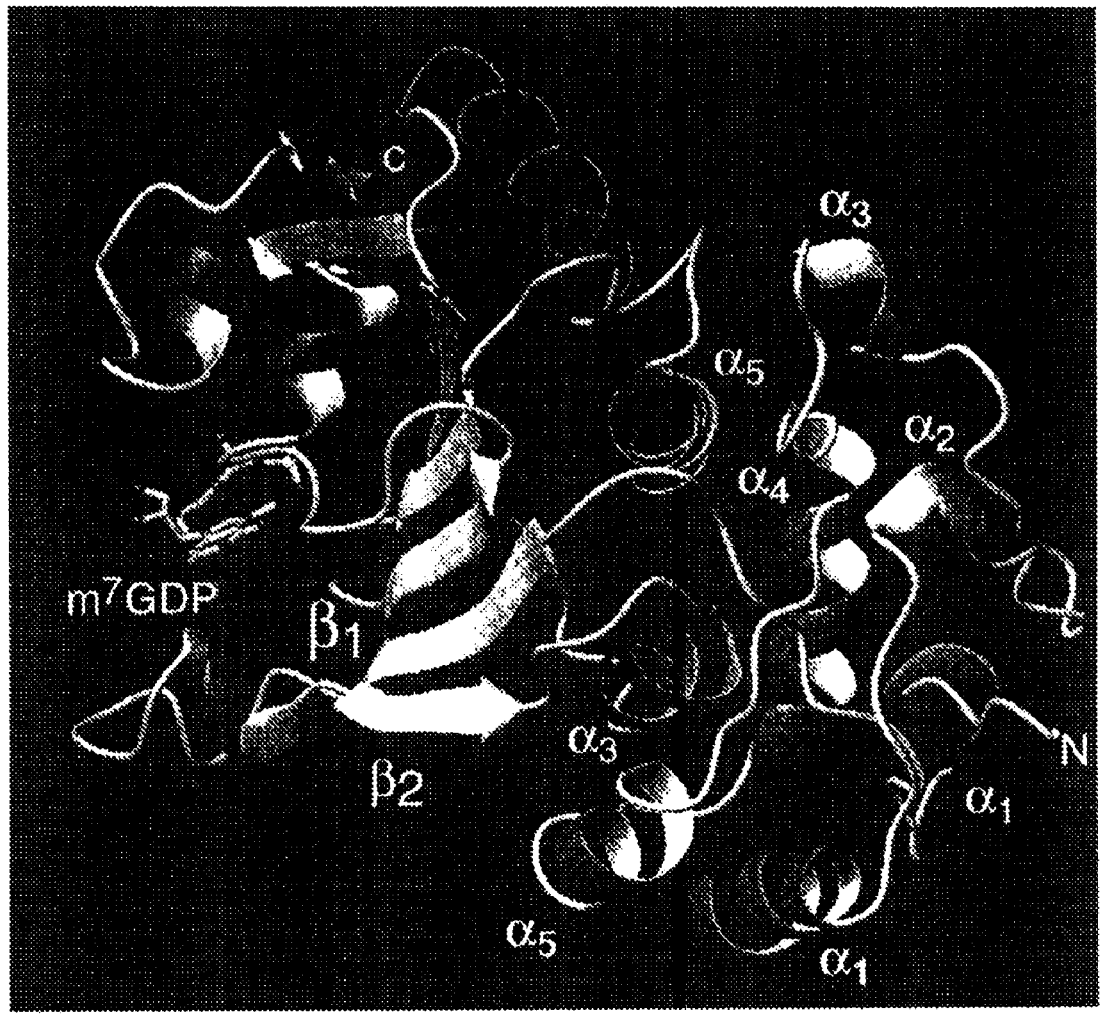
FIG. 14 is a diagram showing that eIF4G wraps around the N-terminus of eIF4E and triggers a mutual folding event.
Figure 15:
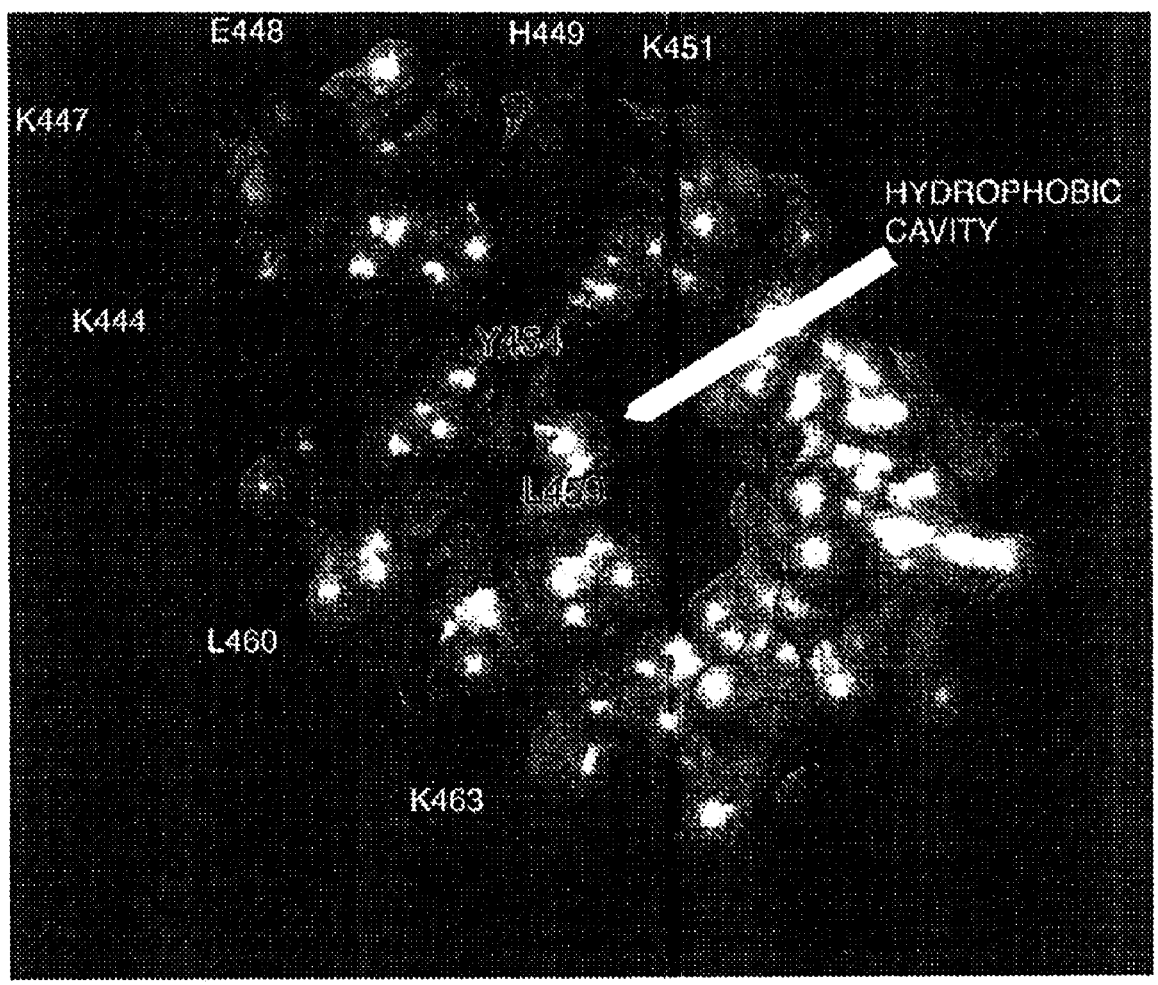
FIG. 15 is a diagram showing the eIF4E binding interface of eIF4G (393-490). eIF4G (393-490) does not form a globular structure.
Figure 16:
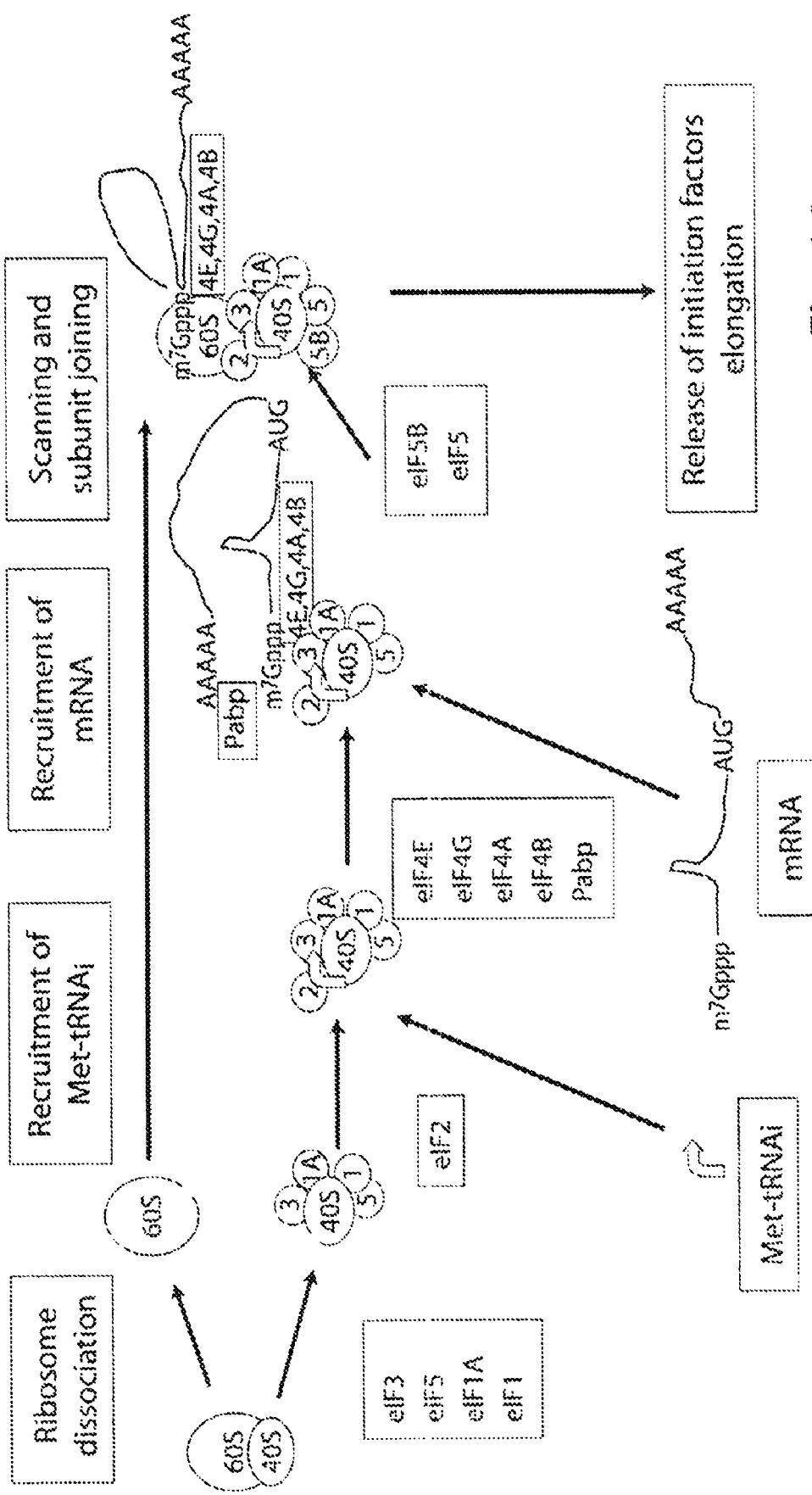
FIG. 16 is a diagram showing eukaryotic translation initiation.
Figure 17:
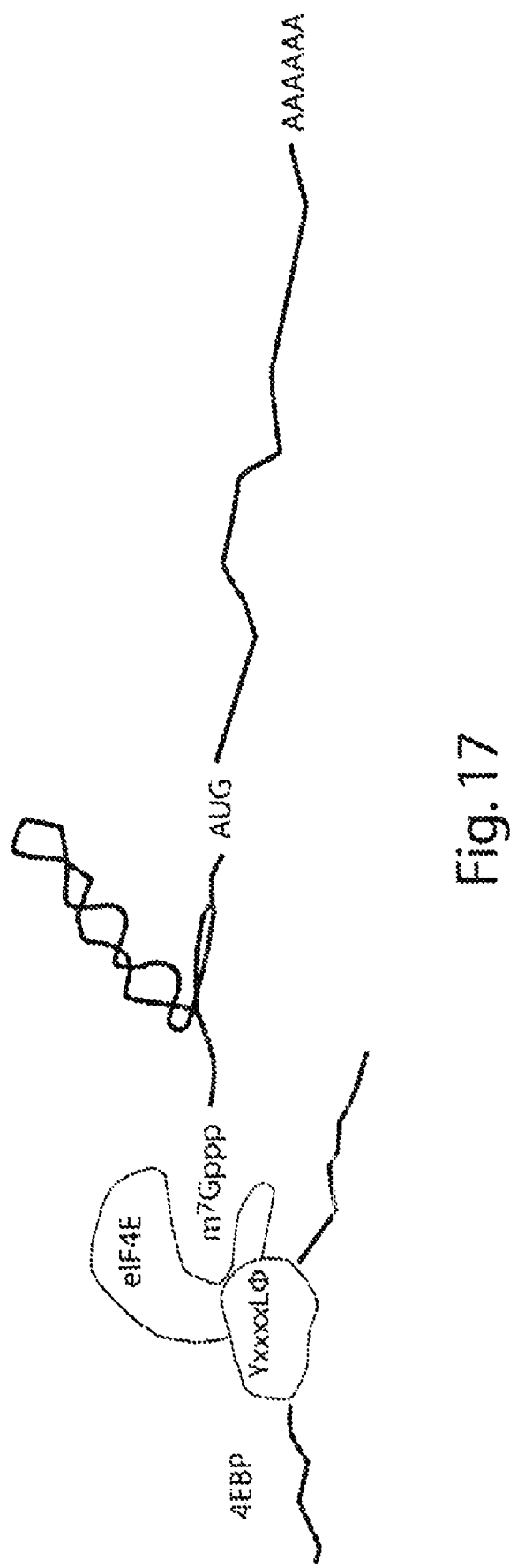
FIG. 17 is a diagram showing that cap-dependent initiation is down-regulated by 4E-binding proteins (4EBPs). 4EBPs inhibit recruitment of 43S ribosome by blocking eIF4G-binding site. 4EBPs shared the YxxxxLΦ consensus sequence with eIF4G.
Figure 18A:
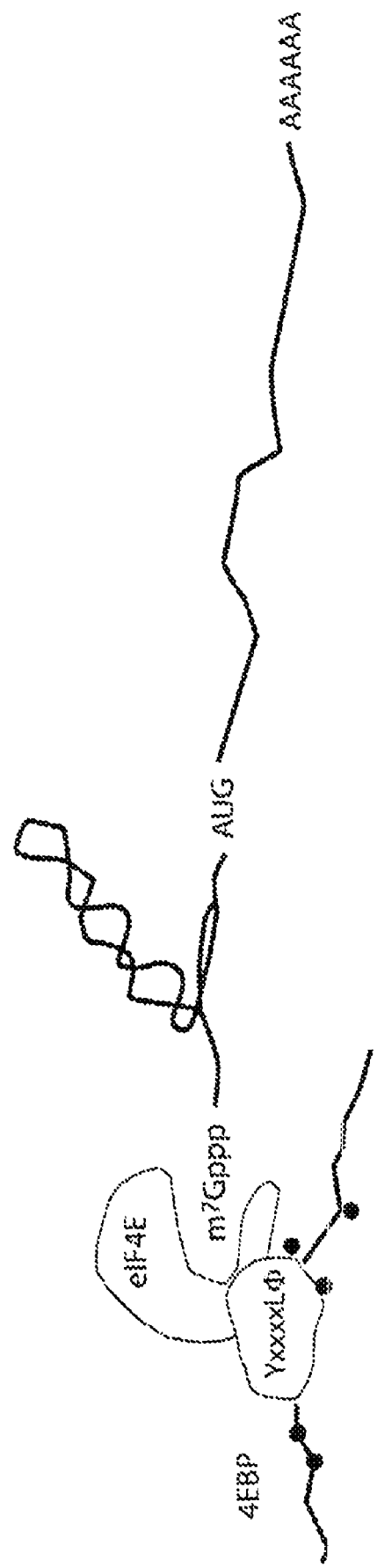
FIGS. 18A and 18B are diagrams showing that hyperphosphorylation of eIF4E-bound 4EBP (mTOR and PI3K) leads to dissociation of 4EBP and initiation.
Figure 18B:
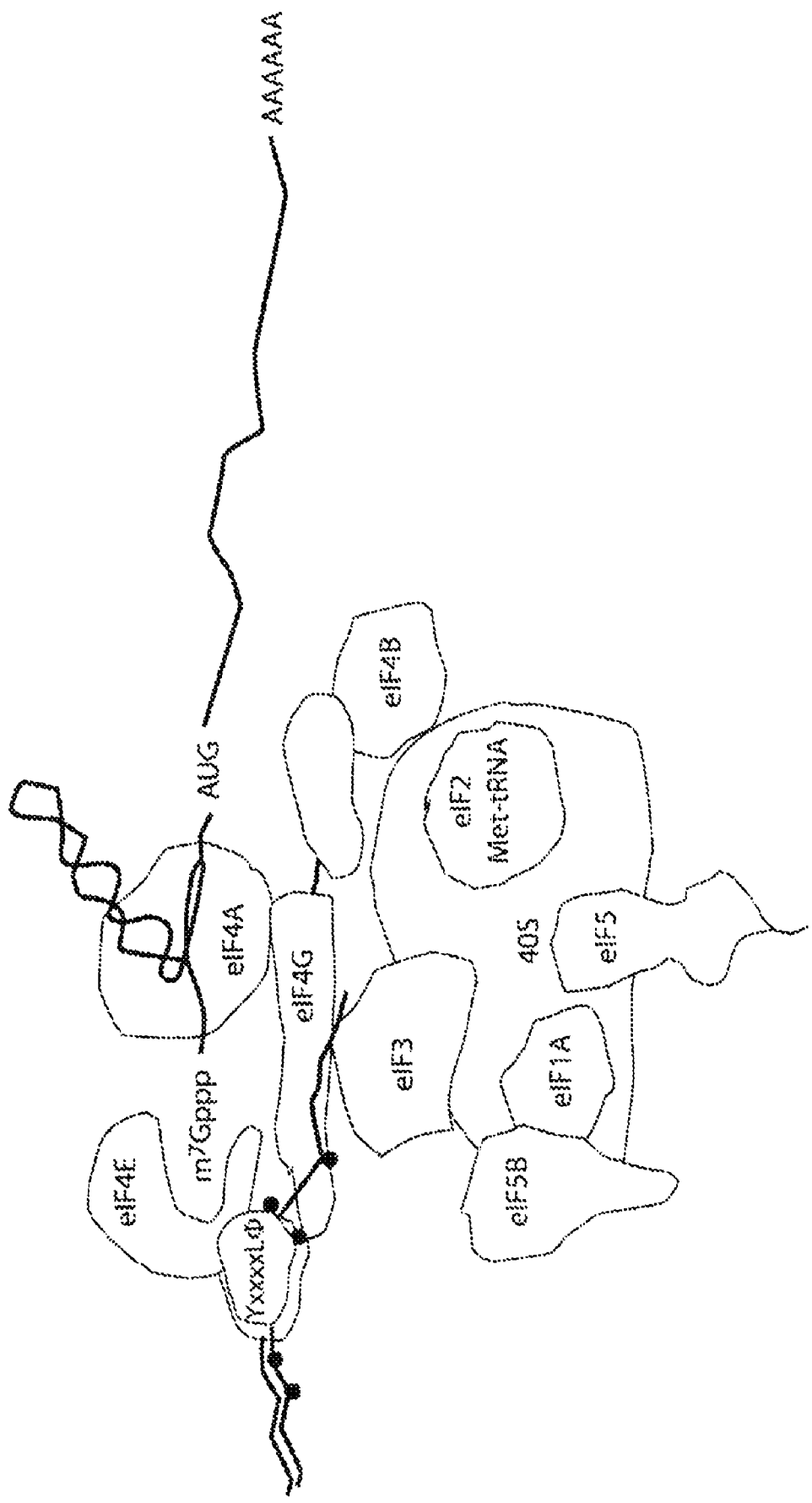
Figure 19:
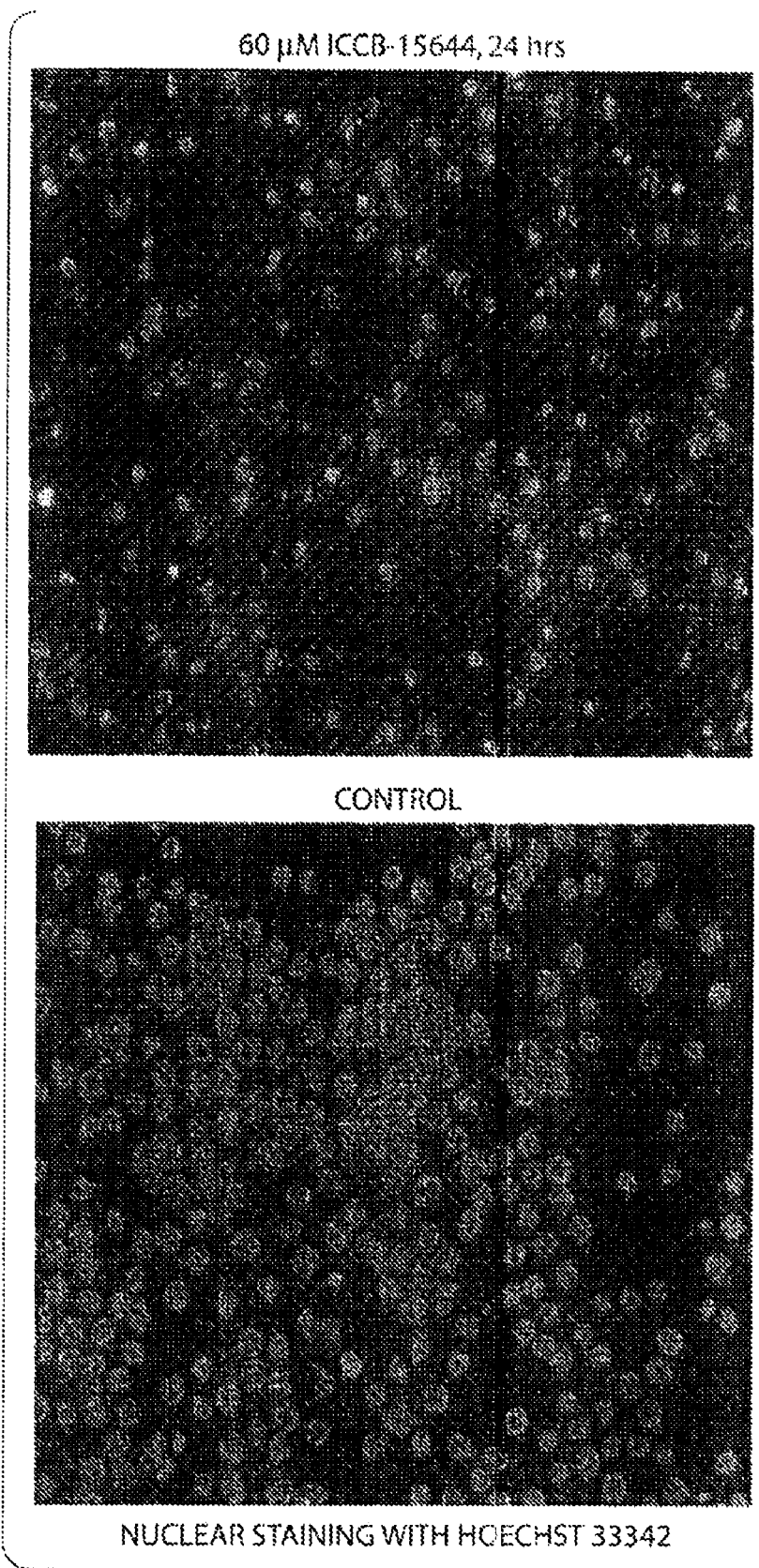
FIG. 19 is a series of photographs showing nuclear staining with Hoechst 33342. The addition of a 4E/4G inhibitor causes apoptosis in Jurkat cells.
Figure 20:
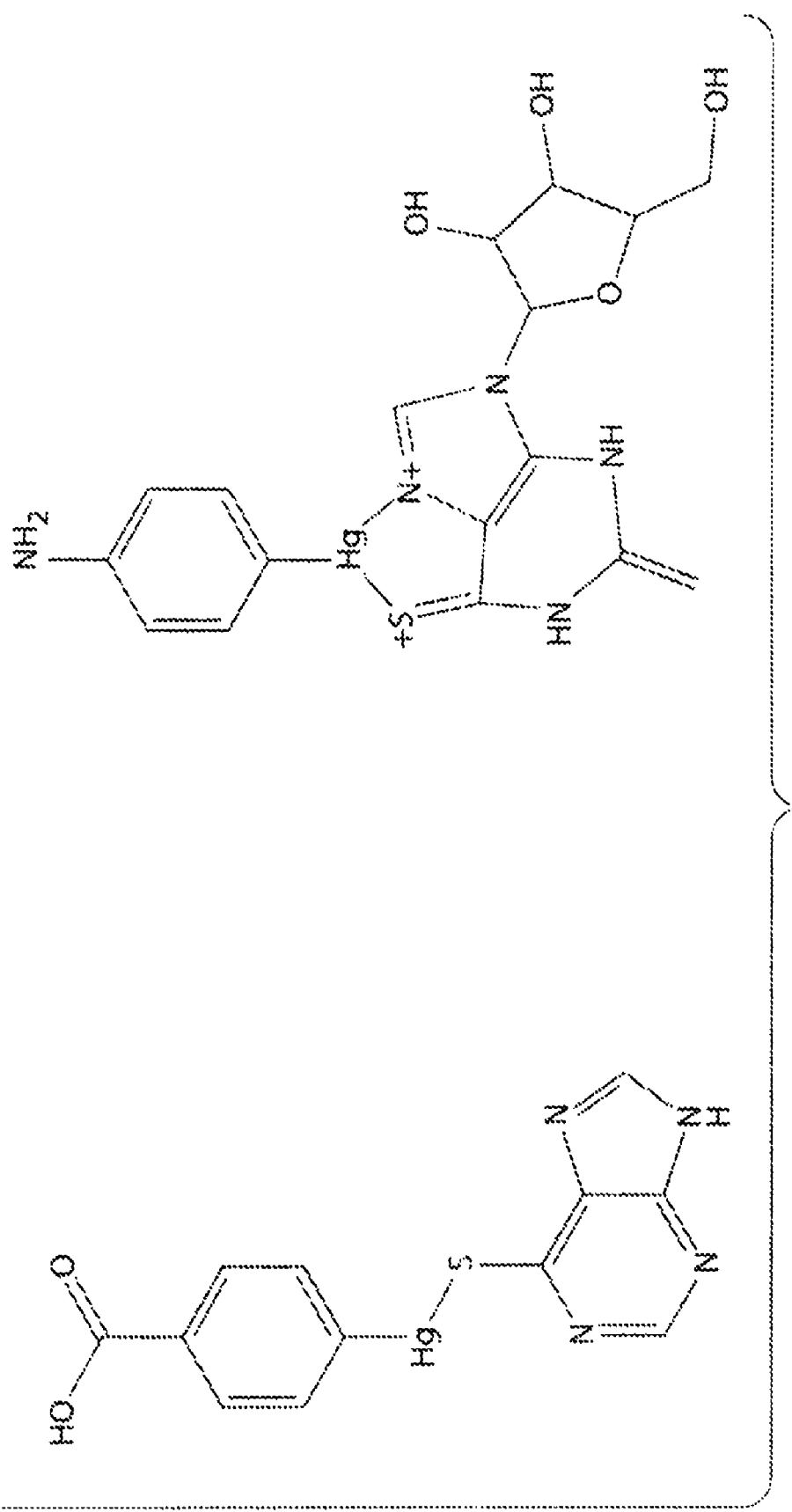
FIG. 20 is a diagram showing the chemical structure of active compounds from NCI diversity library.
Figures 21A, 21B:
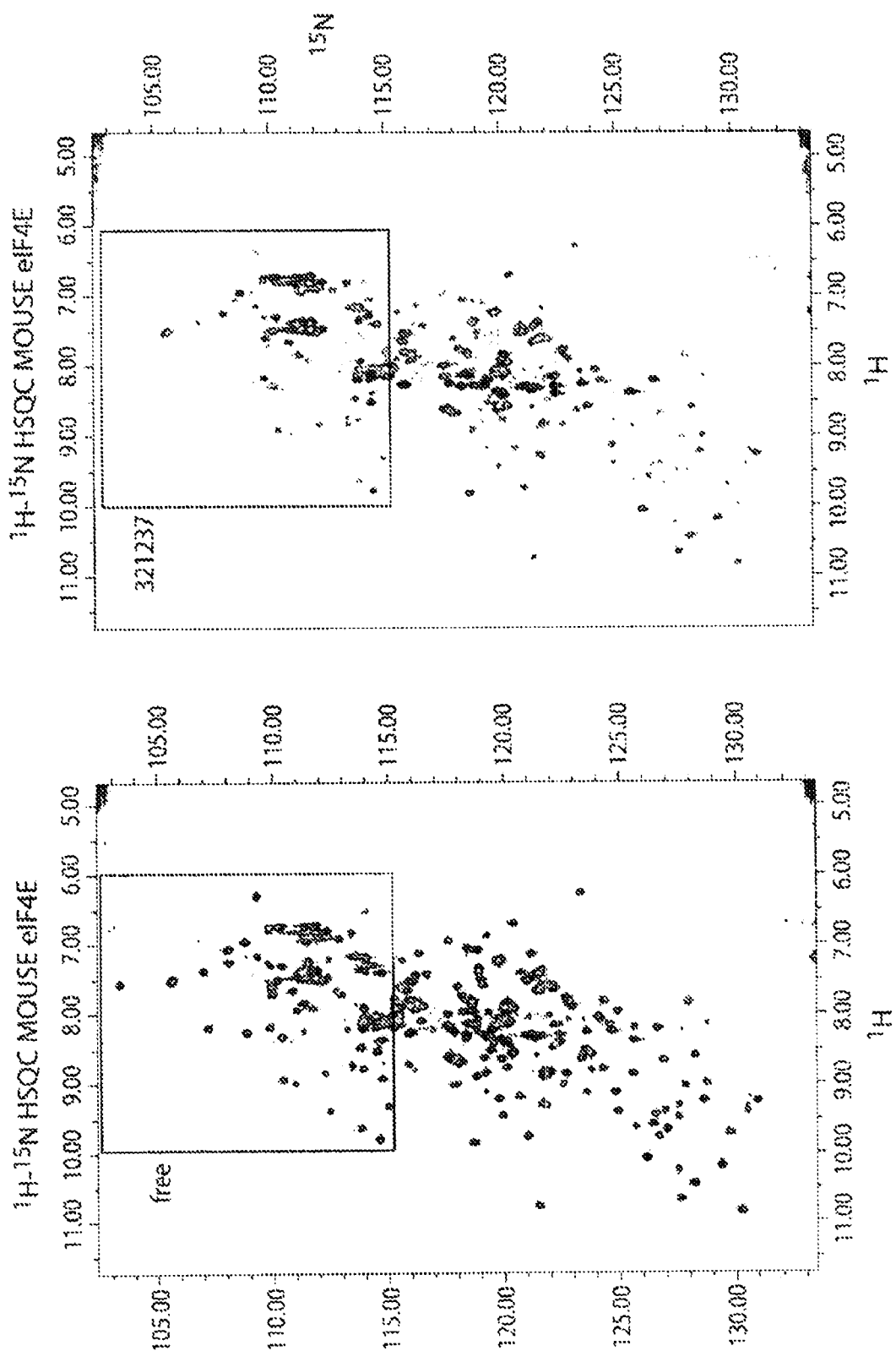
FIGS. 21A-21D are graphs showing $^1$H-15N HSQC mouse eIF4E
Figure 21D:
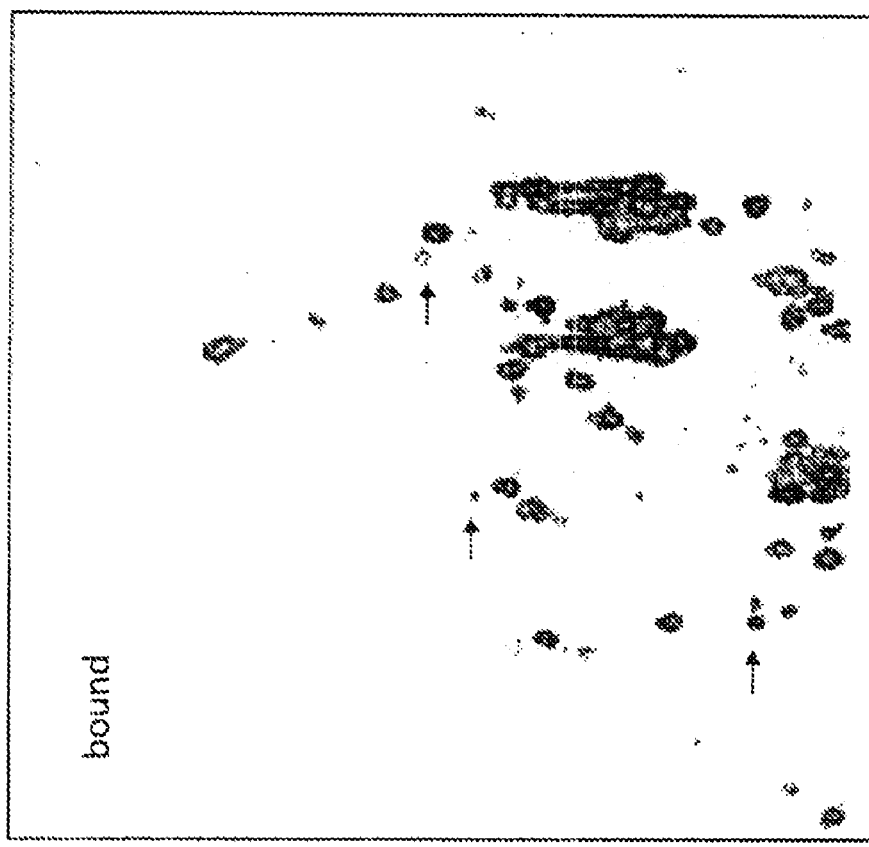
Figure 21C:
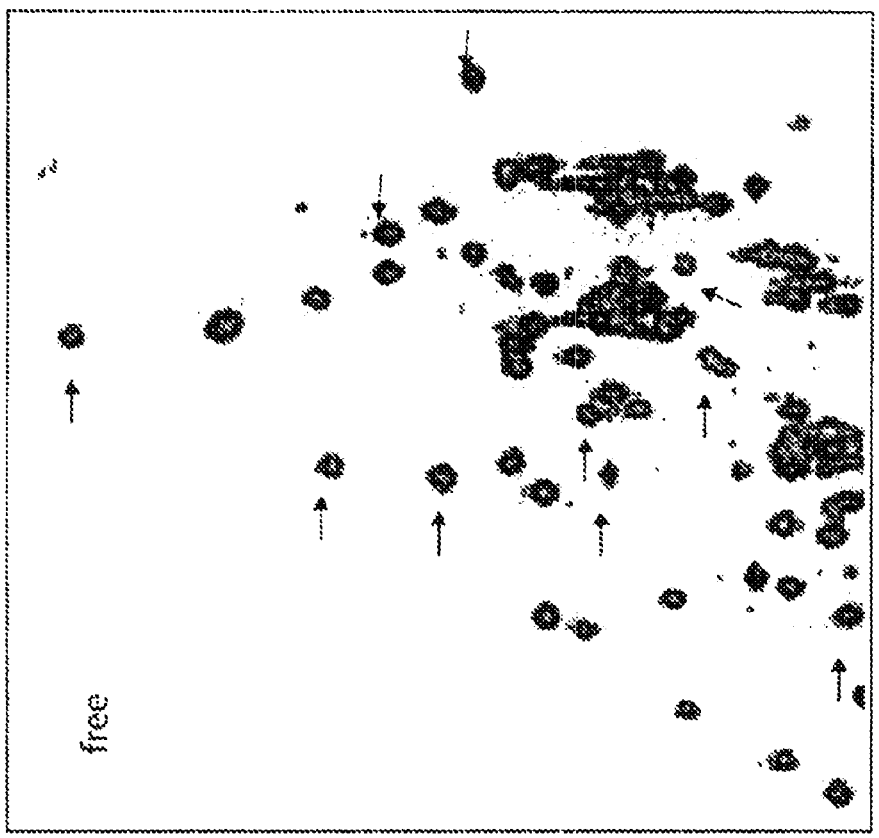
Figure 22:
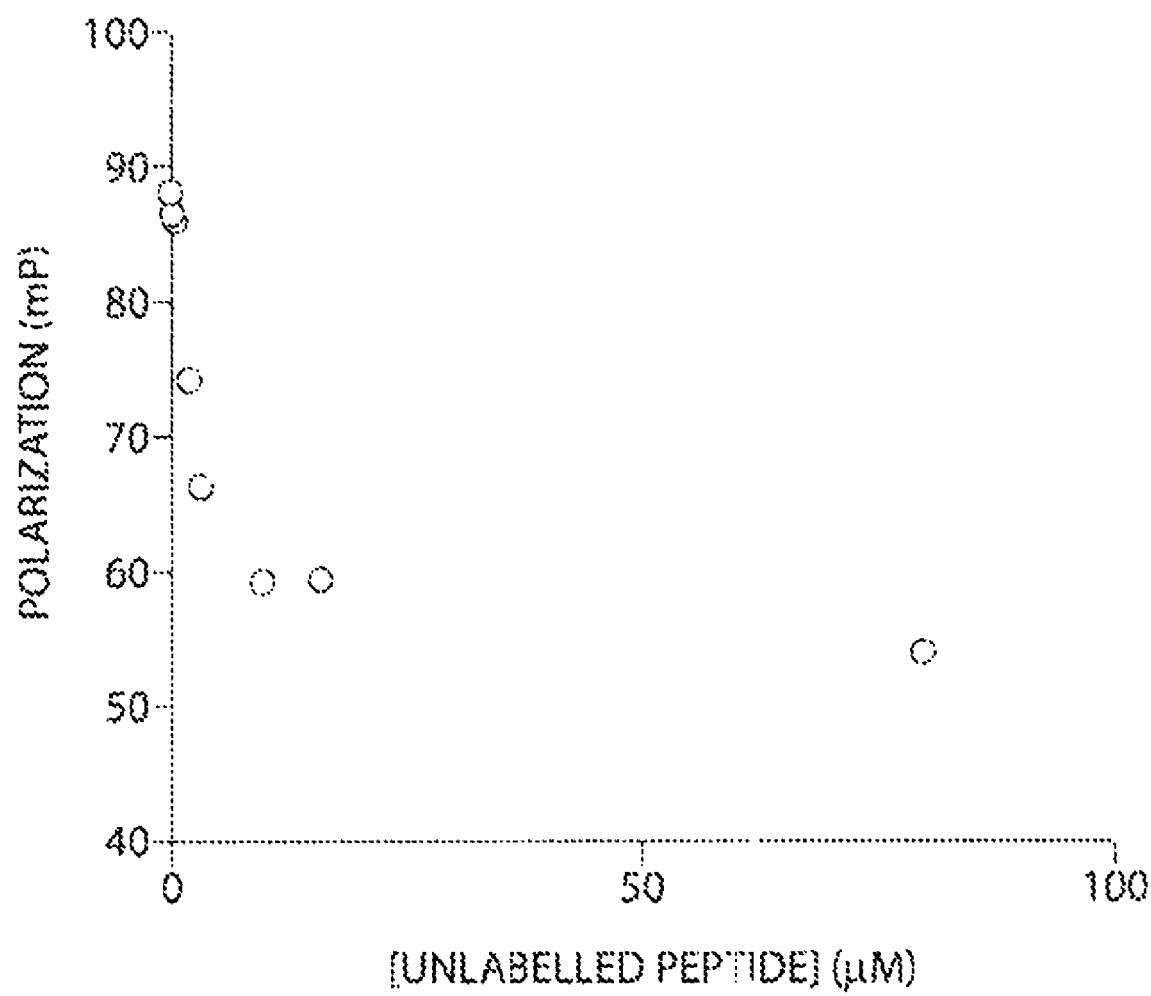
FIG. 22 is a graph showing FP of labeled peptide decreases back to baseline level upon the addition of unlabelled eIF4G peptide. Potential inhibitors of eIF4G binding to eIF4E are identified based on loss of fluorescence polarization.
Figure 23:
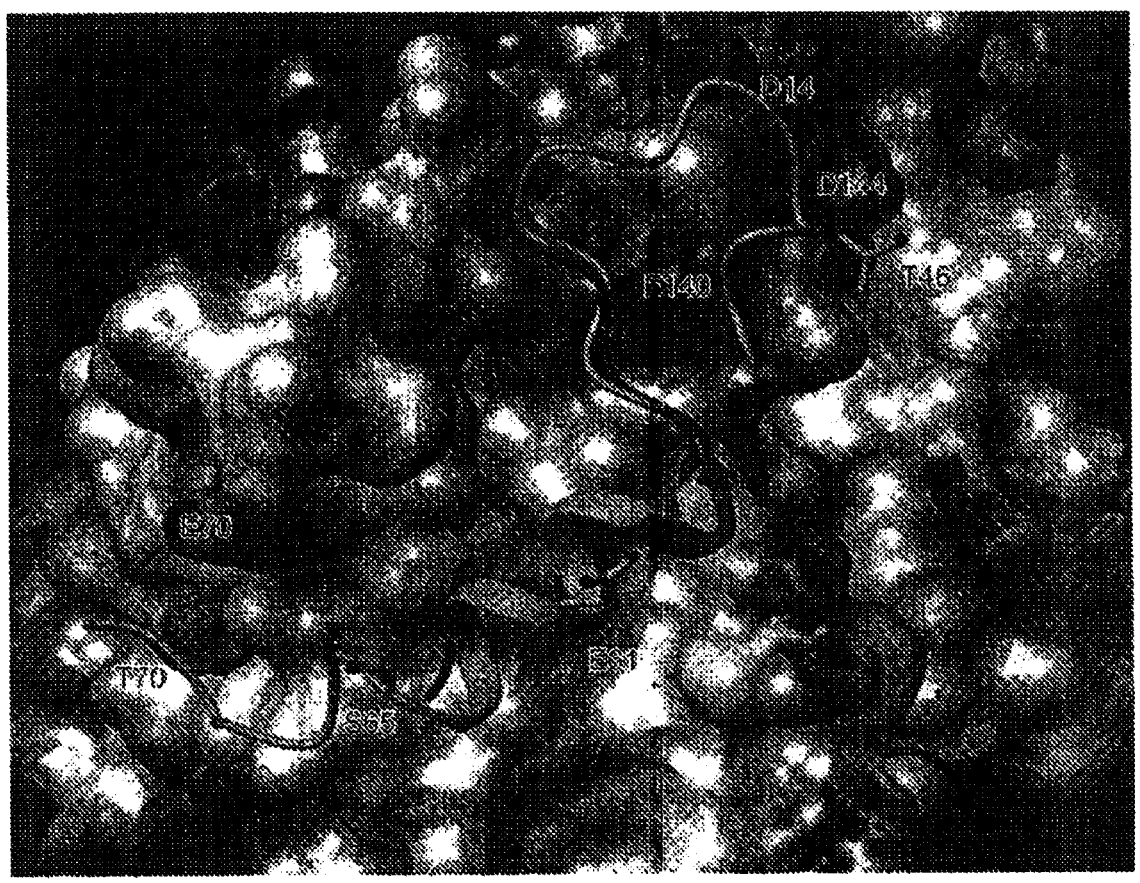
FIG. 23 is a diagram showing the eIF4E/4E-BP homology model. Small chemicals block binding of endogenous 4EBPs to eIF4E.
Figure 24:
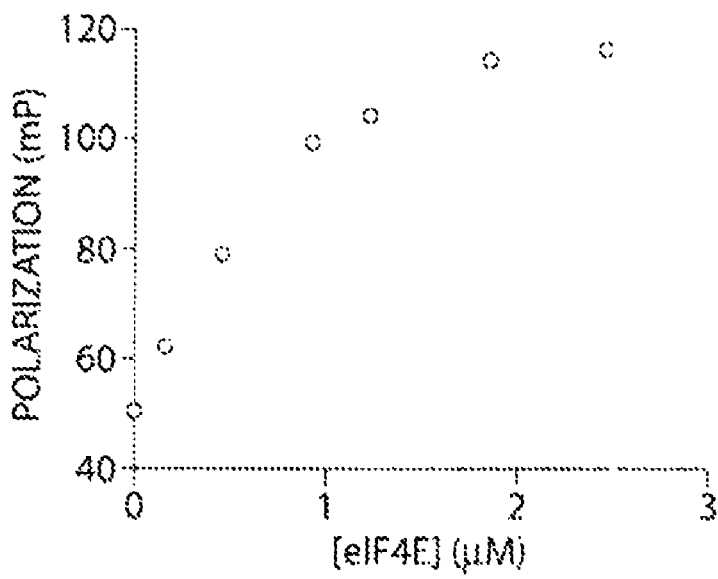
FIG. 24 is a graph showing design of fluorescence polarization assay. A peptide containing binding motif was synthesized with fluorescent label: KYTYDELFQLK-Fluorescein (SEQ ID NO:2). Addition of eIF4E to the peptide causes increased FP.
Figure 25:
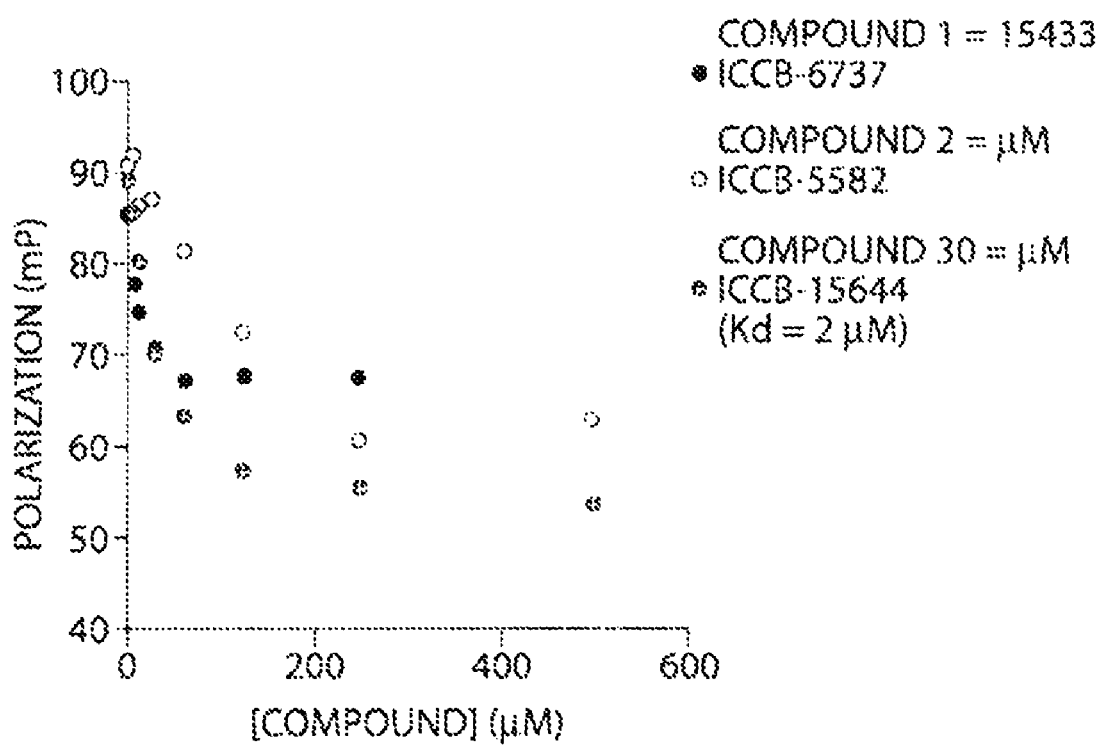
FIG. 25 is a graph showing inhibition of peptide binding by ICCB compounds.
Figure 26:
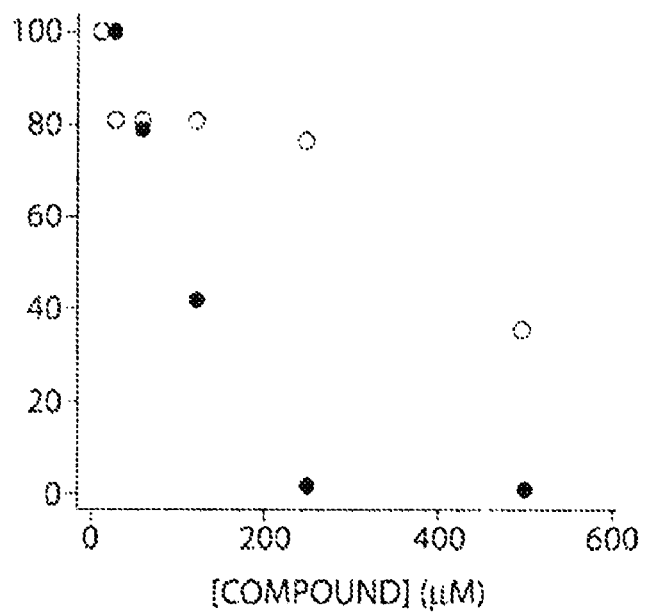
FIG. 26 is a graph showing inhibition of in vitro translation by ICCB compounds.
Figure 27:
FIG. 27 is a diagram showing a reporter gene to be used in a bicistronic translation assay.
Figure 28:
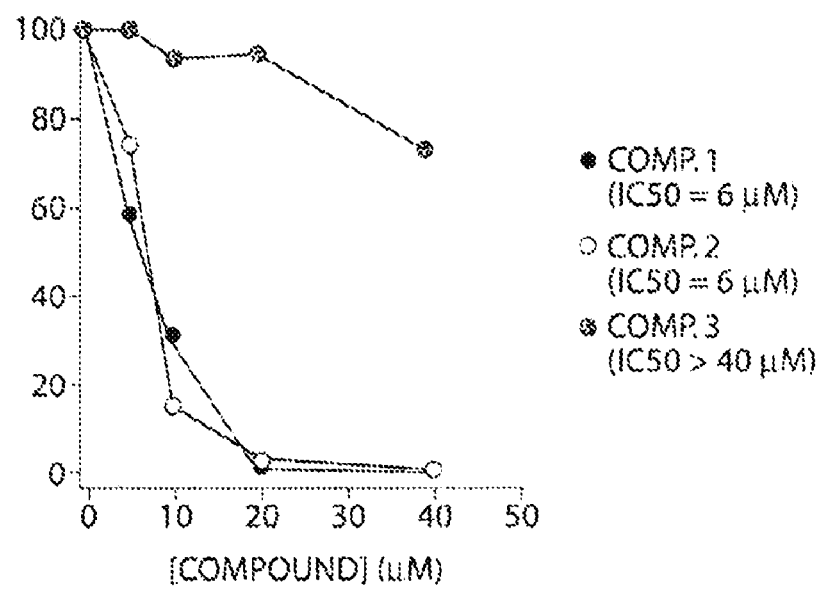
FIG. 28 is a graph showing the results of a cell proliferation assay. A549 cells, which are human lung cancer cells, are grown in plates for five days in medium containing 5% FCS and compound. The number of cells is quantified by staining with sulforhodamine B.
Figures 29A, 29B:
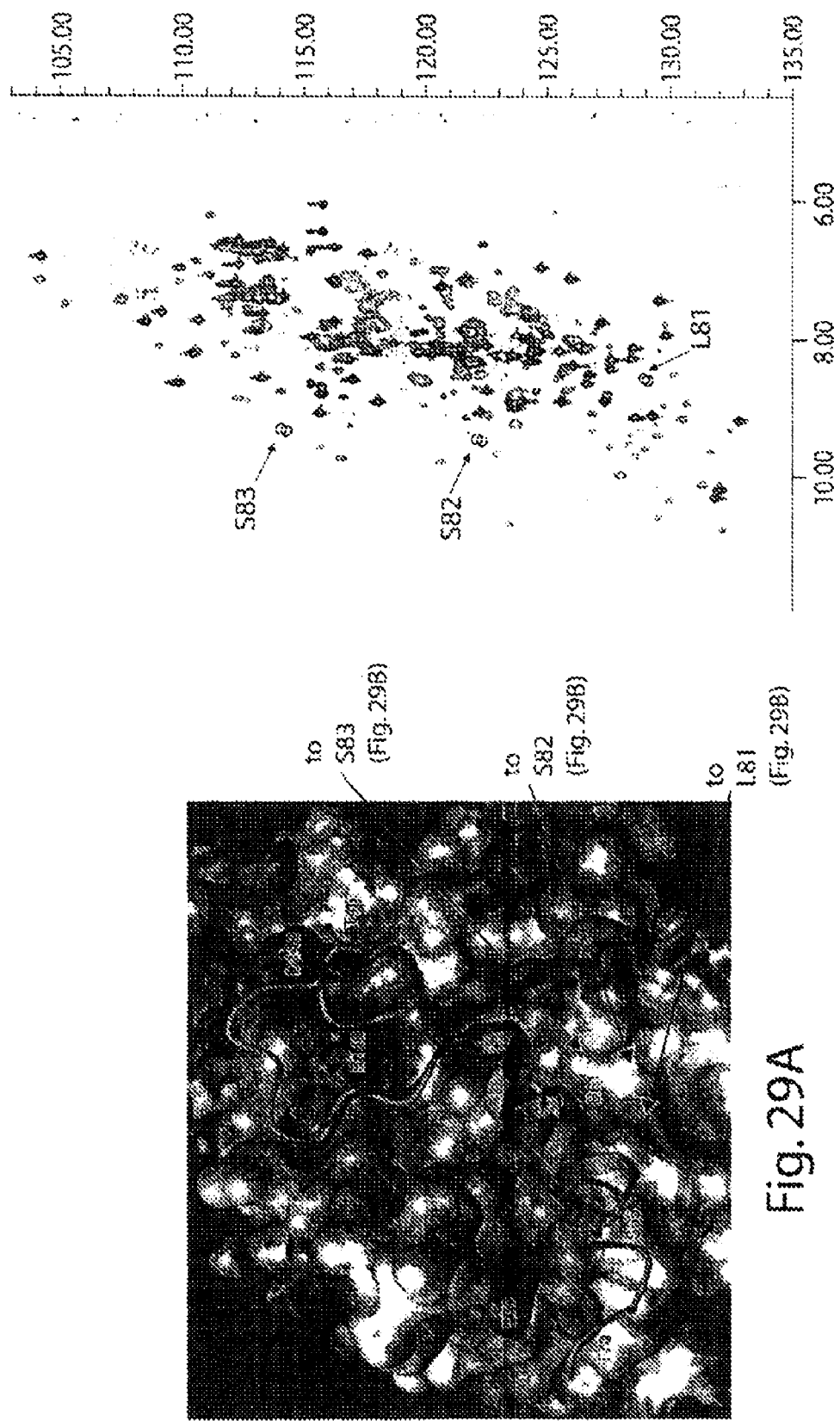
FIG. 29A is a diagram showing the location of the binding sites of compound ICCB-15644.
FIG. 29B is a dot blot.
Figure 30B:
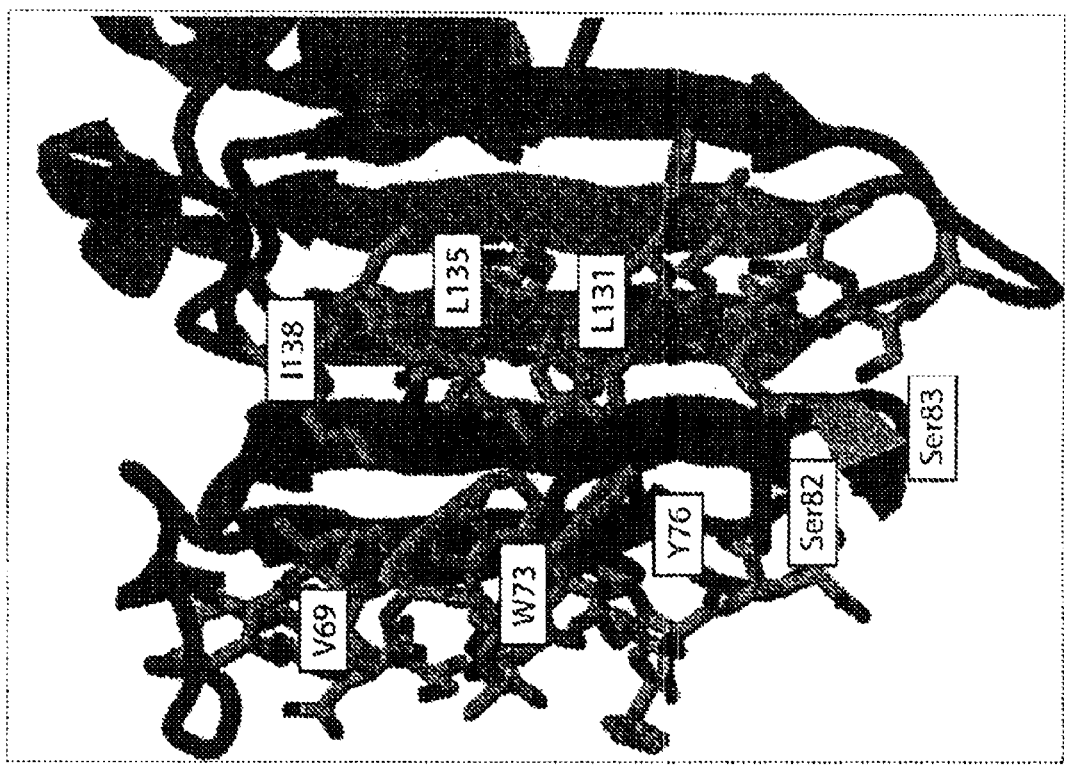
FIGS. 30A-B are diagrams showing inhibitor binding sites.
Figure 30A:
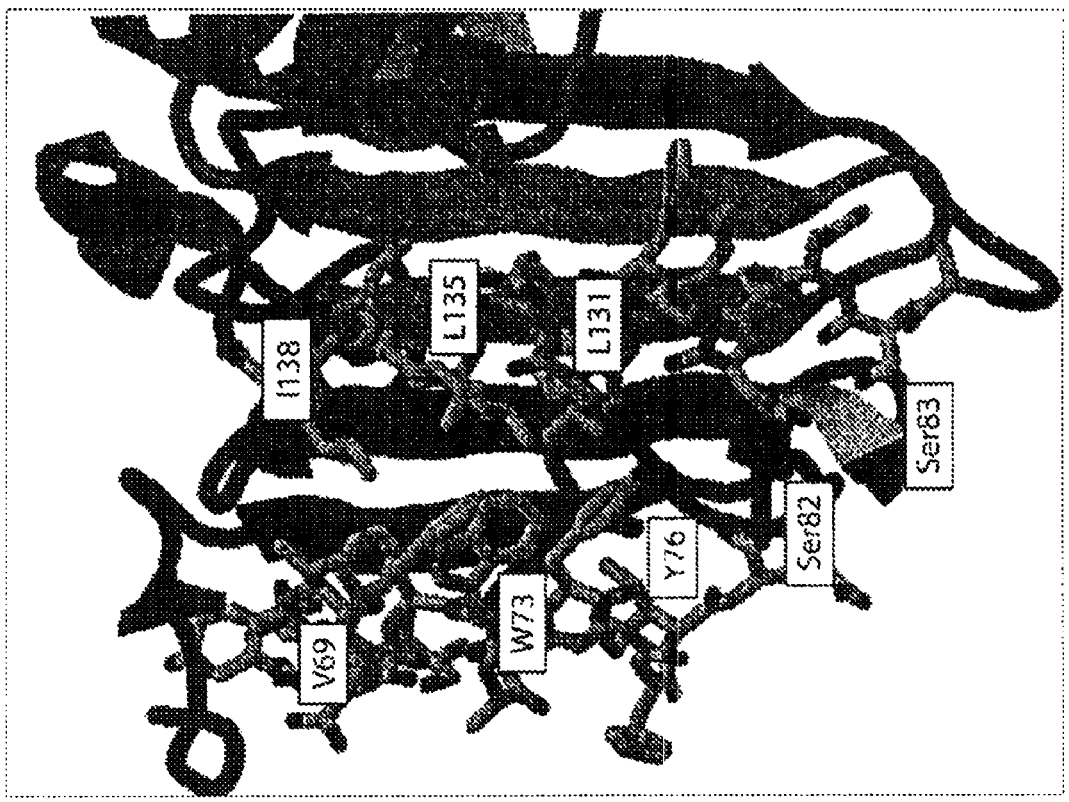
Figure 31:
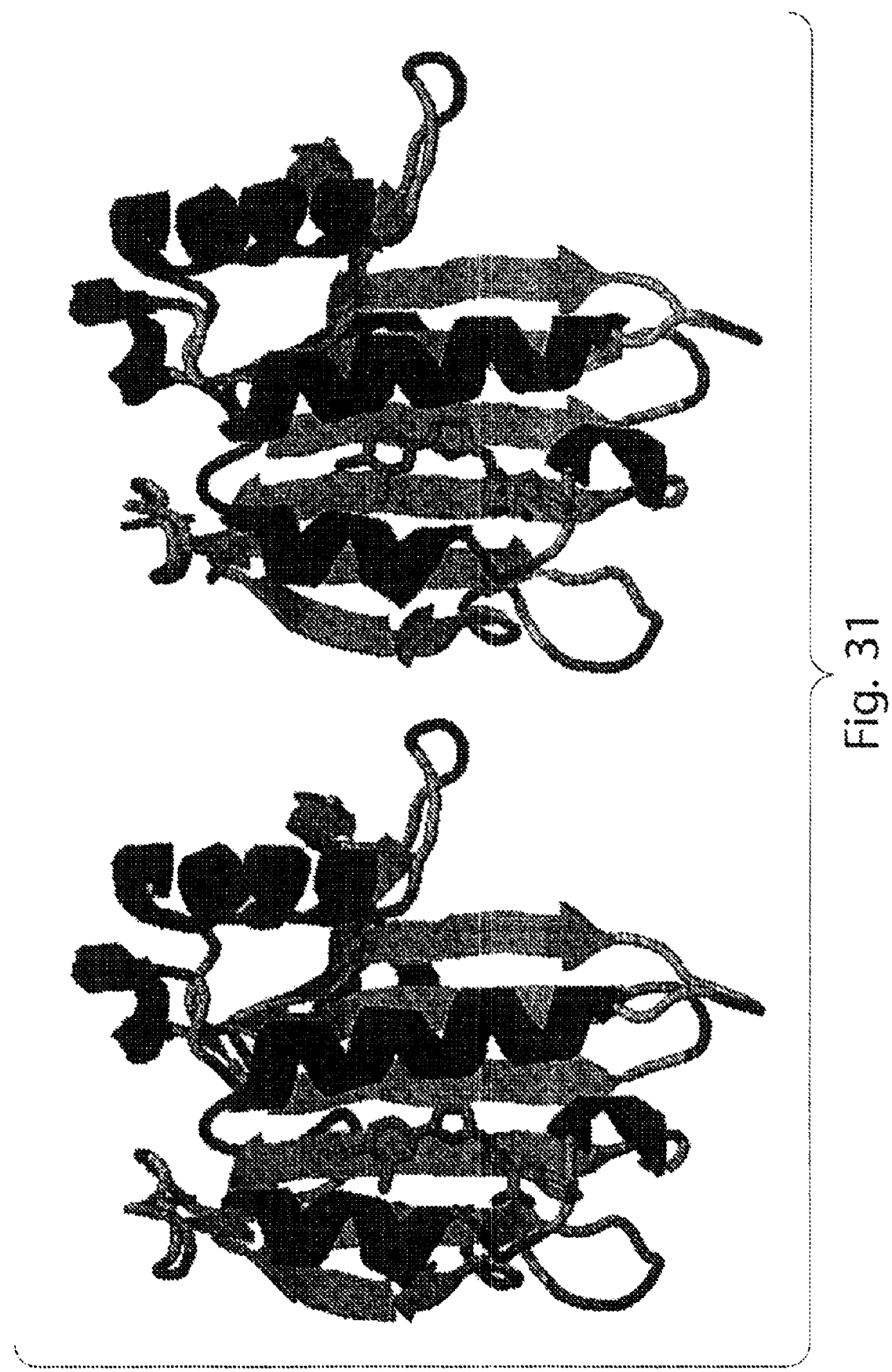
FIG. 31 is a diagram showing inhibitor docked with TreeDock based on NMR perturbation data.

Having determined that EGI-1 (compound 154300) is a specific inhibitor of cap-dependent translation in vitro, biological activity was evaluated in living cells. The compound was tested in a proliferation assay with A549 lung cancer cells, a recognized model for tumor growth and progression. The compound was found to have anti-proliferative activity with an IC50 of approximately 6 uM (FIG. 8A). To determine if this was simply due to toxicity, cell viability after compound treatment was determined using a luminescence assay (FIG. 8B). No significant cytotoxicity is observed in the range of concentrations where EGI-1 (compound 154300) has anti-proliferative activity. These data indicate that this compound inhibits growth and proliferation of tumor cells.

Additional compounds were also tested. Fluorescence polarization data is shown below in Table 1.

TABLE 1

Biological results of Z and E-isomers

| Isomers | | $IC_{50}$ (μM)[a] (4E/4G FP) | $GI_{50}$[b] (SRB μM) |
|---|---|---|---|
| (structure: HOOC-C(=N-NH-thiazole-4-(3,4-diCl-phenyl))-CH2-(2-NO2-phenyl)) | Z-4a | 400 | 6 |
| | E-4a | 410 | 3 |
| (structure: HO-CH2-CH(NH-NH-thiazole-4-(3,4-diCl-phenyl))-CH2-(2-NO2-phenyl)) | 4b | >600 | 4 |
| (structure: HOOC-C(=N-NH-thiazole-4-phenyl)-CH2-(2-NO2-phenyl)) | Z-4r | >600 | >20 |
| | E-4r | >600 | 7 |
| (structure: HOOC-C(=N-NH-thiazole-4-(3,4-diCl-phenyl))-CH2-phenyl) | Z-4s | 300 | 14 |
| | E-4s | 355 | 6.5 |
| (structure: HOOC-C(=N-NH-thiazole-4-phenyl)-CH2-phenyl) | Z-4c | 240 | 17 |
| | E-4c | >600 | 16 |
| (structure: H-C(=N-NH-thiazole-4-phenyl)-CH2-phenyl) | Z-4d | >600 | 7 |

TABLE 1-continued
Biological results of Z and E-isomers
| Isomers | | IC$_{50}$ (μM)$^a$ (4E/4G FP) | GI$_{50}$$^b$ (SRB μM) |
|---|---|---|---|
| 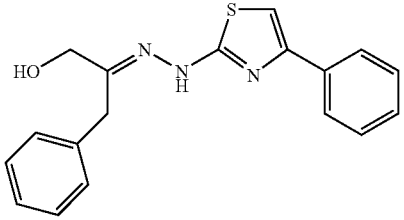 | Z-4e | >600 | 14 |
| 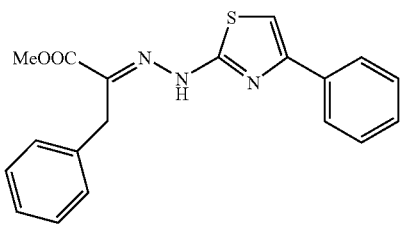 | Z-4f<br>E-4f | >600<br>>600 | 11<br>7 |
| 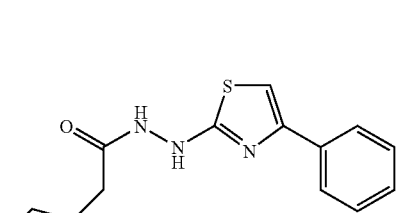 | 4g | >600 | >20 |
| 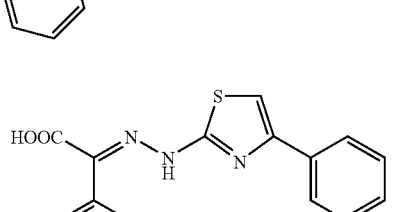 | Z-4h<br>E-4h | >600<br>>600 | 13,<br>10 |
| 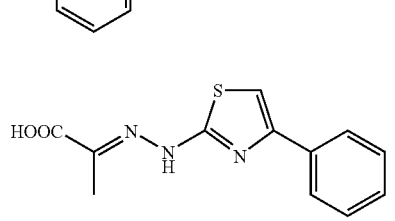 | Z-4i<br>E-4i | >600<br>>600 | >20<br>>20 |
| 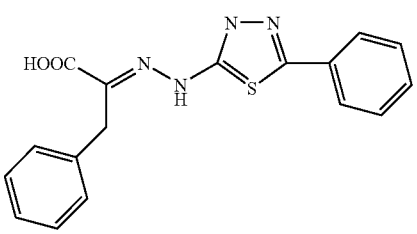 | Z-4k<br>E-4k | >600<br>>600 | >10<br>9 |

TABLE 1-continued
Biological results of Z and E-isomers
| Isomers | | IC$_{50}$ (μM)$^a$ (4E/4G FP) | GI$_{50}$$^b$ (SRB μM) |
|---|---|---|---|
| 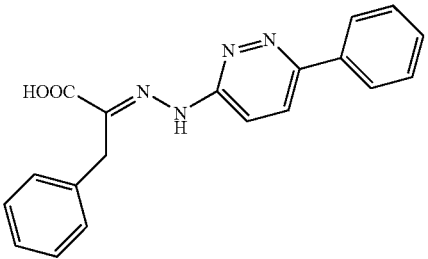 | Z-4l<br>E-4l<br>E-4k | >600<br>>600<br>>600 | >10<br>8<br>9 |
| 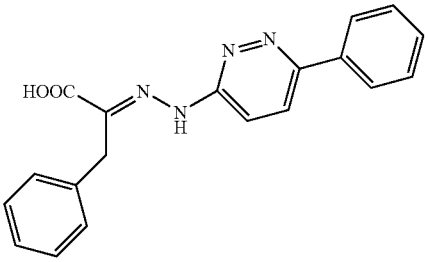 | Z-4l<br>E-4l | >600<br>>600 | >10<br>8 |
| 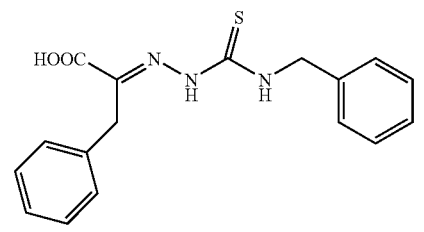 | E:Z = 5:2<br>(4m) | 550 | >10 |
| 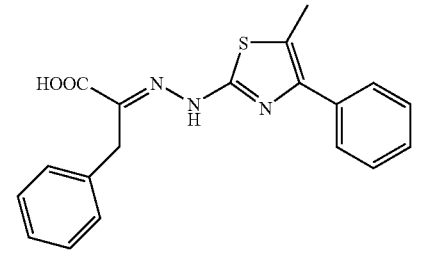 | Z-4n<br>E-4n | 240<br>350 | 4<br>6 |
| 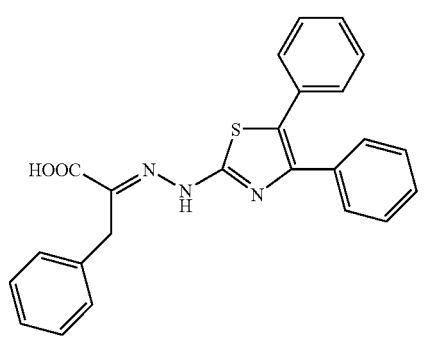 | Z-4o<br>E-4o | 50,<br>90 | 1<br>1.5 |

TABLE 1-continued

Biological results of Z and E-isomers

| Isomers | | IC$_{50}$ (μM)$^a$ (4E/4G FP) | GI$_{50}$$^b$ (SRB μM) |
|---|---|---|---|
| (structure: HOOC-C(=N-NH-benzothiazole)-CH2-phenyl) | Z-4p | >600 | >20 |
| | E-4p | >600 | 4 |
| (structure: HO-C(=O)-CH(NH-C(=O)-4-phenylthiazol-2-yl)-CH2-phenyl) | — | >600 | N/A |
| (structure: HO-C(=O)-CH(C(=O)-NH-4-phenylthiazol-2-yl)-CH2-phenyl) | — | >600 | N/A |
| (structure: HO-C(=O)-CH(NH-CH2-4-phenylthiazol-2-yl)-CH2-phenyl) | — | insoluble | N/A |
| (structure: HOOC-C(=N-NH-4-biphenylthiazol-2-yl)-CH2-(2-nitrophenyl)) | E/Z > 80% | 225 | 4 |
| (structure: HOOC-C(=N-NH-4-(2-naphthyl)thiazol-2-yl)-CH2-(2-nitrophenyl)) | E/Z > 80% | 215 | 6 |

TABLE 1-continued
Biological results of Z and E-isomers
| Isomers | | IC$_{50}$ (μM)$^a$ (4E/4G FP) | GI$_{50}$$^b$ (SRB μM) |
|---|---|---|---|
| 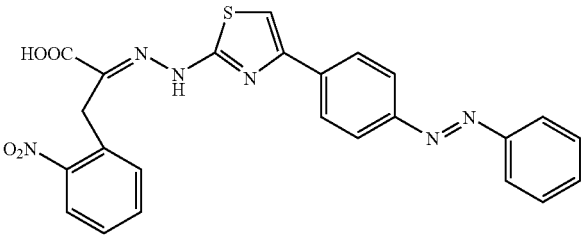 | E/Z > 80% | 150 | 4 |
| 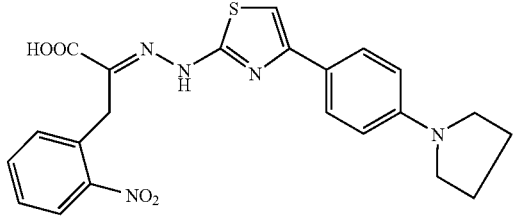 | E/Z > 90% | >600 | >20 |
| 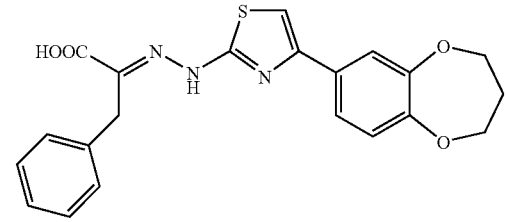 | E/Z > 80% | 400 | |
| 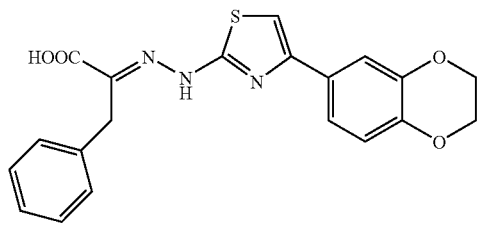 | E/Z > 80% | 170 | |
| 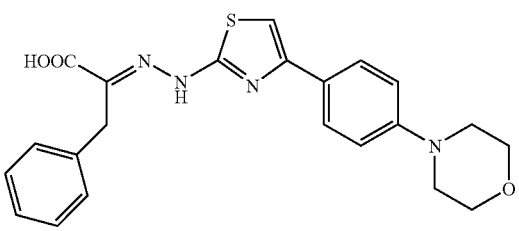 | E/Z > 80% | >125 | |
| 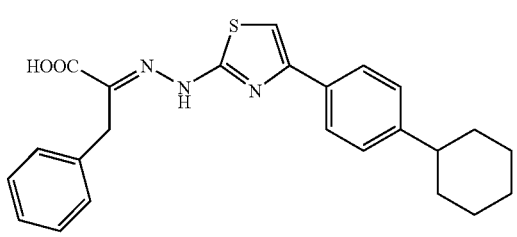 | E/Z > 80% | 100 | |

TABLE 1-continued

Biological results of Z and E-isomers

| Isomers | IC$_{50}$ (μM)[a] (4E/4G FP) | GI$_{50}$[b] (SRB μM) |
|---|---|---|
| [structure: HOOC-C(=C(H)-phenyl)-NH-CH2-thiazole-phenyl] | >600 | |

[a] IC$_{50}$ was measured by fluorescent polarization assay. The values indicate the average concentration needed to inhibit 50% of ceIF4E/EIF4G interaction. The experiments were done in triplicate with SD< ± 10%, using eIE4GII peptide and DMSO as the positive and negative controls, respectively.
[b] GI$_{50}$ was measured using sulforhodamine B assay. The values indicate the average concentration needed to inhibit 50% of cell proliferation. The experiments were done in triplicate with SD< ± 10%, Using CLT and DMSO as the positive and negative controls, respectively.

Preferential Inhibitors of Cap-Dependent Translation Inhibit Proliferation of Tumor Cells Certain classes or types of tumors are characterized by overexpression of eIF4e or overexpression of eIF4G. Inhibitory compounds that preferentially inhibit of cap-dependent translation compared to cap-independent translation are useful to inhibit growth and progression of those classes or tumor types in which eIF4e or eIF4G are overexpressed (compared to normal non-cancerous cells of the same tissue type).

Small molecule inhibitors of the eIF4E/eIF4G interaction were identified as described above. One example of compounds identified in the screen described above, EGI-1 (compound 154300), was further tested and found specifically inhibit cap-dependent translation and have potent anti-proliferative activity. The data described herein indicates the compounds described above are therapeutically useful to inhibit proliferation of tumors in which eIF4E or eIF4G is overexpressed.

Prior to this invention, it was not possible to specifically inhibit cap-dependent translation with a pharmacological agent. Existing methods/compositions, e.g., cycloheximide, inhibit all protein synthesis or target a signalling molecule upstream of 4E-BP phosphorylation which leads to other potentially deleterious downstream effects. These screening strategy described above is also useful to identify compounds that inhibit the eIF4E-eIF4G association.

The use of antisense RNA to lower levels of eIF4E has been shown to suppress the tumorigenic and angiogenic properties of a head and neck squamous cell carcinoma cell line. Analogs of rapamycin, which act by inhibiting mTOR kinase, reducing 4E-BP phosphorylation, and thus decreasing the amount of free eIF4E, have been tested.

Other embodiments are within the scope and spirit of the invention. While the description above refers to the invention, the description may include more than one invention.

EXAMPLES

Example 1

NMR-Derived Structure-Based Design and Synthesis 2-Thiazolyl Hydrazones as Inhibitiors of eIF4E/eIF4G Interaction Eukaryotic initiation factor 4E (eIF4E) is a highly conserved 25 kDa cap-binding protein. eIF4E binds to both the 5'-end of mRNA-cap and eIF4G thereby bringing together these two molecules[1]. eIF4G is a large master scaffolding protein that directly interacts with eIF4E, and eIF4A, an RNA-dependent ATPase that acts also as a helicase to unwind the secondary structure of the 5' untranslated region, to form the eIF4F complex. The hypophosphorylated eIF4E-binding protein (4E-BP) competes with eIF4G for binding to eIF4E and thereby acts as the physiological inhibitor of the eIF4E/eIF4G interaction that restricts formation of the eIF4F complex. Phosphorylation of 4E-BP releases eIF4E enabling formation of the eIF4F complex, a key regulator of translation initiation.

Translation initiation plays a critical role in the control of cell proliferation, malignant transformation and maintenance of transformed phenotypes. This is because mRNAs encoding for many oncogenic proteins and growth factors have highly structured 5'UTR that make their translation highly dependent on the helicase activity of the eIF4F complex. Consistently, over-expression of eIF4E in normal cultured cells causes malignant transformation, while inhibition of either eIF4E expression or the eIF4E/eIF4G interaction reverses the malignant phenotype in vitro and in vivo. For these reasons, small molecule inhibitors of translation initiation that mimic 4E-BP in preventing formation of the eIF4F complex are promising candidates for the development of novel target specific cancer therapy.

Figure 32:
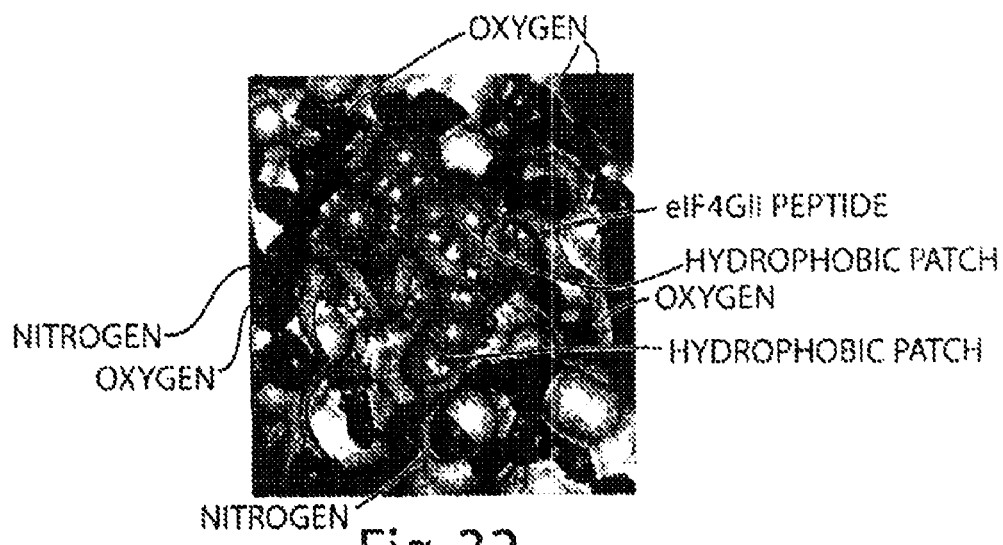
FIG. 32 is a diagram showing Crystal structure of mouse eIF4E bound to a peptide derived from eIF4GII. eIF4E is shown in surface representation (dark shading represent O and N atoms), The eIF4GII peptide is shown in ribbon. Key Residues V69, W73, Y76, L131, L135 and I138 form a hydrophobic patch, (shown in light shading) which forms a putative "hot spot" for binding the eIF4E-binding domain in eIF4GII and 4E-BP.

High resolution structures of N-terminally truncated human and murine eIF4E have been solved by X-ray crystallography and the structure of S. cerevisiae eIF4E has been determined using NMR spectroscopy. In addition, the crystal structures of N-terminally truncated human eIF4E with short peptides derived from eIG4GII and 4E-BP have been reported. The bound peptide containing the conserved motif YxxxxLΦ adopts an L-shaped structure that binds to the dorsal hydrophobic surface of a groove formed by segments 37-39, 68-84 and 120-140 of eIF4E. A hydrophobic patch comprised of V69, W73, Y76, L131, L135 and I138 could serve as a hot spot for interacting with a complementary eIF4E binding hydrophobic surface in eIF4G and 4E-BP (FIG. 32).

We have developed a high throughput fluorescence polarization (FP) assay to identify potential inhibitors of eIF4E/eIF4G interaction. The assay identifies compounds that inhibit binding of a fluorescein-tagged peptide derived from the conserved eIF4E-binding motif of eIF4G. Screening of the Chembridge Library with this assay resulted in the identification of several hits including a 2-thiazolyl hydrazone derivative that was chosen for hit-to-lead development because of its higher potency (shown below, compound 1). The overall goal of this study was to generate more active small molecules that inhibit the eIF4E/eIF4G interaction, thus serving as potential anti-cancer drug.

Compound 1

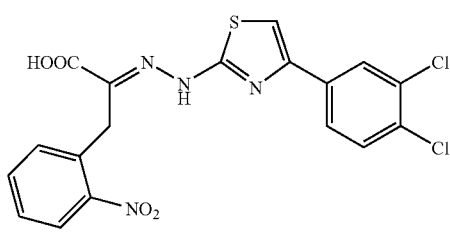

Figure 33A:
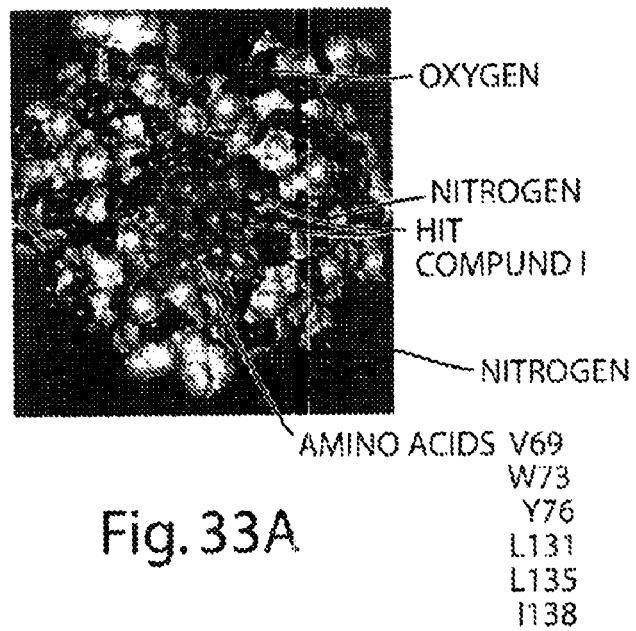
FIG. 33A is a diagram showing Predicted binding mode generated by Treedock docking program. The illustration was made with the program InSight II. Displayed is a contact surface between mouse eIF4E protein (dark shading represent O and N atoms), and the hit compound 1. Amino acid residues V69, W73, Y76, L131, L135 and I138 (light shading) are the eIF4E interaction surface with eIF4G peptide.
Figure 33B:
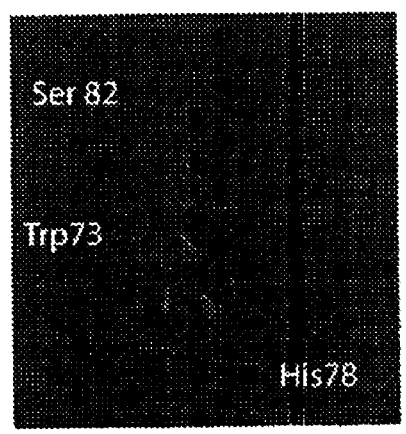
FIG. 33B is a diagram showing Simulated Interaction of inhibitor with mouse eIF4E amino acid residue Trp73, His 78.

Modeling the Binding Site of the Hit Compound 1 on eIF4E by NMR Mapping and Docking Experiments The binding site of the lead compound 1 on eIF4E was identified from chemical shift mapping using the $^{15}$N-$^{1}$H HSQC analysis of the eIF4E in the absence and presence of the small molecule inhibitor. Residues I81, S82 and S83, whose signals were shifted the most, were identified as comprising the main interaction site between the inhibitor and the eIF4E protein. These residues are adjacent to the putative hot spot that binds the eIF4G-derived peptide. This information was used as restraints in the computational modeling of the structure of eIF4E/inhibitor complex. The TreeDock software was used for docking experiments. The program exhaustively searched all possible docked conformations of the inhibitor and interaction sites at the protein surface, evaluated the binding energy based on the Lennard-Jones and hydrogen bond potentials, and identified those arrangements that are most energetically favorable and consistent with the chemical shift mapping data. The results indicate that inhibitor 1 partially overlaps with the binding site for eIF4G (FIG. 33A). The simulated interaction between the inhibitor and specific amino acid residues in eIF4E is presented in FIG. 33B. This model suggests that the binding orientation of the inhibitor to eIF4E is determined through a salt bridge formation between the carboxyl moiety of the inhibitor and the imidazole NH of H78 (4.3 Å), and a hydrogen bond with D77. The 3,4-dichlorophenyl ring is positioned to form a π-π interaction with the indole moiety of the W73 residue located at the center of the putative hot spot that is reportedly essential for the eIF4E/eIF4G binding interaction.

In the inhibitor-eIF4E interaction model however, the presentation of eIF4E during the docking process as a rigid structure does not allow for the formation of a ligand-induced conformational change. The identification of eIF4E residues that are critical for binding to eIF4G, will nonetheless provide insights important for hit-to-lead optimization.

Examining the complex 1-eIF4E interfaces suggested that the hydrophobic interaction with the hot spot could be optimized by increasing the size of the hydrophobic moiety substituting position 4 on the 2-thiazolyl ring. This assumption is consistent with site-direct mutagenesis studies showing that changing Trp73→Ala in murine eIF4E prevents interactions with either 4E-BP1 or eIF4GI[9]. Herein we report the synthesis and biological activities of 2-thiazolyl hydrazones substituted at position 4 of the thiazolyl ring by substituents varying in size, hydrophobicity and shape.

The general approach to the synthesis of the 2-thiazolyl hydrazones is described in the scheme shown directly below. 4-Substituted 2-thiazolyl hydrazines (2) were prepared by Hantzsch-typed cyclodehydration of thiosemicarbazide with bromoacetophenones (1) in dioxane at room temperature followed by neutralization to generate free hydrazines 212. 1H NMR spectra of the products, measured in DMSO-d6 solution, displayed the anticipated three hydrazino protons as two broad singlets at 8.67 (1H) and 4.91 (2H) ppm and the characteristic position 5 proton on the thiazolyl at 7.31 ppm as a singlet. The condensation reactions between 4-substituted-2-thiazolyl hydrazines (2) with 2-nitrophenylpyruvic acid (3) in the presence of 5% acetic acid yielded the substituted 2-thiazolyl hydrazones (4) 13. All the products were purified by HPLC and tested for their competitive binding and growth inhibition activities in cell free and cell-based assays, respectively.

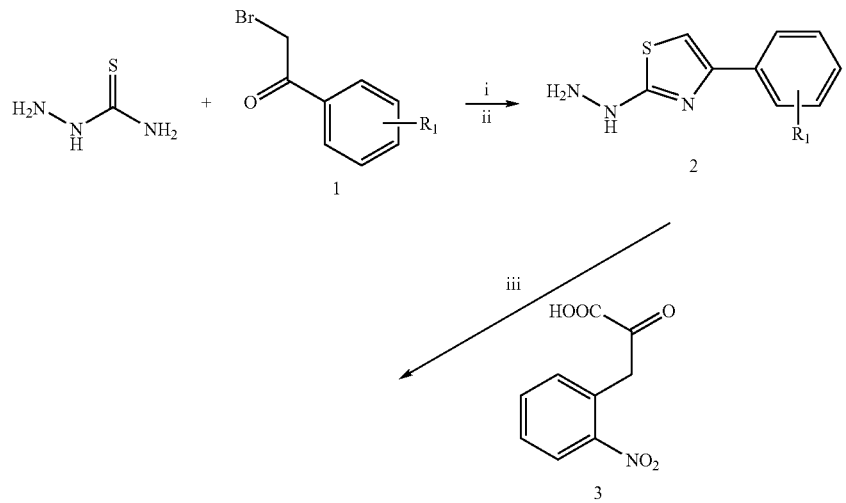

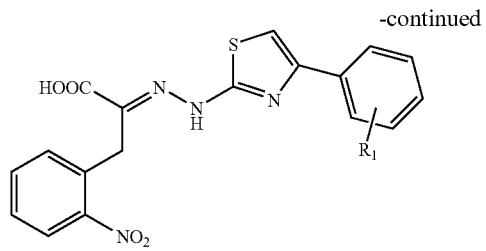

4

Bioassay

A fluorescence polarization (FP) assay was used to measure binding to eIF4E by competing with a fluorogenic eIF4G-derived peptide containing the conserved eIF4E-binding motif (KRYDREFLLGF) (SEQ ID NO:4). Displacement of Nα-fluorescein tagged eIF4G-derived peptide by a competing ligand causes a large decrease in fluorescence polarization. The non-tagged version of the same eIF4G-derived peptide and DMSO were used as positive and negative control, respectively. Results are presented as ratios of $IC_{50}$ (2-thyazoly hydrazone)/$IC_{50}$ (non-tagged peptide, $IC_{50}=75\mu M$).

A functional cell free assay determined the relative effects of the compounds on cap- and IRES-dependent translations. This assay involved the in vitro translation of bicistronic mRNA reporter construct encoding for *renilla* luciferase in a cap-dependent and for firefly luciferase in a cap independent manner, the later driven by cricket paralysis virus IRES. Analysis of translation activity included subsequent incubations with firefly- and *renilla* luciferase substrates to determine the relative luminesemce vs. control. $m^7GDP$ and emetine were used as positive and negative controls for cap-dependent and general translation inhibition, respectively. in vitro translation of cap-dependent mRNA was inhibited by inhibitors of eIF4E/eIF4G interaction, while translation from the IRES was paradoxically enhanced, presumably due to increased availability of ribosomes as cap-dependent translation is inhibited).

Figure 34:
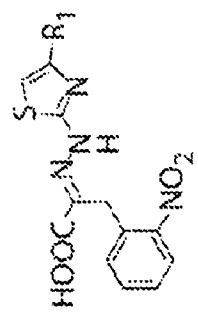
FIG. 34 is a table showing the biological activities of 2-thiazolyl hydrazone analogues modified at position 4 with substituted phenyl moieties.

Compounds were further tested for cell growth inhibition in a human lung cancer cell line (A549) and conlon cancer cell line (HT29). The Alamar Blue assay, which specifically measures the inhibition of cell proliferation, was used to assess the $GI_{50}$'s of the compounds. The biological data is summarized in FIG. 34.

Synthesis of substituted 2-thiazolyl hydrazones can also be achieved by condensation of thiosemicarbazide with pyruvic acids first, and then followed by cylozation with substituted bromoacetophenones.

We designed and synthesized analogues of the hit 2-thiazolyl hydrazone 1 carrying a variety of substituted phenyls on position 4 of the thiazolyl ring. The reference compound 4a, which has a non-substituted phenyl on the thiazolyl ring, showed dramatic decrease in the FP assay and in the growth inhibition of both cell lines as compared with the hit compound 1. Compounds 4c, 4f and 4g, substituted with 2-naphtyl, 4-biphenyl and 4-cyclohexyl-phenyl, respectively, displayed 2-4-fold higher binding affinities than the hit compound 1. The 2-fold higher potency of 4g as compared with 4f suggest that lipophilic bulkiness of a cyclohexyl moiety at the 4-position of the phenyl ring contributes more favorably to the binding at the hot spot than the aromatic planar phenyl at the same positin. Taken together these findings support our model that increased size and lipophylicity of substituents in position 4 of the thiazolyl ring would optimize the interaction with the putative hot spot.

Examining the results obtained with analogues 4d, 4e, 4h, 4i and 4j, substituted with 3,4-dihydro-2H-benzo[b][1,4]dioxepin-7-yl, 2,3-dihydro-benzo[1,4]dioxin-6-yl)-thiazol-2-yl, 4-morpholin-4-yl-phenyl, 4-pyrrolidin-1-yl-phenyl and 4-phenylazo-phenyl, respectively, suggest a more complex model in which the presence and location of heteroatoms as well as the nature of the moiety presenting them may play a role in the interaction with the putative hot spot. Comparison of 4d with 4e indicates the smaller [1,4]dioxin ring leads to more than 2-fold improvement in potency while the larger [1,4]dioxepin ring remained equipotent to the hit compound 1, as measured by the FP assay. The larger and more flexible [1,4]dioxepin ring may present some disruptive interaction with the binding site as compared to the smaller and more rigid [1,4]dioxin ring. Interestingly, modifications with 4-pyrrolidin-1-yl-phenyl 4h and 4-morpholin-4-yl-phenyl 4i were significantly less active in the FP assay than the hit compound 1. The introduction of the tertiary cyclic amine at para position of the phenyl ring may not be tolerated due to lack of charge or hydrogen bond compatibility.

The almost 3-fold enhancement in potency in the FP assay of the compound substituted with 4-phenylazo-phenyl 4j as compared with the hit compound 1 is in-line with the enhancements observed for 4c and 4f substituted with 2-naphtyl and 4-biphenyl, respectively. This finding is consistent with our model-based prediction of available extended hydrophobic sites on the eIF4G binding surface of eIF4E.

In general, the growth inhibition data is in agreement with the binding competition data generated in the FP assay. Most weakly binding analogs, 4a, 4e, 4h and 4i, with $IC_{50}$ ratios greater than 5.3 have $GI_{50}s>24$ μM in both cell lines. All potently binding analogs 4c, 4d, 4f, 4g and 4j, with $IC_{50}$ ratios smaller or equal to 3 μM, have $GI_{50}s$ that are lower than 10 μM in at least one cell line. The only exception is the hit compound 1 that has $IC_{50}$ ratio similar to 4e but is more potent in inhibiting the HT29 and A549 cell lines ($GI_{50}=9$ and 5 μM vs. 45 and 24 μM, respectively). We can not identify clear preference for the 2-thiazolyl hydrazones in inhibiting either the colon or the lung cancer lines. The above correlation between a cell-free target isolated assay like the eIF4E/eIF4G binding competition FP assay and cell-based growth inhibition assay is very encouraging and suggests that inhibition of translation initiation may be the prime cause for growth inhibition in the tested cells.

Figure 35A:
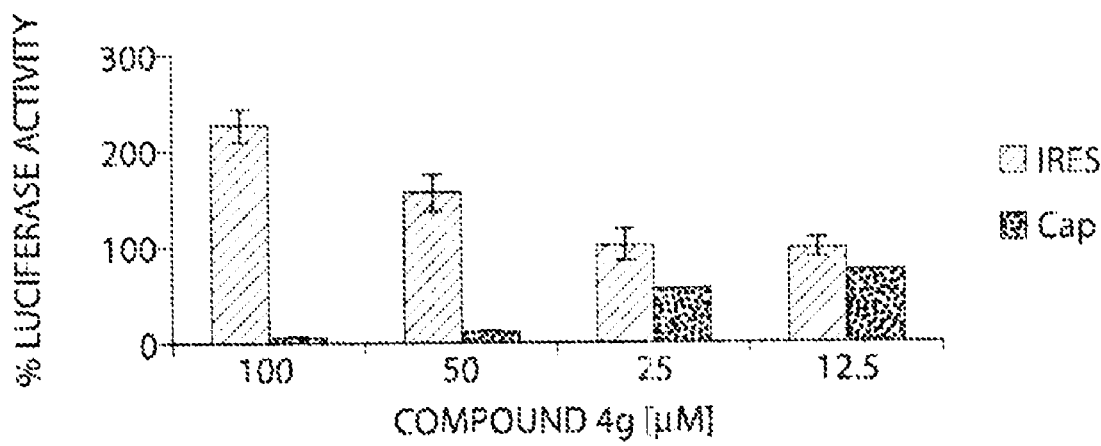
FIGS. 35A-B are graphs showing $IC_{50}$ was measured using fluorescent polarization (FP) assay. Results are presented as ratios of the compounds $IC_{50}$ values ($IC_{50}$(comp.)) to the $IC_{50}$ value of the eIF4G-derived peptide ($IC_{50}$(pept.)). The eIF4G-derived peptide (KRYDREFLLGF (SEQ ID NO:4), $IC_{50}$=75μM) and DMSO served as positive and negative controls, respectively. The experiments were done in triplicate with SD<±10%.sup.b) $GI_{50}$ was measured using Alamar Blue assay. The values indicate the average concentration needed to inhibit 50% of cell proliferation. The experiments were done in triplicate with SD<±10%, using clotrimazole (CLT) and DMSO as the positive and negative controls, respectively Inhibition of cap-dependent translation in rabbit reticulocyte lysate by compound 4g (A) and 4b (B). A dual luciferase reporter mRNA was translated for 90 minutes at 30° C. in RedNova reticulocyte lysate (Novagen) in the presence of increasing concentrations of the compound. IRES-regulated renilla luciferase (blue) and cap-regulated firefly luciferase (purple) activity was measured and normalized against an untreated control reaction. The m$^7$GDP and emetine were used as the positive and negative controls, respectively.
Figure 35B:
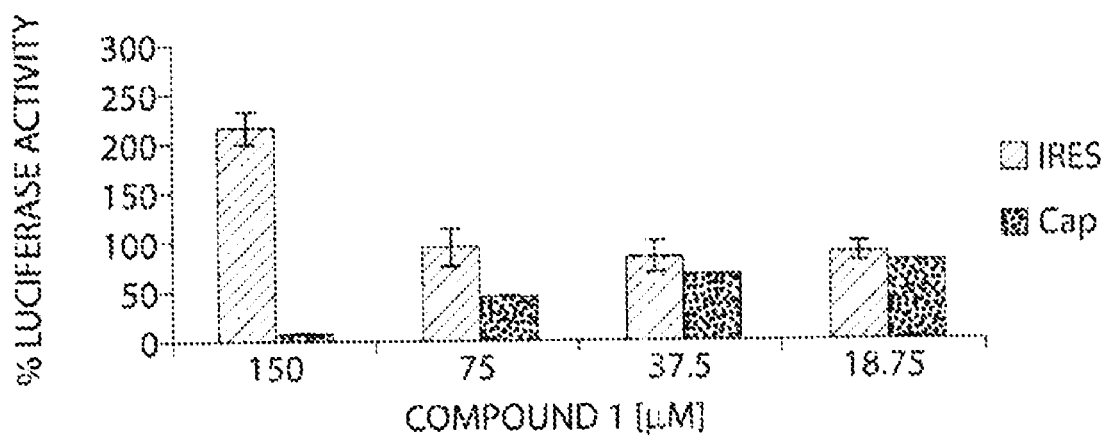

More direct demonstration that inhibition of eIF4E/eIF4G interaction by the 2-thyazolyl hydrazones result in preferential inhibition of cap-dependent as compared to IRES-dependent translation of mRNA was derived from the inhibition of in vitro translation of a bicistronic mRNA dual luciferase reporter construct in a rabbit reticulocyte lysate preparation. We selected 4g, the most potent compound of this series in the FP assay, and compared it to the hit compound 1 for it capacity to inhibit in vitro cap-dependent translation. Both compounds inhibit dose-dependently cap-dependent translation of renilla luciferase and simultaneously enhance the IRES-dependent translation of the firefly luciferase (FIG. 35). In accordance with the binding inhibition FP assay the most potent compound 4g was also more effective in inhibiting the in vitro translation of the cap-dependent luciferase as compared to the less potent hit compound 1

In summary, a molecular model of eIF4E-hit compound 1 interface was utilized for structure-based design of eIF4E-eIF4G inihbitors. This model incorporated constraints generated by chemical shift mapping to enable the docking of the small molecule into the binding site of eIF4E.

We have successfully designed and synthesized a series of novel 2-thiazolyl hydrazone analogues modified in 5-position of the thiazolidine ring with a diversity of hydrophobic moieties. Our study validated the molecular model and generated analogs with improved binding affinity to eIF4E and potent inhibitors of cap-dependent translation as compared to the parent hit compound 1. We will continue to optimize the 2-thiazolyl hydrazone scaffold for inhibition of eIF4E/eIF4Ginteraction utilizing the molecular model. As we improve the resolution of our working model we will be able to better fine-tune our design to generate optimized inhibitors of eIF4E/eIF4G interaction.

$^1$H NMR spectra of intermediates and final 2-thiazolyl hydrazones were recorded in $d_6$-DMSO at 500 MHz on a Varian VX500 or at 400 MHz on a Varian VX400 instruments. TLC analyses were performed on Kieselgel 60 F254 silica gel plates (EMD chemicals, Inc.). Column chromatography was performed on Baker 7024 flash silica gel. Melting points were measured in Pyrex capillary tubes in a Mel-Temp "Electronthermal" apparatus and are not corrected. LC-MS was performed in Waters LC-MS (APCI mode) with XTerra $C_8$ 30×100 mm column. Elemental analyses were obtained only for the final products, and were performed by Robertson Laboratories, Madison, N.J. Analyses were within ±0.4% of theoretical values. All the starting materials were obtained from commercial sources and were used without further purification.

Procedure for synthesis 2-{[4-(3,4-Dichloro-phenyl)-thiazol-2-yl]-hydrazono}-3-(2-nitro-phenyl)-propionic acid Step 1-4-(3,4-Dichloro-phenyl)-thiazol-2-yl-hydrazine A solution of a thiosemicarbazide (10 mmol, 0.91 g) and 3,4-dichlorophenylacetyl bromide (10 mm ol, 2.68 g) in dioxane (20 mL) was stirred at room temperature for 16 h. The precipitate of hydrobromide salt was filtered and washed with dioxane (3×10 mL) basified with 2N $Na_2CO_3$ (20 mL). The product was filtered, washed with water and dried (2.08 g, 80%). The product could be used in the subsequent step without further reaction. $^1$H NMR (400 MHz) δ 8.67 (s, 1H, NH), 8.00 (d, J=1.6 Hz, 1H), 7.76 (dd, J=1.6 Hz, J=8.4 Hz, 1H), 7.60 (d, J=8.4 Hz, 1H), 7.31 (s 1H), 4.906 (s, 2H, $NH_2$) MS$^+$(APCI), 259.68, (M+1; calcd 258.97 (M+)

Step 2-2-{[4-(3,4-Dichloro-phenyl)-thiazol-2-yl]-hydrazono}-3-(2-nitrophenyl)-propionic acid 3-(2-Nitrophenyl)-2-oxo-propionic acid (1.0 mmol, 209 mg) in 5% acetic acid (2 mL) was added in to solution of 4-(3,4-dichloro-phenyl)-thiazol-2-yl-hydrazine (1.0 mmol, 259 mg) in ethanol (4 mL). The reaction mixture was stirred at 90° C. for 1 h and cooled to 0° C.; the orange precipitate was filtered and washed by water. Recrystallization from MeOH—$H_2O$ afforded the final product as a yellow power (600 mg, 66.7%). mp 184-186° C.; the product was further separated by HPLC-MS, using a 30 min linear gradient of 50-75% of 0.05% HOAc in acetonitril 50% in 0.05% HOAc in water. $^1$H NMR (400 MHz) δ 12.85 (br, 1H), 12.10 (br, 1H), 8.06 (d, J=8.4 Hz, 1H), 8.03(s, 1H), 7.78 (d, J=8.4 Hz, 1H), 7.64 (d, J=6.0 Hz , 2H), 7.61(s, 1H), 7.50 (t, J=7.6 Hz, 1H), 7.06 (d, J=7.6 Hz, 1H), 4.28 (s, 2H).

MS$^+$(APCI) m/z 450.84 (M+), calcd: 450.84 (M+). Anal. Calcd for $C_{18}H_{14}N_4O_4S.0.2H_2O$: C, 47.53; H, 2.75; N, 12.32; Found: C, 47.41; H, 2.59; N, 11.98.

Molecular Docking Studies.

TreeDock module was implemented as a C-program on a single SGI R10k workstation. The input to TreeDock consists of PDB-files for the molecule. employing the coordinates of each atom in a PDB file we identified the solvent accessible surface. The output of TreeDock is stored in two files: one contains the coordinates of the complex and another (optional) records Lennard-Jones energy contribution of all chemical moieties in the accessible surface. Parameters for the Lennard-Jones potential were obtained from the X-PLOR program.

2-{[4-(2,3-Dihydro-benzo[1,4]dioxin-6-yl)-thiazol-2-yl]-hydrazono}-3-(2-nitro-phenyl)-propionic acid (4d)

The product was further separated by HPLC-MS, using a 30 min linear gradient of 50-75% of 0.05% HOAc in acetonitril 50% in 0.05% HOAc in water. $^1$H NMR (400 MHz) δ 12.90 (br, 1H), 12.15 (br, 1H), 8.00 (d, J=8.0 Hz, 1H), J=7.6 Hz, 1H), 7.34-7.38 (m, 2H), 7.28 (s, 1H), 7.21 (d, J=7.6 Hz, 1H), 6.91 (d, J=8.0 Hz, 1H), 4.26 (s, 4H), 4.20 (s, 2H).

MS$^+$(APCI) m/z 441.1 (M+1), calcd: 440.43 (M$^+$). HRMS for $C_{20}H_{16}N_4O_6S+H^+$ Calcd; 441.0869; Found: 441.0874

2-{[4-(3,4-Dihydro-2H-benzo[b][1,4]dioxepin-7-yl)-thiazol-2-yl]-hydrazono}-3-(2-nitro-phenyl)-propionic acid (4e)

The product was further separated by HPLC-MS, using a 30 min linear gradient of 50-75% of 0.05% HOAc in acetonitril 50% in 0.05% HOAc in water. $^1$H NMR (400 MHz) δ 8.00 (d, J=8.0 Hz, 1H), 7.60(t, J=7.6 Hz, 1H), 7.34-7.38 (m, 2H), 7.18 (s, 1H), 7.11 (d, J=7.6 Hz, 1H), 6.91 (d, J=8.0 Hz, 1H), 4.26 (bs, 2H), 4.11 (s, 2H), 2.07 (t, J=5.6 Hz, 2H). MS$^+$(APCI) m/z 455.1 (M+1), calcd: 454.09 (M$^+$). HRMS for $C_{21}H_{18}N_4O_6S+H^+$ Calcd; 455.1025; Found: 455.1032.

2-{[4-(4-Cyclohexyl-phenyl)-thiazol-2-yl]-hydrazono}-3-(2-nitro-phenyl)-propionic acid (4g)

The product was further separated by HPLC-MS, using a 30 min linear gradient of 50-75% of 0.05% HOAc in acetonitril 50% in 0.05% HOAc in water. $^1$H NMR (400 MHz) δ 12.90 (br, 1H), 12.15 (br, 1H), 8.05 (dd, J=7.6 Hz, J=6.8 Hz, 1H), 7.70(d, J=6.4 Hz, 2H), 7.62 (m, 1H), 7.52 (m, 1H), 7.33(s, 1H), 7.21 (d, J=6.4 Hz, 2H), 7.05 (d, J=8.0 Hz, 1H), 4.29 (s, 1.8H), 4.16 (s, 0.2H), 1.77 (d, J=10.4 Hz, 4H), 1.71 (m, 1H), 1.39-1.34 (m, 4H), 1.21 (t, J=9.6 Hz, 2H). MS$^+$ (APCI) m/z 465.1 (M+1), calcd: 464.15 (M$^+$). HRMS for $C_{20}H_{16}N_4O_6S+H^+$, Calcd; 465.1596; Found: 465.1603.

2-{[4-(4-Morpholin-4-yl-phenyl)-thiazol-2-yl]-hydrazono}-3-(2-nitro-phenyl)-propionic acid (4h)

The product was further separated by HPLC-MS, using a 30 min linear gradient of 50-75% of 0.05% HOAc in acetonitril 50% in 0.05% HOAc in water. $^1$H NMR (500 MHz) δ 12.80 (br, 1H), 12.05 (br, 1H), 8.01 (d, J=8.0 Hz, 1H), 7.66(d, J=8.0 Hz, 2H), 7.66-7.56 (t, J=8.0 Hz, 1H), 7.23(s, 1H), 7.08 (d, J=7.5 Hz, 1H), 6.95 (d, J=8.0Hz, 2H), 4.31 (s, 2.0H), 3.14 (s, 4H), 2.51 (s, 4H). MS$^+$(APCI) m/z 468.1 (M+1), calcd: 467.13 (M$^+$). HRMS for $C_{21}H_{18}N_4O_6S+H^+$ Calcd; 468.1341; Found: 468.1349.

3-(2-Nitro-phenyl)-2-{[4-(4-pyrrolidin-1-yl-phenyl)-thiazol-2-yl]-hydrazono}-propionic acid (4i)

The product was further separated by HPLC-MS, using a 30 min linear gradient of 50-75% of 0.05% HOAc in acetonitril 50% in 0.05% HOAc in water. $^1$H NMR (400 MHz) δ 12.80 (br, 1H), 12.05 (br, 1H), 8.04 (d, J=8.0 Hz, 1H), 7.64 (t, J=6.4 Hz, 1H), 7.59 (d, J=8.4 Hz, 2H), 7.52 (t, J=7.2 Hz, 1H), 7.05 (d, J=7.6 Hz, 1H), 7.01(s, 1H), 6.50 (d, J=8.8 Hz, 2H), 4.28 (s, 2.0H), 3.22 (s, 4H), 1.93 (s, 4H). MS$^+$(APCI) m/z 452.1 (M+1), calcd: 451.13 (M$^+$) HRMS for $C_{22}H_{21}N_4O_6S+H^+$ Calcd; 452.1392; Found: 452.1372.

Example 2

Identification of Pharmacophore of 2-Thiazolyl Hydrazones as Inhibitors of eIF4E/eIF4G Interaction Formation of translation initiation complex eIF4F, which consists of the RNA helicase eIF4A, the docking protein eIF4G and the cap binding protein eIF4E, is the rate-limiting step in the initiation process in eukaryotes because of the extremely low abundance of eIF4E. As a part of eIF4F, eIF4E is the major target for regulation by eIF4E-binding proteins (eIF4E-PBs). eIF4E is released from a translationally inactive complex with 4E-BPs upon hypophosphorylation in response to stimulation by insulin and growth factors. eIF4E-BPs dissociate from the complex with eIF4E and allow it to form an active translation initiation complex eIF4F. mRNAs of growth-promoting proteins and oncogene products have often long 5'UTRs and their translation depends crucially on the interaction of the eIF4E/eIF4G interaction in a cap-dependent fashion. On the other hand, many housekeeping proteins and pro-apoptotic proteins are translated in 2a cap-independent fashion through internal ribosomal entry sites (IBES-dependent way). Inhibitors of the eIF4E/eIF4G interaction prevent formation of eIF4F complex would predominantly inhibit translation of mRNAs involved in tumor growth and survival and to have anti-tumor activity.

We have developed a fluorescent polarization assay adapted for high throughput screening to identify inhibitors of eIF4E/4G interaction based on the fact that eIF4G and eIF4E-BPs share the same binding site on dorsal surface of eIF4E and both contain a consensus, the binding motif. A fluorescein-tagged peptide derived from the conserved eIF4E recognition motif of eIF4G and purified eIF4E were used in the screen assay to mimic the eIF4E/eIF4G interaction. After screening the Chembridges Library, several small molecules were identified; the most active hit (1) was chosen as the hit for further medicinal chemistry development. The synthesis and biological evaluation of a series 2-thiazolyl hydrazones as potent inhibitors of translation initiation, which serves to identify the active pharmacophore.

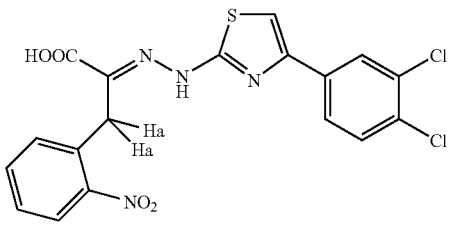

Chemistry

The general synthetic approach to the synthesis of the 2-thiazolyl hydrazones is described in the scheme shown below, as scheme 1. Substituted 2-thiazolyl hydrazines (2) were prepared by Hantzsch-typed cyclodehydration of thiosemicarbazide with appropriate bromoacetones (1) in dioxane at room temperature. The condensation reactions between 2-thiazolyl hydrazines (2) with appropriated ketones or a-keto acid (3) in the presence of 5% acetic acid yielded the substituted 2-thiazolyl hydrazones (4).

Scheme 1 (method A)

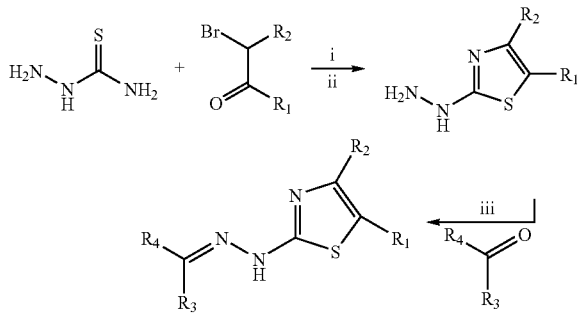

i. Dioxane, 12 h, rt; ii. Na$_2$CO$_3$; iii. EtOH, 5% HOAc, reflux 2 h.

2-Phenyl-5-hydrazineo-1,3,4-thiadiazole (2k) were obtained by diazotization of 2-amino-5-phenyl-1,3,4-thiadiazoles in hydrochloric acid with copper catalysis followed by treatment with hydrazine hydrate. The final product (4k) was synthesized by condensation with □-keto acid. 3-Phenyl-2-[(6-phenyl-pyridazin-3-yl)-hydrazono]-propionic acid (4l) was synthesized by a similar fashion.

Scheme 2 (method B)

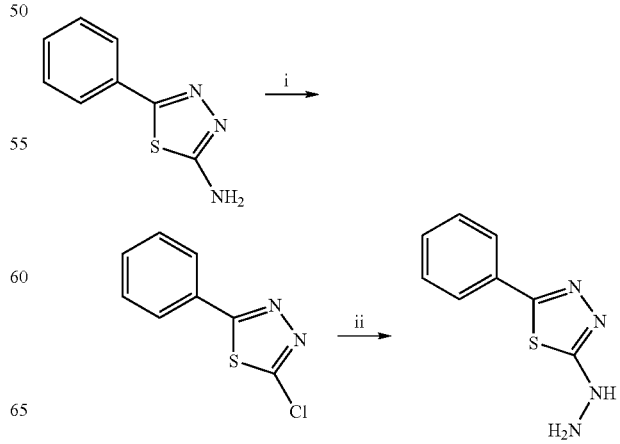

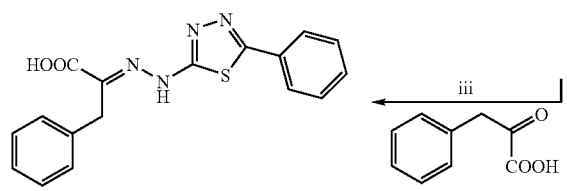
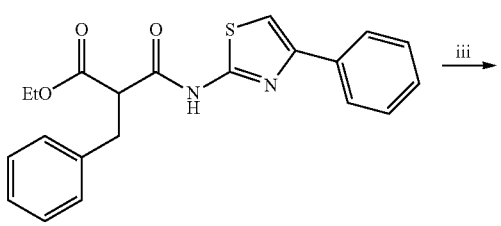
i. NaNO₂/HCl/Cu; ii. N₂H₄; iii. EtOH, 5% HOAc, reflux 2 h.
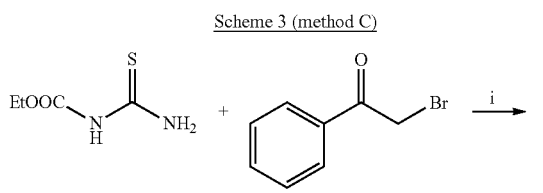
Scheme 3 (method C)
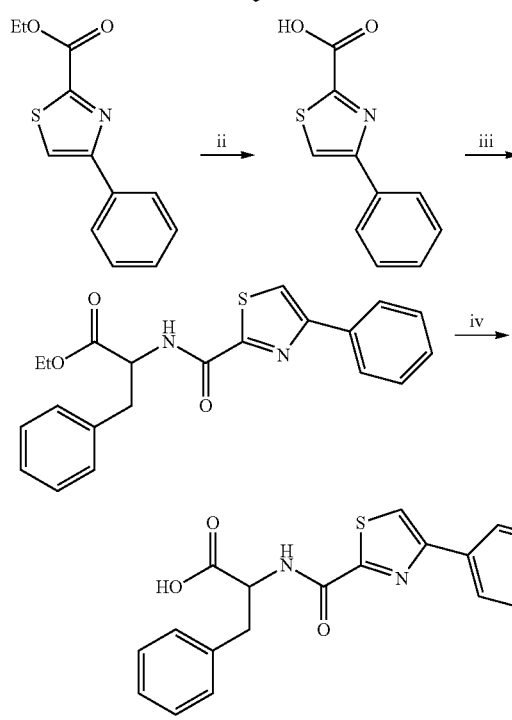
i. dioxane, reflux, 1.5 h; ii. KOHaq, MeOH, 60° C., 15 min; iii. EDCI, DMF, rt, on; iv. KOHaq, EtOH, rt, 2 h.
Scheme 4 (method D)
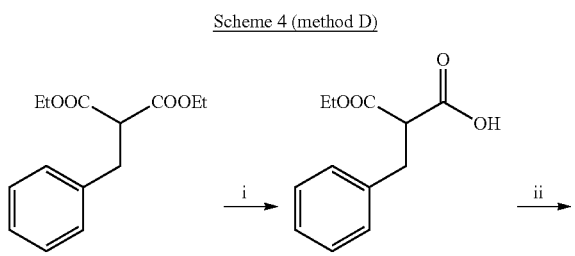
i. KOHaq, EtOH, rt, 1 h; ii. EDCI, DMF, rt, on; iii. KOHaq, EtOH, rt, 2 h.
Scheme 5 (method E)
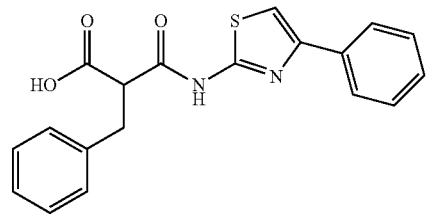
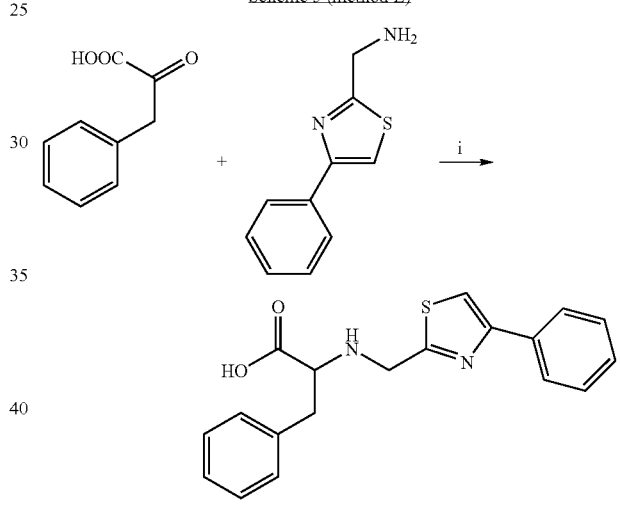
i. NaBH₃CN, MeOH, 3 h.
Scheme 6 (method F)
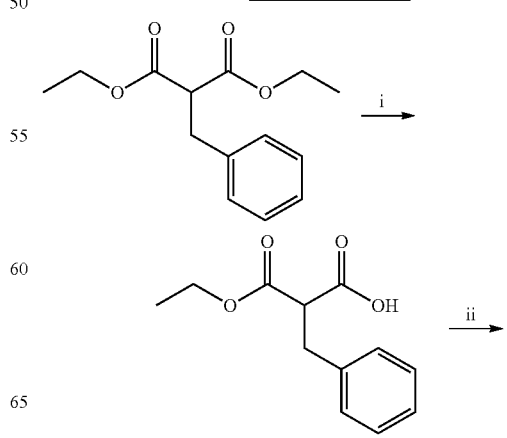

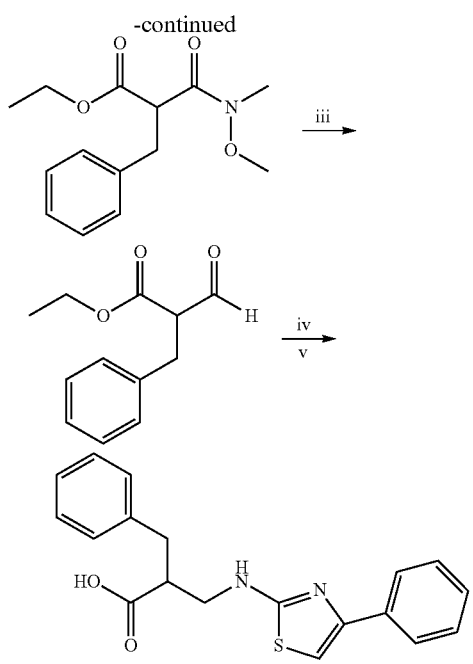

i. KOHaq, EtOH, 16 h, rt; ii. HNMe(OMe), pyBOP, rt; iii. LiAlH₄, THF, 0° C.; iv. 2-amino-4-phenylthiazole, TiCl(OiPr)₃, NaBH(OAc)₃, DCM; v. KOHaq, EtOH, 16 h, rt.

Scheme 7 (method G)

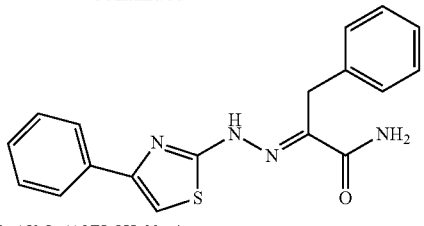

i. a) IBCF, NMM, DME, -15° C.; b) NH₄OH, 20 min

Assignment of Z- and E-Isomers

High-resolution $^1$H NMR spectroscopy revealed that the condensation product that in DMSO-d6 existed as a mixture of E and Z isomers pertaining to the stereochemistry of the carbon-nitrogen double bond. In most of the cases (except 4m) the pure E or Z isomers can be separated by using preparative HPLC with a $C_{18}$ reverse phase column. Assignment of the stereochemistry was based upon the consideration that in the E isomer, the NH group and the $CH_2$ (Z-4c, $\delta_H$=3.75 ppm, $\delta_c$=31.6 ppm) attached to C=N are in proximity, resulting in an upheld shift compared to the chemical shift of Z isomer (E-4c, $\delta_H$=4.04 ppm, $\delta_c$=35.6 ppm), this shift being due to the known γ-steric affect. In this case (4c) E is the predominant isomer. Variation in isomeric rations might be due to the different sizes of $R_3$ and $R_4$ group. This result is consistent with the report by Dimmock and Rezessy. However, they also both reported that the pure E isomers underwent E to Z isomerization after standing in solutions. In order to check the stability of the pure isomers to determine if there is transformation into Z/E mixtures in physiological condition, solution were prepared in deutered eIF4E buffer and spectra were recorded by high resolution $^1$H NMR after dissolution of pure isolated isomers as well as 1 h, 1 day. Interestingly, the testing revealed that they are stable configurationally.

TABLE 1

Comparison of percentage, retention time on HPLC, NMR chemical shift of Z and E-isomers and biological results.

| Synthetic strategy Method | Isomers | | Ratio (%) | Ha δ (ppm) | $IC_{50}$ (μM)[a] (4E/4G FP) | $GI_{50}$[b] (SRB μM) |
|---|---|---|---|---|---|---|
| A | (structure: HOOC-C(=N-NH-thiazole-4-(3,4-dichlorophenyl))-CH₂-(2-nitrophenyl)) | Z-1 | 60.6 | 4.12 δc 30.1 | 400 | 5 ± 1 |
|   |   | E-1 | 39.4 | 4.28 δc 36.9 | 410 | 3 |
| A | (structure: HOOC-C(=N-NH-thiazole-4-phenyl)-CH₂-(2-nitrophenyl)) | Z-2 | 53.1 | 4.15 | >600 | >20 |
|   |   | E-2 | 46.9 | 4.22 | >600 | 7 |

TABLE 1-continued

Comparison of percentage, retention time on HPLC, NMR chemical shift of Z and E-isomers and biological results.

| Synthetic strategy Method | Isomers | Ratio (%) | Ha δ (ppm) | IC$_{50}$ (μM)[a] (4E/4G FP) | GI$_{50}$[b] (SRB μM) |
|---|---|---|---|---|---|
| A | Z-3 | 13.8 | 3.68 | 300 | 14 |
|   | E-3 | 86.2 | 4.02 | 355 | 6.5 |
| A | Z-4 | 8.8 | 3.74 δc | 240 | >20, 17 |
|   | E-4 | 91.2 | 4.05 δc 31.7 | >600 | 14, 17 |
| A | Z-5 | 97.7 | 3.58 | >600 | 7 |
|   | E-5 | 2.3 | 3.74 | — | — |
| A | Z-6 | 40.0 | — | >600 | 13, 13 |
|   | E-6 | 60.0 | — | >600 | 10 |
| A | Z-7 | 33.0 | 2.07 | >600 | >20 |
|   | E-7 | 67.0 | 2.10 | >600 | >20 |
| A | E:Z = 5:2 (8) | — | — | 550 | >10 |

TABLE 1-continued
Comparison of percentage, retention time on HPLC, NMR chemical shift of Z and E-isomers and biological results.
| Synthetic strategy Method | Isomers | | Ratio (%) | Ha δ (ppm) | IC$_{50}$ (μM)$^a$ (4E/4G FP) | GI$_{50}$$^b$ (SRB μM) |
|---|---|---|---|---|---|---|
| A | 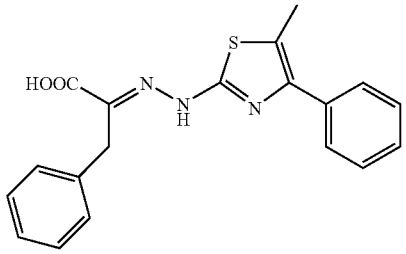 | Z-9<br>E-9 | 17.8<br>82.2 | 3.73<br>4.00 | 240<br>>300 | 4<br>6 |
| A | 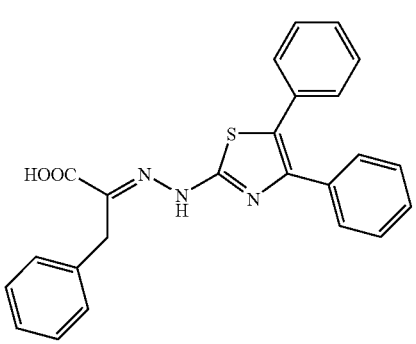 | Z-10<br>E-10 | 25.7<br>74.3 | 3.73<br>4.04 | 50, 50<br>100, 88 | 1<br>1.5 |
| A | 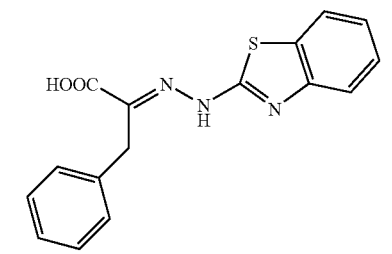 | Z-11<br>E-11 | 14.2<br>85.8 | 3.78<br>4.05 | >600<br>>600 | >20<br>4 |
| A' | 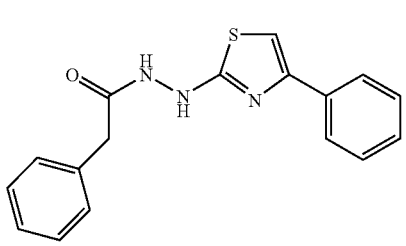 | 12 | — | — | >600 | >20 |
| A" | 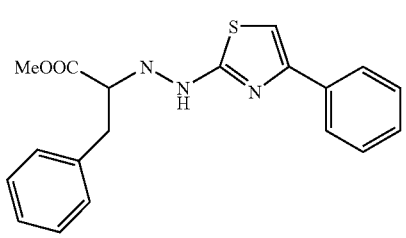 | Z-13<br>E-13 | —<br>— | 3.79<br>4.08 | >600<br>>600 | 11<br>7 |

TABLE 1-continued
Comparison of percentage, retention time on HPLC, NMR chemical shift of Z and E-isomers and biological results.
| Synthetic strategy Method | Isomers | Ratio (%) | Ha δ (ppm) | IC$_{50}$ (μM)[a] (4E/4G FP) | GI$_{50}$[b] (SRB μM) |
|---|---|---|---|---|---|
| A''' | 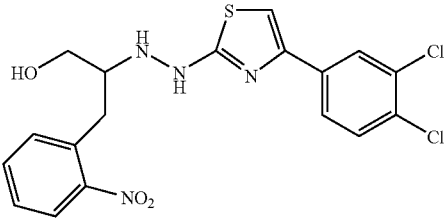 | 14 | — | — | >600 | 4 |
| A''' | 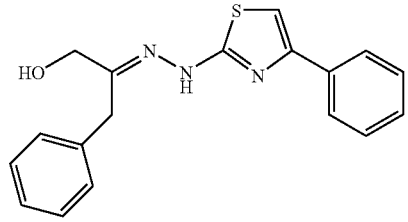 | Z-15 | — | — | >600 | 14 |
| B | 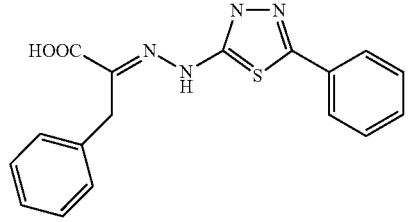 | Z-16 | 16.6 | 3.76 | >600 | >10 |
|   |   | E-16 | 83.4 | 4.05 | >600 | 9 |
| B | 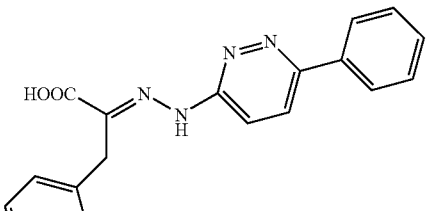 | Z-17 | 24.5 | 3.80 | >600 | >10 |
|   |   | E-17 | 74.0 | 4.20 | >600 | 7.5 ± 1.5 |
| C | 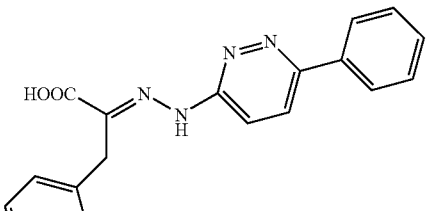 | 18 | — | — | >600 |   |
| D | 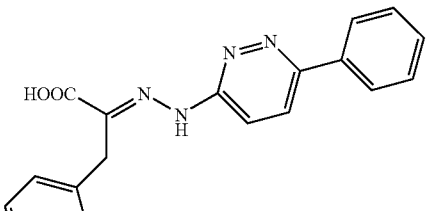 | 19 | — | — | >600 |   |

TABLE 1-continued

Comparison of percentage, retention time on HPLC, NMR chemical shift of Z and E-isomers and biological results.

| Synthetic strategy Method | Isomers | Ratio (%) | Ha δ (ppm) | $IC_{50}$ (μM)[a] (4E/4G FP) | $GI_{50}$[b] (SRB μM) |
|---|---|---|---|---|---|
| E | [structure] | 20 | — | — | insoluble |
| F | [structure] | E-21 | — | — | >600 |
| G | [structure] | 22 | — | — | >600 |
| Commercial | [structure] | 23 | — | — | >600 |

[a]$IC_{50}$ was measured by fluorescent polarization assay. The values indicate the average concentration needed to inhibit 50% of ceIF4E/EIF4G interaction. The experiments were done in triplicate with SD< ± 10%., using eIE4GII peptide and DMSO as the positive and negative controls, respectively.
[b]$GI_{50}$ was measured using sulforhodamine B assay. The values indicate the average concentration needed to inhibit 50% of cell proliferation. The experiments were done in triplicate with SD< ± 10% Using CLT and DMSO as the positive and negative controls, respectively.

In some cases, the configurational isomers differ in the biological activity (Table 1). From a limited SAR study we have shown that Z-2-{[(4,5-diphenyl)-thiazol-2-yl]-hydrazono}-3-phenyl)-propionic acid is two-fold more potent than its E isomer. In the eIF4E/4G assay, this compound is one order of magnitude more potent that the initial hit (Table 1). In addition, modifications made to the carboxyl and imine functions suggest that these are important structural features for bioactivity.

The eIF4E/eIF4G interaction represents the first molecular target for which we have a preliminary comparison of NMR spectra in the presence and absence of ligand. From these NMR studies we were able to identify partially overlapping interaction sites for both lead compounds.

$^1$H NMR spectra were recorded at 500 MHz on a Varian VX500 or at 400 MHz on a Varian VX400 instrument in d-DMSO as solvents. TLC analyses were performed on Kieselgel 60 F254 silica gel plates purchased from EMD chemicals, INC. with UV illumination at 254 nm. Column chromatography was performed on Baker 7024 flash silica gel. Melting points were measured in Pyrex capillary tubes in a Mel-Temp "Elactronthermal" apparatus and are not corrected. LC-MS was performed in Waters LC-MS (APCI mode) with XTerra $C_8$ 30×100mm column. Elemental analyses were obtained only for the final products, and were performed by Robertson Laboratories, Madison, N.J., and were within ±0.4% of theoretical values. All the starting materials were purchased commercially available and used without further purification.

Procedure for synthesis 2-{[4-(3,4-Dichloro-phenyl)-thiazol-2-yl]-hydrazono}-3-(2-nitro-phenyl)-propionic acid (Method A)

4-(3,4-Dichloro-phenyl)-thiazol-2-yl-hydrazine (1a, 3a, 14a)

A solution of a thiosemicarbazide (10 mmol, 0.91 g) and 3,4-dichlorophenylacetyl bromide (10 mmol, 2.68 g) in dioxane (20 mL) was stirred at room temperature for 16 h. The precipitate of hydrobromide salt was filtered and washed with dioxane (3×10 mL), then basified with 2N $Na_2CO_3$ (20 mL). The product was filtered, washed with water and dried (2.08 g, 80%). The product was generally satisfactory for further reaction.

$^1$H NMR (400 MHz, DMSO-d$_6$) δ 8.67 (s, 1H, NH), 8.00 (d, J=1.6 Hz, 1H), 7.76 (dd, J=1.6 Hz, J=8.4 Hz, 1H), 7.60 (d, J=8.4 Hz, 1H), 7.31 (s, 1H).

MS (APCI) (C$_9$H$_7$Cl$_2$N$_3$S) ([M+H]$^+$: found m/z, 259.68; calcd, 259.97.

Anal. Calcd for C$_9$H$_7$Cl$_2$N$_3$S: C, 41.55; H, 2.71; N, 16.15; S, 12.33; Found: C, H, N.

2-{[4-(3,4-Dichloro-phenyl)-thiazol-2-yl]-hydrazono}-3-(2-nitro-phenyl)-propionic acid (1b)

3-(2-Nitro-phenyl)-2-oxo-propionic acid (1.0 mmol, 209 mg) in 5% acetic acid (2 mL) was added in to solution of 4-(3,4-dichloro-phenyl)-thiazol-2-yl-hydrazine (1.0 mmol, 259 mg) in ethanol (4 mL). The reaction mixture was stirred at 90° C. for 1 h and cooled to 0° C.; the orange solid was precipitated, filtered and washed by water. Recrystallization from MeOH—H$_2$O afford the final product as a yellow power (600 mg, 66.7%). mp; Z/E isomer was further separated by HPLC-MS, using gradient eluting solvents: 0.05% HOAc in acetonitrile 50% : 0.05% HOAc in water 50% to 0.05% HOAc in acetonitrile 75%: 0.05% HOAc in water 25% in 20 min.

E-isomer: $^1$H NMR (400 MHz, DMSO-d$_6$) δ 12.85 (br, 1H), 12.10 (br, 1H), 8.06 (d, J=8.4 Hz, 1H), 8.03(s, 1H), 7.78 (d, J=8.4 Hz, 1H), 7.64 (d, J=6.0 Hz , 2H), 7.61(s, 1H), 7.50 (t, J=7.6 Hz, 1H), 7.06 (d, J=7.6 Hz, 1H), 4.28 (s, 2H).

Z-isomer: $^1$H NMR (400 MHz, DMSO-d$_6$) δ 12.35 (br, 1H), 12.10 (br, 1H), 8.03 (d, J=8.4 Hz, 1H), 8.00 (s, 1H), 7.79 (d, J=8.4 Hz, 1H), 7.66 (d, J=6.0 Hz, 2H), 7.62 (s, 1H), 7.50 (t, J=7.6 Hz, 1H), 7.08 (d, J=7.6 Hz, 1H), 4.12 (s, 2H).

Anal. Calcd for C$_{18}$H$_{12}$Cl$_2$N$_4$O$_4$S: C, 47.91; H, 2.68; N, 12.41; Found: C, 47.41; H, 2.59; N, 11.98.

MS (APCI) (C$_{18}$H$_{12}$Cl$_2$N$_4$O$_4$S) ([M+H]$^+$: found m/z, 450.91; calcd, 451.00.

2-[(4-phenyl)-thiazol-2-yl)-hydrazono]-3-(2-nitrophenyl)-propionic acid (2b)

Z/E isomer was further separated by HPLC-MS, using gradient eluting solvents: 0.05% NH$_4$OAc in acetonitril 50%: 0.05% NH$_4$OAc in water 50% to 0.05% NH$_4$OAc in acetonitrile 75%: 0.05% NH$_4$OAc in water 25% in 30 min.

E-isomer: $^1$H NMR (500 MHz, DMSO-d$_6$) δ 8.01 (d, J=8.5 Hz, 1H), 7.80 (d, J=6.5 Hz, 2H), 7.61 (t, J=8.0 Hz, 1H), 7.46 (t, J=8.5 Hz, 1H), 7.37 (t, J=8.0 Hz, 2H), 7.28 (s, 1H), 7.25 (t, J=7.5 Hz, 1H), 7.15 (d, J=7.5 Hz, 1H), 4.26 (s, 2H).

Z-isomer: $^1$H NMR (500 MHz, DMSO-d$_6$) δ 8.03 (d, J=8.0 Hz, 1H), 7.80 (d, J=7.0 Hz, 2H), 7.69 (t, J=8.0 Hz, 1H), 7.52 (m, 2H), 7.38 (t, J=8 Hz, 2H), 7.29 (t, J=7.5 Hz, 1H), 7.26 (s, 1H), 4.15 (s, 2H).

MS (APCI) (C$_{18}$H$_{14}$N$_4$O$_4$S) ([M+H]$^+$: found m/z, 383.04; calcd, 383.07.

Anal. Calcd for C$_{18}$H$_{14}$N$_4$O$_4$S: C, 56.54; H, 3.69; N, 14.65; Found: C, 56.35; H, 3.51; N, 14.45.

2-{[4-(3,4-Dichloro-phenyl)thiazol-2-yl]-hydrazono}-3-phenyl-propionic acid (3b)

Z/E isomer was further separated by HPLC-MS, using gradient eluting solvents: 0.05% NH$_4$OAc in acetonitril 50%: 0.05% NH$_4$OAc in water 50% to 0.05% NH$_4$OAc in acetonitrile 75%: 0.05% NH$_4$OAc in water 25% in 30 min.

E-isomer: $^1$H NMR (300 MHz, DMSO-d$_6$) δ 8.07(d, J=2 Hz, 1H), 7.82 (dd, J=8.5 Hz, J=2 Hz, 1H), 7.66 (m, 2H), 7.24 (m, 5H), 4.02 (s, 2H).

Z-isomer: $^1$H NMR (300 MHz, DMSO-d$_6$) δ 8.11 (dd, J=20 Hz, J=2 Hz, 1H), 7.83 (dd, J=8.5 Hz, J=2 Hz, 1H), 7.64 (m, 1H), 7.46 (s, 1H), 7.30-7.14 (m, 5H), 3.68 (s, 2H).

MS (APCI) (C$_{18}$H$_{13}$Cl$_2$N$_3$O$_2$S) ([M+H]$^+$: found m/z, 406.07; calcd, 406.01.

Anal. Calcd for C$_{18}$H$_{13}$Cl$_2$N$_3$O$_2$S: C, 53.21; H, 3.23; N, 10.34; Found: C, 53.34; H, 3.45; N, 10.40.

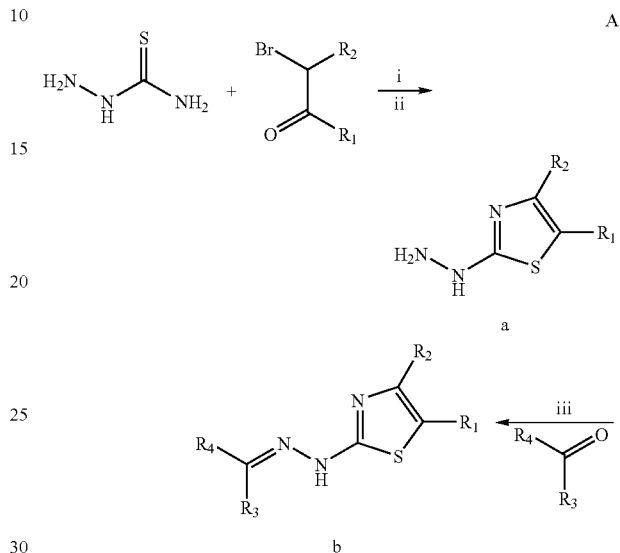

2-[(5-Methyl-4-phenyl-thiazol-2-yl)-hydrazono]-3-phenyl-propionic acid (9b)

Yield=92%.

E-isomer: $^1$H NMR (400 MHz) δ 7.58 (d, J=7.5 Hz, 2H), 7.43 (t, J=7.5 Hz, 2H), 7.31 (m, 3H), 7.20 (m, 3H), 3.73 (s, 2H), 2.48 (s, 3H).

Z-isomer: $^1$H NMR (400 MHz) δ 7.58 (d, J=7.5 Hz, 2H), 7.41 (t, J=7.5 Hz, 2H), 7.29 (m, 3H), 7.18 (m, 3H), 4.00 (s, 2H), 2.48 (s, 3H).

MS (ESI) (C$_{19}$H$_{17}$N$_3$O$_2$S) ([M+H]$^+$: found m/z, 352.15; calcd, 352.10.

Anal. Calcd for C$_{19}$H$_{17}$N$_3$O$_2$S: C, 64.94; H, 4.88; N, 11.96; Found: C, H, N.

2-[(4,5-Diphenyl-thiazol-2-yl)-hydrazono]-3-phenyl-propionic acid (10b)

Yield=90%.

E-isomer: $^1$H NMR (400 MHz) δ 7.90-7.15 (m, 15H), 4.20 (s, 2H).

Z-isomer: $^1$H NMR (400 MHz) δ 7.45-7.15 (m, 15H), 3.68 (s, 2H).

MS (ESI) (C$_{24}$H$_{19}$N$_3$O$_2$S) ([M+H]$^+$: found m/z, 414.0; calcd, 414.1.

Anal. Calcd for C$_{24}$H$_{19}$N$_3$O$_2$S: C, 69.71; H, 4.63; N, 10.16; Found: C, H, N.

Phenyl-[(4-phenyl-thiazol-2-yl)-hydrazono]-acetic acid (6b)

Yield=40%.

E-Z isomer: $^1$H NMR (500 MHz) δ 7.84 (m, 2H), 7.65 (m, 2H), 7.43-7.28 (m, 7H).

MS (ESI) ($C_{17}H_{13}N_3O_2S$) ([M+H]$^+$: found m/z, 324.1; calcd, 324.1.

Anal. Calcd for $C_{17}H_{13}N_3O_2S$: C, 63.14; H, 4.05; N, 12.99; Found: C, H, N.

3-Phenyl-2-[(4-phenyl-thiazol-2-yl)-hydrazono]-propionic acid (4b)

Yield: 65%

E-isomer: $^1$H NMR (400 MHz) δ 7.83 (d, J=7.5 Hz, 2H), 7.40 (dd, J=12 Hz, J=4.5 Hz, 4H), 7.29 (t, J=7.5 Hz, 3H), 7.19 (d, J=7.5 Hz, 2H), 4.05 (s, 2H).

Z-isomer: $^1$H NMR (400 MHz) δ 7.84 (d, J=7.0 Hz, 2H), 7.40 (m, 3H), 7.30 (m, 3H), 7.20 (d, J=7.0 Hz, 2H), 3.75 (s, 2H).

MS (ESI) ($C_{18}H_{15}N_3O_2S$) ([M+H]$^+$: found m/z, 338.0; calcd, 338.1.

Anal. Calcd for $C_{18}H_{15}N_3O_2S$: C, 64.08; H, 4.48; N, 12.45; Found: C, H, N,

N-Phenethylidene-N'-(4-phenyl-thiazol-2-yl)-hydrazine (5b)

Yield=73%.

E-isomer: $^1$H NMR (400 MHz) δ 7.83 (b, 2H), 7.49 (t, J=3.6 Hz, 4H), 7.29-7.18 (m, 6H), 4.03 (s, 2H).

Z-isomer: $^1$H NMR (500 MHz) δ, 7.87 (d, J=8 Hz, 1H), 7.83 (d, J=8 Hz, 1H), 7.44-7.22 (m, 10H), 3.59 (d, J=6 Hz, 2H).

MS (ESI) ($C_{17}H_{15}N_3S$) ([M+H]$^+$: found m/z, 294.0; calcd, 294.1.

Anal. Calcd for $C_{17}H_{15}N_3S$: C, 69.59; H, 5.15; N, 14.32; Found: C, H, N.

2-[(4-Phenyl-thiazol-2-yl)-hydrazono]-propionic acid (7b)

Yield: 99%

E-isomer: $^1$H NMR (400 MHz) δ 7.84 (d, J=7.2 Hz, 2H), 7.45-7.36 (m, 3H), 7.30 (m, 1H), 3.38 (s, 2H), 2.10 (s, 3H).

Z-isomer: $^1$H NMR (400 MHz) δ 7.84 (d, J=7.2 Hz, 2H), 7.40 (t, J=8 Hz, 3H), 7.30 (t, J=7.2 Hz 1H), 3.32 (s, 2H), 2.07 (s, 3H).

MS (ESI) ($C_{12}H_{11}N_3O_2S$) ([M+H]$^+$: found m/z, 261.9; calcd, 262.0.

Anal. Calcd for $C_{12}H_{11}N_3O_2S$: C, 55.16; H, 4.24; N, 16.08; Found: C, H, N,

(8b)

Yield: 75%

E-Z isomer: $^1$H NMR (500 MHz) δ 11.24 (s, 1H), 7.37-7.16 (m, 11H), 4.82 (d, 2H), 4.18 (s, 2H).

MS (APCI) ($C_{17}H_{17}N_3O_2S$) ([M+H]$^+$: found m/z, 328.01; calcd, 328.10.

Anal. Calcd for $C_{17}H_{17}N_3O_2S$: C, 62.36; H, 5.23; N, 12.83; Found: C, H, N,

2-(Benzothiazol-2-yl-hydrazono)-3-phenyl-propionic acid (11b)

Yield: 66%

E-isomer: $^1$H NMR (400 MHz) δ 7.70 (d, J=7.2 Hz, 1H), 7.30-7.11 (m, 8H), 4.02 (s, 2H).

Z-isomer: $^1$H NMR (400 MHz) δ 7.77 (d, J=7.2 Hz, 1H), 7.42 (d, J=8 Hz, 1H), 7.32-7.11 (m, 7H), 3.70 (s, 2H).

MS (APCI) ($C_{16}H_{13}N_3O_2S$) ([M+H]$^+$: found m/z, 311.91; calcd, 312.07.

Anal. Calcd for $C_{16}H_{13}N_3O_2S$: C, 61.72; H, 4.21; N, 13.50; Found: C, H, N,

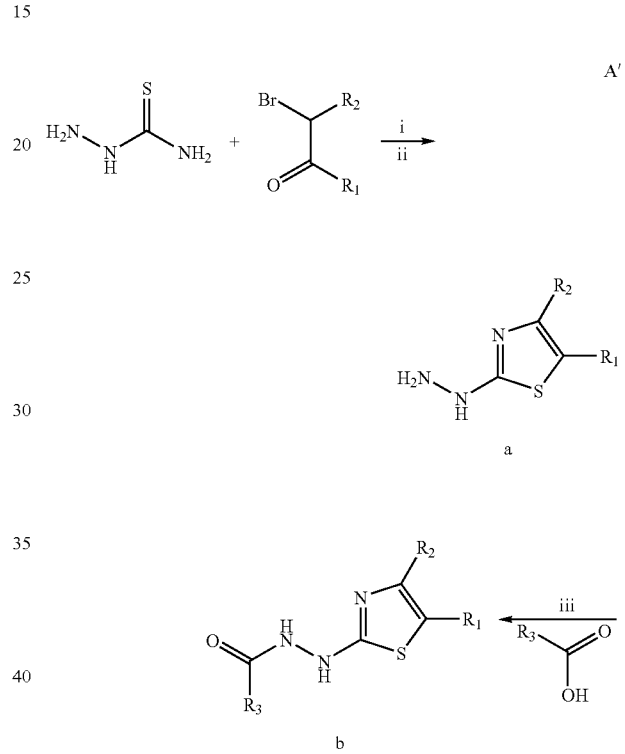

Phenyl-acetic acid N'-(4-phenyl-thiazol-2-yl)-hydrazide (12b)

To a suspension of (5-Phenyl-thiazol-2-yl)-hydrazine (96 mg, 0.5 mmol) and 1-[3-(dimethylamino)propyl]-3-ethylcarbodiimide hydrochloride (0.44 mmol) in DMF (4 mL) at 25° C. was added phenyl acetic acid (55 mg, 0.4 mmol), the resulting mixture was stirring at 25° C. for overnight and concentrated in vacuo, and the residue was dissolved in $CH_2Cl_2$ (20 mL) was washed with 5% $NaHCO_3$, dried with $MgSO_4$ and concentrated in vacuo. The residue was purified by HPLC. The product was obtained 155 mg (51%) as white solid.

$^1$H NMR (400 MHz) δ 7.77 (d, J=7.5 Hz, 2H), 7.38-7.21 (m, 9H), 3.49 (s, 2H).

MS (ESI) ($C_{17}H_{15}N_3OS$) ([M+H]$^+$: found m/z, 310.0; calcd, 310.1.

Anal. Calcd for $C_{17}H_{15}N_3OS$: C, 66.00; H, 4.89; N, 13.58; Found: C, H, N,

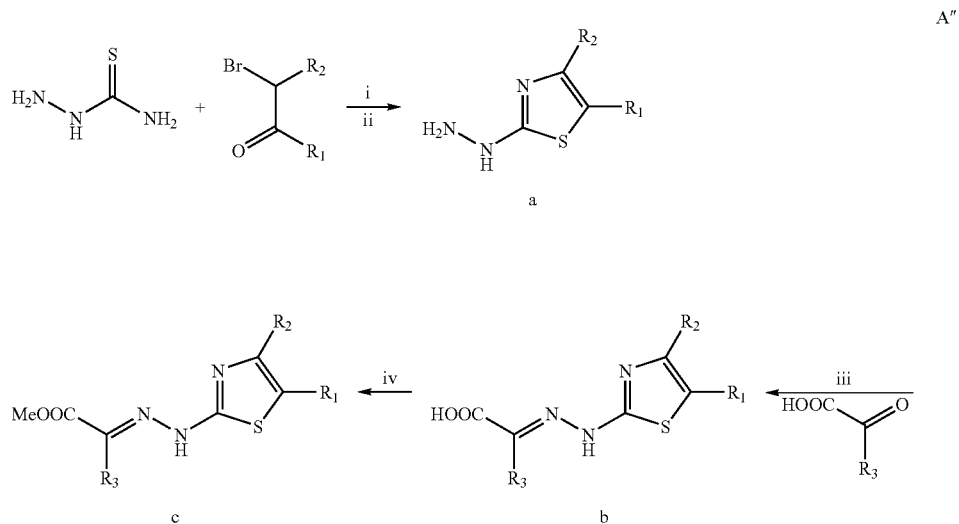

3-Phenyl-2-[(4-phenyl-thiazol-2-yl)-hydrazono]-propionic acid methyl ester (13c)

To a suspension of 4b (0.1 mmol, 34 mg) in MeOH (2 mL), was added dropwise thionylchloride (22 μL, 0.3 mmol) at −30° C. Then, the solution was allowed to warm at room temperature. The reaction mixture was heated to reflux and concentrated to afford the desired product. The crude is purified by silica gel chromatography (EtOAc/MeOH 10/1) to give the pure compound as a yellow solid (11 mg, 32%).

E-isomer: $^1$H NMR (300 MHz) δ 7.84 (d, J=7.8 Hz, 2H), 7.40 (m, 4H), 7.28 (t, J=7.5 Hz, 3H), 7.19 (d, J=7.5 Hz, 2H), 4.07 (s, 2H), 3.72 (s, 3H).

Z-isomer: $^1$H NMR (300 MHz) δ 7.85 (d, J=7.0 Hz, 2H), 7.48 (s, 1H), 7.39 (t, J=7.0 Hz, 2H), 7.33-7.28 (m, 3H), 7.22 (d, J=7.0 Hz, 3H), 3.78 (s, 2H), 3.76 (s, 3H).

MS (APCI) ($C_{19}H_{17}N_3O_2S$) ([M−H]$^-$: found m/z, 349.96; calcd, 350.10.

Anal. Calcd for $C_{19}H_{17}N_3O_2S$: C, 64.94; H, 4.88; N, 11.96; Found: C, H, N.

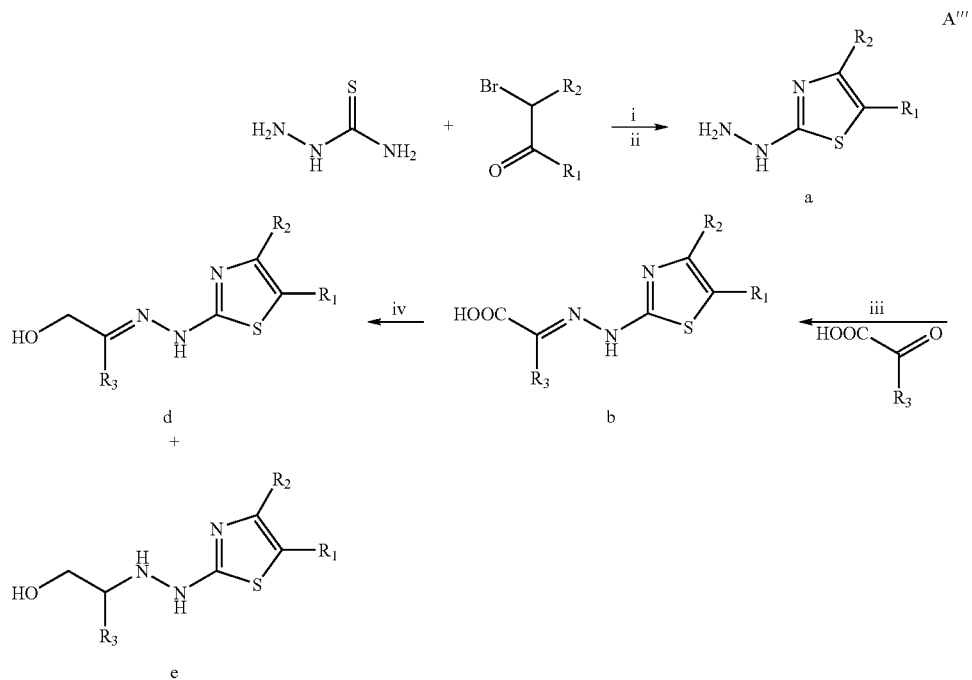

2-{N'-[4-(3,4-Dichloro-phenyl)-thiazol-2-yl]-hydrazino}-3-(3-nitro-phenyl)-propan-1-ol (14e)

To a solution of 1b (90 mg, 0.2 mmol) in THF (2 ml) was added BH$_3$.SMe$_2$ 1M in THF (2 mmol, 10 eq). The solution was stirred at room temperature for 2 hours. Then, the reaction was quenched with water, and extracted with AcOEt. The organic solution is dried (Na$_2$SO$_4$) and concentrated to give a $^1$H NMR (400 MHz) δ 7.98 (d, J=7.5 Hz, 2H), 7.70 (s, 1H), 7.42 (t, J=7.5 Hz, 2H), 7.31 (m, 6H), 5.79 (s, 2H), 3.49 (s, 2H).

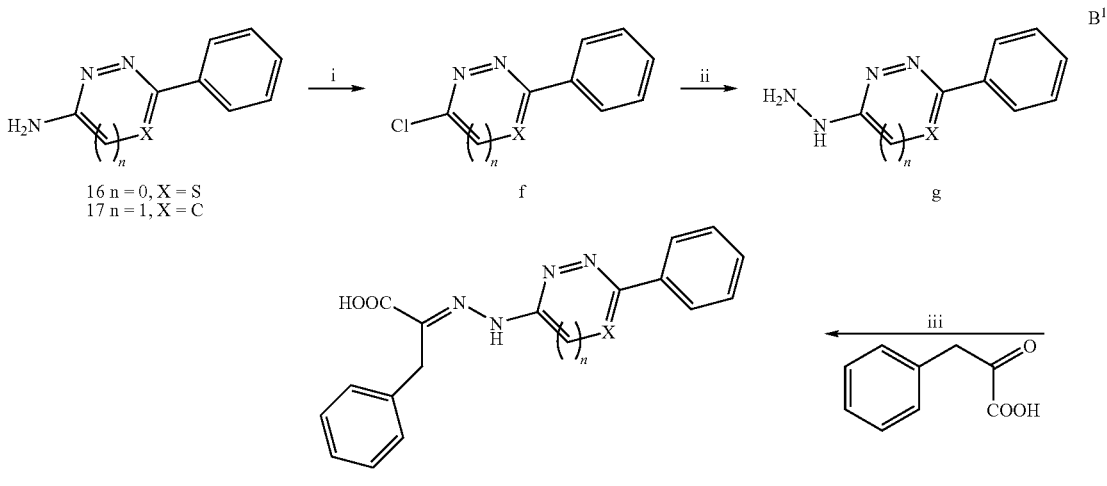

16 n = 0, X = S
17 n = 1, X = C

[1] S. Turner; M. Myers; B. Gadie; A.J. Nelson; R. Pape; J.F. Saville; J.C. Doxey; and T.L. Berridge; Antihypertensive thiadiazoles. 1. Synthesis of some 2-aryl-5-hydrazino-1,3,4-thiadiazoles with vasodilator activity; *J. Med. Chem.*; 1988; 31(5), 902-906.

mixture of 7b and 8b. Each product was purified by silica gel chromatography (EtOAc/MeOH 10/1) to give the pure compounds 14d (27 mg, 31%) and 14e (11 mg, 13%).

2-{[4-(3,4-Dichloro-phenyl)-thiazol-2-yl]-hydrazono}-3-(2-nitro-phenyl)-propan-1-ol (14d)

(Compound Not Tested)
E-isomer: $^1$H NMR (300 MHz) δ 8.0-7.98 (m, 2H), 7.75-7.47 (m, 5H), 7.35 (s, 1H), 4.32 (d, 2H), 4.07 (s, 2H).
Z-isomer: $^1$H NMR (300 MHz)
MS (ESI) (C$_{18}$H$_{14}$Cl$_2$N$_4$O$_3$S) ([M+H]$^+$: found m/z, 437.2; calcd, 437.0.
Anal. Calcd for C$_{18}$H$_{14}$Cl$_2$N$_4$O$_3$S: C, 49.44; H, 3.23; N, 12.81; Found: C, H, N, 2-{N'-[4-(3,4-Dichloro-phenyl)-thiazol-2-yl]-hydrazino}-3-(2-nitro-phenyl)-propan-1-ol (14e)

$^1$H NMR (300 MHz) δ 7.95 (d, J=1.5, 1H), 7.91-7.89 (dd, J=1.5 Hz, J=8 Hz, 1H), 7.73-7.43 (m, 5H), 7.22 (s, 1H), 4.73 (t, 1H), 3.47 (m, 2H), 2.95 (m, 2H).
MS (ESI) (C$_{18}$H$_{16}$Cl$_2$N$_4$O$_3$S) ([M+H]$^+$: found m/z, 439.2; calcd, 439.0.
Anal. Calcd for C$_{18}$H$_{16}$Cl$_2$N$_4$O$_3$S: C, 49.21; H, 3.67; N, 12.75; Found: C, H, N.

3-Phenyl-2-[(4-phenyl-thiazol-2-yl)-hydrazono]-propan-1-ol (15d)

Same experimental conditions than above with 4b (200 mg, 0.6 mmol) as a starting material; the pure product is obtained after purification with a yield of 25% (47 mg).
Z-isomer: $^1$H NMR (300 MHz) δ 7.76 (d, J=7.2 Hz, 2H), 7.20-7.39 (m, 8H), 7.08 (s,1H), 3.92 (d, J=5.1 Hz, 2H), 3.30 (d, J=6.9 Hz, 2H).
MS (ESI) (C$_{18}$H$_{17}$N$_3$OS) ([M+H]$^+$: found m/z, 323.1; calcd, 323.1.
Anal. Calcd for C$_{18}$H$_{17}$N$_3$OS: C, 66.85; H, 5.30; N, 12.99; Found: C, H, N, 2-Chloro-5-phenyl-[1,3,4]thiadiazole (16f)

To a stirred suspension of 2-aminothiadiazole (885 mg, 5 mmol) and copper turnings (0.1 time the weight of 4) in a concentrated HCl (3 mL) and glacial AcOH (15 mL) at 15° C. was added dropwise a solution of sodium nitrite (380 mg, 5.5 mmol) in water (1 mL) over 30 min. After being stirred at this temperature for an additional 4 h, the mixture was poured into water. The product was extracted into CHCl$_3$. The organic phase was separated, washed with NaHCO$_3$ solution, dried (Na$_2$SO$_4$), and evaporated to give the corresponding 2-Chloro-5-phenyl-[1,3,4]thiadiazole (729 mg, 68%).
$^1$H NMR (400 MHz) δ 7.94 (dd, J=7.6 Hz, J=1.5 Hz, 2H), 7.54-7.60 (m, 3H).
MS (APCI) (C$_8$H$_5$ClN$_2$S) ([M+H]$^+$: found m/z, 196.88; calcd, 195.99.
Anal. Calcd for C$_8$H$_5$ClN$_2$S: C, 48.86; H, 2.56; N, 14.24; Found: C, H, N, 2-phenyl-5-hydrazino-1,3,4-thiadiazole (16g)

A solution of the 2-Chloro-5-phenyl-[1,3,4]thiadiazole (2 mmol) and hydrazine hydrate (6 mmol, 3 eq) in iPrOH (10 mL) was heated at reflux overnight. The solvent was evaporated, water was added, and the product was isolated by filtration (110 mg, 57%).
MS (APCI) (C$_8$H$_8$N$_4$S) ([M+H]$^+$: found m/z, 192.96; calcd, 193.05.
Anal. Calcd for C$_8$H$_8$N$_4$S: C, 49.98; H, 4.19; N, 29.14; Found: C, H, N, 3-Phenyl-2-[(5-phenyl-[1,3,4]thiadiazol-2-yl)-hydrazono]-propionic acid (16h)

2-Oxo-3-phenyl-propionic acid (1.0 mmol, 164 mg) in 5% acetic acid was added to a solution of 2-phenyl-5-hydrazino-1,3,4-thiadiazoles (1.0 mmol, 192 mg) (2 mL) in ethanol (4 mL). The reaction mixture was stirred at 90° C. for 2 h and cooled to 0° C.; the solid was precipitated out, filtered and washed by water. Recrystallization from MeOH—H$_2$O affords the final product as a powder (278 mg, 82%).

E-isomer: $^1$H NMR (500 MHz) δ 7.85 (b, 2H), 7.52 (t, J=3.5 Hz, 3H), 7.30 (t, J=7.5 Hz, 2H), 7.21 (d, J=7.5 Hz, 3H), 7.22 (d, J=7.0 Hz, 3H), 4.04 (s, 2H).

Z-isomer: $^1$H NMR (500 MHz) δ 7.86 (d, J=3.5 Hz, 2H), 7.52 (m, 3H), 7.34-7.20 (m, 5H), 3.79 (s, 2H).

MS (APCI) (C$_{17}$H$_{14}$N$_4$O$_2$S) ([M+H]$^+$: found m/z, 338.96; calcd, 339.10.

Anal. Calcd for C$_{17}$H$_{14}$N$_4$O$_2$S: C, 60.34; H, 4.17; N, 16.56; Found: C, H, N, (6-Phenyl-pyridazin-3-yl)-hydrazine (17g) (Intermediate 17f Commercially Available)

Yield-57%

MS (APCI) (C$_{10}$H$_{10}$N$_4$) ([M+H]$^+$: found m/z, 186.99; calcd, 187.09.

Anal. Calcd for C$_{10}$H$_{10}$N$_4$: C, 64.50; H, 5.41; N, 30.09; Found: C, H, N, 3-Phenyl-2-[(6-phenyl-pyridazin-3-yl)-hydrazono]-propionic acid (17h)

Yield=60%

E-isomer: $^1$H NMR (400 MHz) δ 8.35 (b, 2H), 8.04 (d, J=7.6 Hz, 3H), 7.53 (m, 3H), 7.31-7.20 (m, 4H), 4.20 (s, 2H).

Z-isomer: $^1$H NMR (400 MHz) δ 8.19 (d, J=9.6 Hz, 1H), 8.05 (d, J=7.6 Hz, 2H), 7.64 (d, J=9.6 Hz, 1H), 7.7.53-7.44 (m, 3H), 7.32-7.19 (m, 5H), 3.80 (s, 2H).

MS (APCI) (C$_{19}$H$_{16}$N$_4$O$_2$) ([M+H]$^+$: found m/z, 332.90; calcd, 333.13.

Anal. Calcd for C$_{19}$H$_{16}$N$_4$O$_2$: C, 68.66; H, 4.85; N, 16.86; Found: C, H, N.

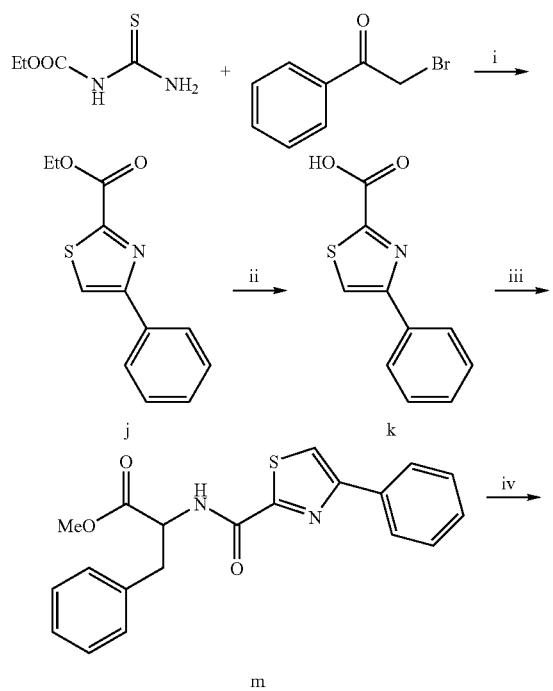

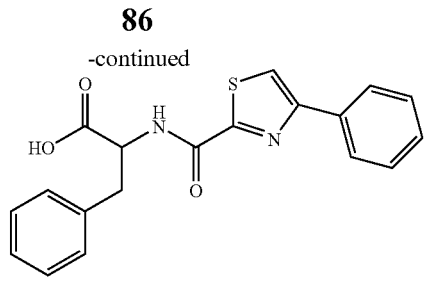

4-Phenyl-thiazole-2-carboxylic acid ethyl ester (18j)

A solution of 2-Bromo-1-phenyl-ethanone (597 mg, 3.0 mmol) and 2-thio-oxamic acid ethyl ester (399 mg, 3.0 mmol) in dioxane (10 ml) was heated under reflux for 1.5 hours. After evaporating the solvent from the reaction mixture, the residue was treated with water, made weak alkaline (pH=8) with saturated aqueous sodium carbonate and extracted with ethyl acetate. The organic phase was washed with saturated saline and dried over anhydrous sodium sulfate, and the solvent was distilled off The residue was dissolved in developing solvent (n-hexane: ethyl acetate=8:2) and applied on silica gel column. The first fraction (impurities) was discarded and the following fraction (colorless solution) was pooled and concentrated to give viscous product, which was crystallized by adding n-hexane. The crystals were filtered with suction to give 328 mg (yield 47%) of 4-phenyl-thiazole-2-carboxylic acid ethyl ester as white solids.

$^1$H NMR (400 MHz) δ 8.50 (s, 1H), 7.98 (d, J=7.6 Hz, 2H), 7.48 (t, J=7.2 Hz, 2H), 7.39 (t, J=7.2 Hz, 1H), 4.40 (q, J=7.2 Hz, 2H), 1.33 (t, J=7.2, 3H).

MS (APCI) (C$_{12}$H$_{11}$NO$_2$S) ([M+H]$^+$: found m/z, 233.96; calcd, 234.05.

Anal. Calcd for C$_{12}$H$_{11}$NO$_2$S: C, 61.78; H, 4.75; N, 6.00; Found: C, H, N.

4-Phenyl-thiazole-2-carboxylic acid (18k)

To a solution of 4-phenyl-thiazole-2-carboxylic acid ethyl ester (282 mg, 1.21 mmol) dissolved in methanol (10 ml) was added 1N—KOH (3.63 ml, 3.63 mmol) and the mixture was allowed to react at 60° C. for 15 minutes. After the solvent was evaporated from the reaction mixture, the residue was dissolved by adding water and acidified (pH=2) with 2N—HCl under ice cooling. The produced precipitates were filtered with suction, washed with water and recrystallized from methanol-water to afford 190 mg (yield 72%) of the desired 4-phenyl-thiazole-2carboxylic acid as white solids.

$^1$H NMR (DMSO-d$_6$); δ 8.46 (s, 1H), 7.98 (d, J=8.4 Hz, 2H), 7.46 (t, J=8.0 Hz, 2H), 7.39 (t, J=7.2 Hz, 1H).

MS (APCI) (C$_{10}$H$_7$NO$_2$S) ([M−H]$^-$: found m/z, 203.88; calcd, 204.02.

Anal. Calcd for C$_{10}$H$_7$NO$_2$S: C, 58.52; H, 3.44; N, 6.82; Found: C, H, N.

3-Phenyl-2-[(4-phenyl-thiazole-2-carbonyl)-amino]-propionic acid methyl ester (18l)

To a suspension of 4-Phenyl-thiazole-2-carboxylic acid (100 mg, 0.4 mmol) and 1-[3-(dimethylamino)propyl]-3-ethylcarbodiimide hydrochloride (0.44 mmol) in DMF (4 mL) at 25° C. was added phenylalanine methyl ester (72 mg, 0.4 mmol), the resulting mixture was stirring at 25° C. for overnight and concentrated in vacuo, and the residue was dissolved in CH$_2$Cl$_2$ (20 mL) was washed with 5% NaHCO3, dried with MgSO4 and concentrated in vacuo. The residue was purified by HPLC. The product was obtained 92 mg (61%) as white solid.

$^1$H NMR (DMSO-d$_6$) δ 9.14 (d, J=8.4 Hz, 1H), 8.41 (s, 1H), 8.06 (d, J=7.6 Hz, 2H), 7.48 (t, J=7.2 Hz, 2H), 7.39 (t, J=7.2 Hz, 1H), 7.26 (m, 4H), 4.76 (t, J=7.2 Hz, 1H), 3.66 (s, 3H), 3.24 (d, J=7.6, 2H).

MS (APCI) (C$_{20}$H$_{18}$N$_2$O$_3$S) ([M+H]$^+$: found m/z, 367.04; calcd, 367.10.

Anal. Calcd for C$_{20}$H$_{18}$N$_2$O$_3$S: C, 65.55; H, 4.95; N, 7.64; Found: C, H, N.

3-Phenyl-2-[(4-phenyl-thiazole-2-carbonyl)-amino]-propionic acid (18m)

To a solution of 3-Phenyl-2-[(4-phenyl-thiazole-2-carbonyl)-amino]-propionic acid methyl ester (74 mg, 0.2 mmol) dissolved in ethanol (4 mL) was added 1N—KOH (0.5 mL, 0.5 mmol) and the mixture was stirred at room temperature for 2 hours. After the solvent was evaporated from the reaction mixture, the residue was dissolved by adding water and acidified (H=2) with 2N—HCl under ice cooling. The produced precipitates were filtered with suction, washed with water to afford 59 mg (yield 80%) of the desired 3-Phenyl-2-[(4-phenyl-thiazole-2-carbonyl)-amino]-propionic acid as white solids.

$^1$H NMR (DMSO-d$_6$) δ 8.93 (d, J=8.4 Hz, 1H), 8.41 (s, 1H), 8.06 (d, J=7.6 Hz, 2H), 7.48 (t, J=7.2 Hz, 2H), 7.39 (t, J=7.2 Hz, 1H), 7.26 (m, 4H), 4.67 (t, J=7.2 Hz, 1H), 3.24 (d, J=5.6 Hz, 2H).

MS (APCI) (C$_{19}$H$_{16}$N$_2$O$_3$S) ([M+H]$^+$: found m/z, 353.04; calcd, 353.09.

Anal. Calcd for C$_{19}$H$_{16}$N$_2$O$_3$S: C, 64.76; H, 4.58; N, 7.95; Found: C, H, N.

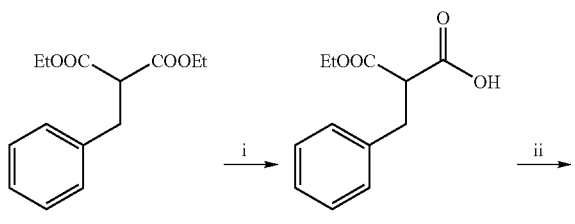

D

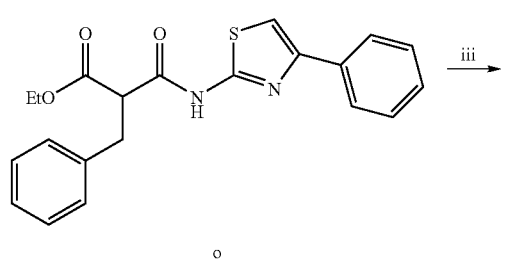

o

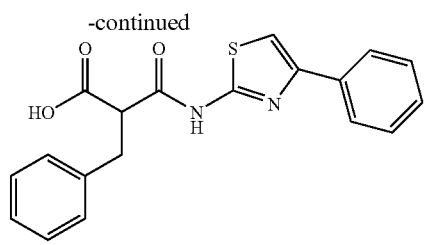

p

2-Benzyl-malonic acid monoethyl ester (19n)

To a solution of 2-benzylmalonic acid diethyl ester 2.5 g (10 mmol) in EtOH (10 mL) was added 1N KOH in EtOH (8.5 mL). The solution was stirred for 1 h at room temperature. The solvent was removed under reduced pressure, and the resulting liquid dissolved in 5% NaHCO$_3$ (30 mL), washed with EtOAc (3×10 mL), and back extracted with 5% NaHCO$_3$ (50 mL). The combined NaHCO$_3$ solutions were acidified to pH=3 with 1N HCl and extracted with EtOAc. The organic layer was washed with H$_2$O, dried with Na$_2$SO$_4$. The solvent was removed under reduced pressure to give final product as oil, 1.4 g (74%).

$^1$H NMR (DMSO-d$_6$) δ 7.17-7.25 (m, 5H), 4.02 (q, J=7.2 Hz, 2H), 3.67 (t, J=7.2 Hz, 1H), 3.04 (dd, J=7.2, J=8.8 Hz, 2H), 1.06 (t, J=7.2 Hz, 3H).

MS (ESI) (C$_{12}$H$_{14}$O$_4$) ([M+H]$^+$: found m/z, 223.4; calcd, 223.2.

Anal. Calcd for C$_{12}$H$_{14}$O$_4$: C, 64.85; H, 6.35; O, 28.80; Found: C, H, N.

2-Benzyl-N-(4-phenyl-thiazol-2-yl)-malonamic acid ethyl ester (19o)

To a suspension of 2-Benzyl-malonic acid monoethyl ester (150 mg, 0.67 mmol) and 1-[3-(dimethylamino)propyl]-3-ethylcarbodiimide hydrochloride (0.74 mmol) in DMF (4 mL) at 25° C. was added 4-phenyl-thiazol-2-ylamine (119 mg, 0.67 mmol), the resulting mixture was stirring at 25° C. for overnight and concentrated in vacuo, and the residue was dissolved in CH$_2$Cl$_2$ (20 mL) was washed with 5% NaHCO3, dried with MgSO4 and concentrated in vacuo. The residue was purified by HPLC. The product was obtained 170 mg (67%) as white solid.

$^1$H NMR (400 MHz, DMSO-d$_6$) δ 7.85 (d, J=8 Hz, 2H), 7.40 (t, J=6.4 Hz, 2H), 7.22 (m, 7H), 4.07 (m, 3H), 3.17 (m, 2H), 1.11 (t, J=6.4 Hz, 3H).

MS (APCI) (C$_{21}$H$_{20}$N$_2$O$_3$S) ([M+H]$^+$: found m/z, 381.21; calcd, 381.46.

Anal. Calcd for C$_{21}$H$_{20}$N$_2$O$_3$S: C, 66.29; H, 5.30; N, 7.36; Found: C, H, N.

2-Benzyl-N-(4-phenyl-thiazol-2-yl)-malonamic acid (19p)

To a solution of 3-Phenyl-2-[(4-phenyl-thiazole-2-carbonyl)-amino]-propionic acid (74 mg, 0.2 mmol) dissolved in ethanol (4 mL) was added 1N—KOH (0.5 mL, 0.5 mmol) and the mixture was stirred at room temperature for 2 hours. After the solvent was evaporated from the reaction mixture, the residue was dissolved by adding water and acidified (pH=2) with 2N—HCl under ice cooling The produced precipitates were filtered with suction, washed with water to afford 59 mg (yield 80%) of the desired 3-Phenyl-2-[(4-phenyl-thiazole-2-carbonyl)-amino]-propionic acid as white solids.

$^1$H NMR (400 MHz, DMSO-d$_6$) δ 7.84(d, J=7.6 Hz, 2H), 7.61 (s, 1H), 7.40 (t, J=8 Hz, 2H), 7.30-7.15 (m, 6H), 3.96 (t, 1H), 3.14 (d, 2H).

MS (APCI) (C$_{19}$H$_{16}$N$_2$O$_3$S) ([M+H]$^+$: found m/z, 353.04; calcd, 353.09.

Anal. Calcd for C$_{19}$H$_{16}$N$_2$O$_3$S: C, 64.76; H, 4.58; N, 7.95; Found: C, H, N.

Anal. Calcd for C$_{19}$H$_{18}$N$_2$O$_2$S: C, 67.43; H, 5.36; N, 8.28; Found: C, H, N.

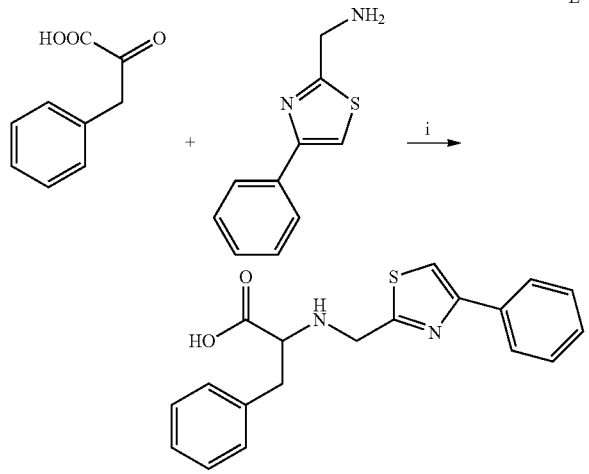

²J. Med. Chem; 1989, 32, 1.

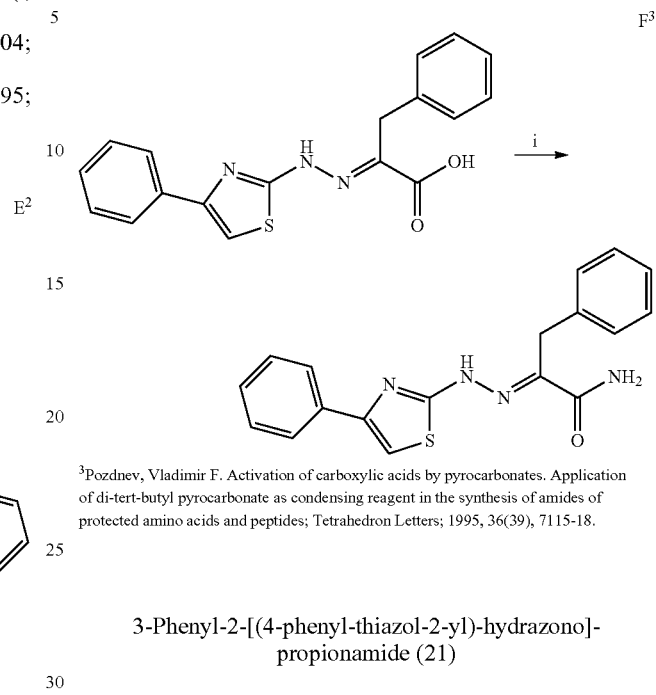

³Pozdnev, Vladimir F. Activation of carboxylic acids by pyrocarbonates. Application of di-tert-butyl pyrocarbonate as condensing reagent in the synthesis of amides of protected amino acids and peptides; Tetrahedron Letters; 1995, 36(39), 7115-18.

3-Phenyl-2-[(4-phenyl-thiazol-2-ylmethyl)-amino]-propionic acid (20)

To a solution of 2-Oxo-3-phenyl-propionic acid (1.6 mmol, 264 mg) and (4-Phenyl-thiazol-2-yl)-methylamine (1.0 mmol, 190 mg) in MeOH (4 mL), is added NaBH$_3$CN (2.0 mmol, 1N in THF). The pH was then adjusted at 6 with 1M HClaq. The mixture was stirred at room temperature for 3 days. The product was purified by HPLC to give the pure product (210 mg, 62%).

$^1$H NMR (400 MHz) δ 7.92 (s, 1H), 7.88 (d, J=7.2 Hz, 2H), 7.39 (t, J=6 Hz, 3H), 7.25 (m, 5H), 4.13 (d, J=16 Hz, 1H), 3.88 (d, J=16 Hz, 1H), 3.44 (t, J=6.4 Hz, 1H), 2.87 (m, 2H).

MS (APCI) (C$_{19}$H$_{18}$N$_2$O$_2$S) ([M+H]$^+$: found m/z, 339.00; calcd, 339.11.

3-Phenyl-2-[(4-phenyl-thiazol-2-yl)-hydrazono]-propionamide (21)

To a solution of 3-Phenyl-2-[(4-phenyl-thiazol-2-yl)-hydrazono]-propionic acid (4b) (1.0 mmol, 337 mg) in DME (5 mL) at −15° C., were added NMM (1.1 mmol, 121 μL), then IBCF (1.1 mmol, 147 μL). Then, a solution of NH$_4$OH concentrated was added and the mixture was stirred for 20 minutes. 5 mL of water was added and the precipitate was filtered and washed with H$_2$O and hexane to give the desired product.

The product was purified by HPLC-MS, with a C$_8$ column, using gradient eluting solvents: 0.05% NH$_4$OAc in acetonitrile 30%: 0.05% NH$_4$OAc in water 70% to 0.05% NH$_4$OAc in acetonitrile 60%: 0.05% NH$_4$OAc in water 40% in 30 min.

E-isomer: $^1$H NMR (300 MHz) in DMSO δ 7.83 (d, J=7.5 Hz, 2H), 7.38 (t, J=7 Hz, 5H), 7.30-7.10 (m, 4H), 4.05 (s, 2H).

MS (ESI) (C$_{18}$H$_{16}$N$_4$OS) ([M+H]$^+$: found m/z, 337.0; calcd, 337.1.

Anal. Calcd for C$_{18}$H$_{16}$N$_4$OS: C, 64.26; H, 4.79; N, 16.65; Found: C, H, N.

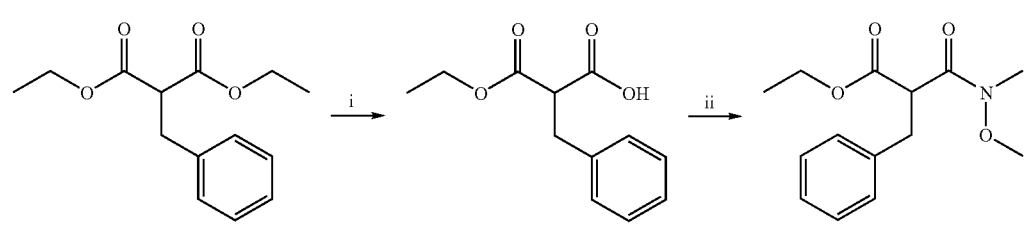

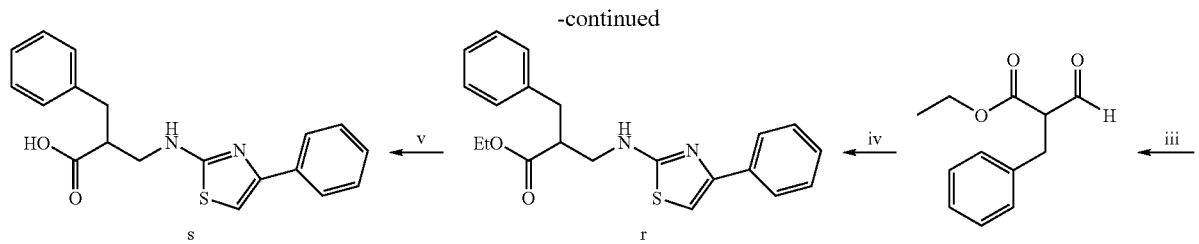

2-Benzyl-N-methoxy-N-methyl-malonamic acid ethyl ester[4] (22q)

To a solution of 2-Benzyl-malonic acid monoethyl ester (19n) (5 mmol, 1.11 g) in DCM, was added pyBOP (5.5 mmol, 2.86 g), DIEA (15 mmol, 2.7 ml) and N,O-dimethylhydroxylamine hydrochloride (5.5 mmol, 536 mg) and the reaction was stirred for 2 h. The organic layer was washed successively with a satured solution of $NaHCO_3$, 1N $KHSO_4$ solution, brine and dried over $Na_2SO_4$. It was concentrated in vacuo and purified by flash chromatography (AcOEt/Hexane: 3/7) to give a white solid (950 mg, 72%).

[4] Fehrentz, J. A.; Castro, B. An Efficient Synthesis of Optically Active α-(t-Butoxycarbonylamino)-aldehydes from α-Amino Acids; Synthesis, 1983, 1983(8), 676.

No NMR

MS (ESI) ($C_{14}H_{19}NO_4$) ([M+H]$^+$: found m/z, 266.1; calcd, 266.1.

Anal. Calcd for $C_{14}H_{19}NO_4$: C, 63.38; H, 7.22; N, 5.28; Found: C, H, N.

2-benzyl-3-oxo-propionic acid ethyl ester[3]

2-Benzyl-N-methoxy-N-methyl-malonamic acid ethyl ester (22q) (1 mmol, 265 mg) was dissolved in anhydrous THF at 0° C. LiAlH$_4$ (0.5 mmol, 19 mg) was added and the reaction was stirred for 15 min. The mixture was then hydrolyzed with a 1N KHSO$_4$ solution and the compound extracted with diethyl ether. The organic layer was washed successively with a satured solution of NaHCO$_3$, brine and dried over Na$_2$SO$_4$. It was concentrated in vacuo to give oil.

[5] Gutierrez C. D.; Bavetsias V.; McDonald E. TiCl(OiPr)$_3$ and NaBH(OAc)$_3$: an efficient reagent combination for the reductive amination of aldehydes by electron-deficient amines; Tet.Lett., 2005, 46, 3595-3597.

No Purification

MS (ESI) ($C_{12}H_{14}O_3$) ([M+H]$^+$: found m/z, 207.0; calcd, 207.1.

2-Benzyl-3-(4-phenyl-thiazol-2-ylamino)-propionic acid ethyl ester[5] (22r)

To a stirred solution of 2-amino-4-phenylthiazole (0.55 mmol, 97 mg) and 2-benzyl-3-oxo-propionic ethyl ester (0.5 mmol, 103 mg) in anhydrous CH$_2$Cl$_2$ (3 ml), was added TiCl(OiPr)$_3$ (1.1 mmol, 262 μl). The solution was stirred for 5 min before addition of freshly ground NaBH(OAc)$_3$ (2.5 mmol, 525 mg) and three drops of AcOH. The reaction mixture was stirred over night, then poured into saturated aqueous NaHCO$_3$ solution and extracted with CH$_2$Cl$_2$. The combined extracted were washed with brine, dried and concentrated in vacuo.

The product was purified by HPLC-MS, with a C$_8$ column, using gradient eluting solvents: 0.1% AcOH in acetonitrile 40%: 0.1% AcOH in water 60% to 0.1% AcOH in acetonitrile 70%: 0.1% AcOH in water 30% in 30 min.

MS (ESI) ($C_{21}H_{22}N_2O_2S$) ([M+H]$^+$: found m/z, 367.1; calcd, 366.1.

Anal. Calcd for $C_{21}H_{22}N_2O_2S$: C, 68.82; H, 6.05; N, 7.64; Found: C, H, N.

2-Benzyl-3-(4-phenyl-thiazol-2-ylamino)-propionic acid (22s)

To a solution of 2-Benzyl-3-(4-phenyl-thiazol-2-ylamino)-propionic ethyl ester (22r) (0.028 mmol, 10 mg) in EtOH (2 mL) and water (200 μL) is added KOH 1N solution (224 μL, 8 eq.). After 5 hours, the solution is neutralized with KHSO$_4$ 1N solution and lyophilized before purification.

The product was purified by HPLC-MS, with a C$_{18}$ column, using gradient eluting solvents: 0.1% AcOH in acetonitrile 30%: 0.1% AcOH in water 70% to 0.1% AcOH in acetonitrile 60%: 0.1% AcOH in water 40% in 30 min.

$^1$H NMR (300 MHz) in DMSO δ 7.74 (d, J=7.8 Hz, 2H), 7.34 (t, J=7.2 Hz, 5H), 7.25-7.16 (m, 3H), 6.99 (s, 1H), 3.29 (m, 2H), 2.91 (m, 1H), 2.72 (m, 2H).

MS (ESI) ($C_{21}H_{22}N_2O_2S$) ([M+H]$^+$: found m/z, 339.1.; calcd, 339.1.

Anal. Calcd for $C_{21}H_{22}N_2O_2S$: C, 68.82; H, 6.05; N, 7.64; Found: C, H, N.

What is claimed is:

1. A method of inhibiting preferentially cap-dependent protein synthesis in a breast cancer cell, a prostate cancer cell, a lung cancer cell, a pancreatic cancer cell or a colon cancer cell, comprising contacting said cell with a compound of the formula

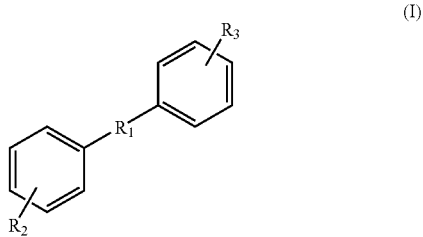
(I)

wherein $R_1$ is a hydrazone thiazole moiety of the structure

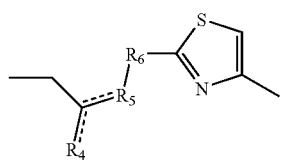
(II)

$R_2$ is hydrogen, hydroxyl or a nitro group present in one, two or three locations on the ring to which it is attached;
$R_3$ is a group individually present in one, two or three locations on the ring, wherein the group may be halo, hydrogen, conjugated or unconjugated aryl or heteroaryl, a alicyclic or polycyclic group, or $R_3$, taken with the ring to which it is attached, forms a conjugated ring structure;
$R_4$ is hydrogen, carboxyl, a lower alkyl ester or carbonyl, in which case the dotted bond is present;
$R_5$ is N, in which case the dotted bond is present, or NH; and
$R_6$ is NH.

2. The method of claim 1, wherein said compound is

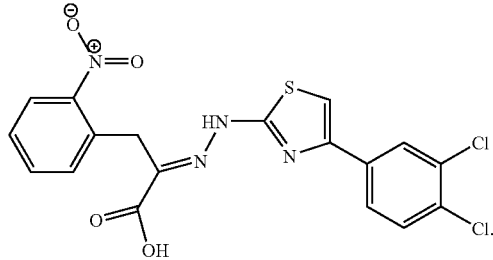

3. The method of claim 1, wherein said compound displaces a naturally-occurring 4E-BP-, or eIF4G-derived polypeptide, or a peptide containing the consensus YxxxxLΦ motif, where Φ stands for a hydrophobic residue and x is any amino acid.

4. The method of claim 1, wherein said compound inhibits binding between eIF4E and full-length eIF4G.

5. The method of claim 1, wherein said compound binds at or adjacent to V69, W73, Y76, Ser82, Ser83, L131, L135, or I138 of eIF4E.

6. A method of inhibiting proliferation of a breast cancer cell, a prostate cancer cell, a lung cancer cell, a pancreatic cancer cell or a colon cancer cell in an individual in need of such inhibition, comprising administering to a patient a pharmaceutical composition comprising a compound of the formula

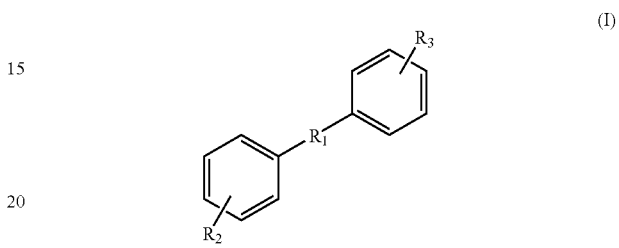
(I)

wherein $R_1$ is a hydrazone thiazole moiety of the structure

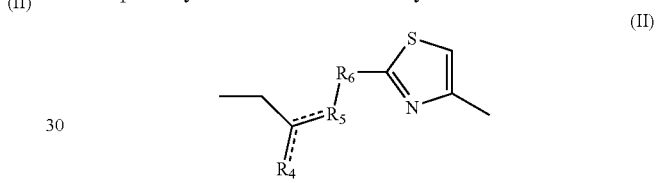
(II)

$R_2$ is hydrogen, hydroxyl or a nitro group present in one, two or three locations on the ring to which it is attached;
$R_3$ is a group individually present in one, two or three locations on the ring, wherein the group may be halo, hydrogen, conjugated or unconjugated aryl or heteroaryl, a alicyclic or polycyclic group, or $R_3$, taken with the ring to which it is attached, forms a conjugated ring structure;
$R_4$ is hydrogen, carboxyl, a lower alkyl ester or carbonyl, in which case the dotted bond is present;
$R_5$ is N, in which case the dotted bond is present, or NH; and
$R_6$ is NH.

7. The method of claim 6, wherein said compound is

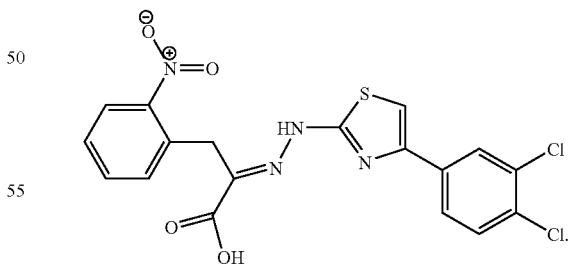

8. The method of claim 6, wherein said patient is identified as having a tumor cell which comprises an increased level of a cap-dependent translation factor compared to the level in a normal non-tumor cell.

9. The method of claim 8, wherein said patient is diagnosed as having a tumor cell which is characterized by an increased amount of a cap-dependent translation factor compared to the level in a normal non-tumor cell.

10. The method of claim 9, wherein said translation factor is eIF4E.

11. The method of claim 6, wherein said patient is identified as having a tumor.

12. The method of claim 6, wherein said patient is identified as having a lymphoma or a neuroblastoma.

13. The method of claim 6, wherein said patient is identified as having a bacterial or a viral infection.

14. A method of identifying a compound that preferentially inhibits proliferation of a breast cancer cell, a prostate cancer cell, a lung cancer cell, a pancreatic cancer cell or a colon cancer cell compared to a non cancerous cell of the same cell type, comprising contacting a cell with a compound of the formula

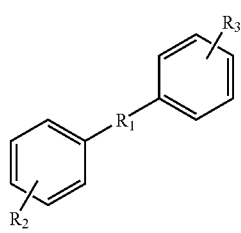
(I)

wherein

R₁ is a hydrazone thiazole moiety of the structure

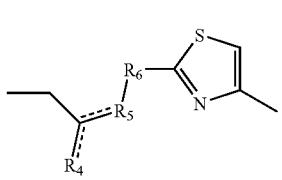
(II)

R₂ is hydrogen, hydroxyl or a nitro group present in one, two or three locations on the ring to which it is attached;

R₃ is a group individually present in one, two or three locations on the ring, wherein the group may be halo, hydrogen, conjugated or unconjugated aryl or heteroaryl, a alicyclic or polycyclic group, or R₃, taken with the ring to which it is attached, forms a conjugated ring structure;

R₄ is hydrogen, carboxyl, a lower alkyl ester or carbonyl, in which case the dotted bond is present;

R₅ is N, in which case the dotted bond is present, or NH; and

R₆ is NH and detecting a reduction in the level of proliferation of the cancer cell in the presence of said compound compared to a non-cancer cell in the presence of said compound.

15. The method of claim 14, wherein said tumor cell proliferation is at least 10% more compared to non-tumor cells.

16. The method of claim 14, wherein said compound is a 2-thiazolyl hydrazone.

17. A method of inhibiting proliferation of a breast cancer cell, a prostate cancer cell, a lung cancer cell, a pancreatic cancer cell or a colon cancer cell, comprising contacting said cell with an isolated, pure, stable E isomer compound of the formula

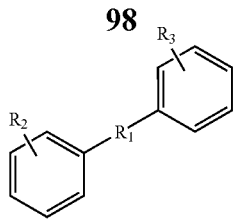

wherein

R1 is a hydrazone thiazole moiety of the structure

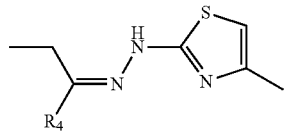

R2 is hydrogen, hydroxyl, CN, CF₃, CO₂H, SO₃H, PO₃H₂, SO₂R, SO₂NHR, SONH₂, CONH₂, CONHR, NHCOR, or a nitro group present in one, two or three locations on the ring to which it is attached and where R is an alkyl of 1-4 carbons or aryl;

R3 is a group individually present in one, two or three locations on the ring, wherein the group is halo, hydrogen, CN, CF₃, CO₂H, SO₃H, PO₃H₂, SO₂R, SO₂NHR, SONH₂, N=NR, CONH₂, CONHR, NHCOR, conjugated or unconjugated aryl or heteroaryl, a alicyclic, heterocyclic or polycyclic group, or a conjugated ring structure when taken with the ring to which R₃ is attached, where R is an alkyl of 1-4 carbons or aryl;

R4 is hydrogen, lower hydroxyalkyl, carboxyl, a lower alkyl ester, tetrazole, SO₃H or PO₃H₂; or a pharmaceutically acceptable salt thereof.

18. The method of claim 1 wherein the compound is an isolated, pure, stable E isomer compound of the formula

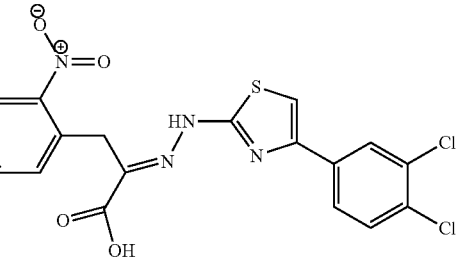

or a pharmaceutically acceptable salt thereof.

19. A method of inhibiting proliferation of a breast cancer cell, a prostate cancer cell, a lung cancer cell, a pancreatic cancer cell or a colon cancer cell, comprising contacting said cell with an isolated, pure, stable Z isomer compound of the formula

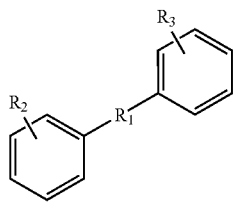

wherein

R1 is a hydrazone thiazole moiety of the structure

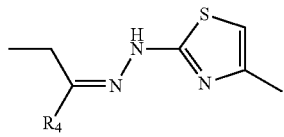

R2 is hydrogen, hydroxyl, CN, CF$_3$, CO$_2$H, SO$_3$H, PO$_3$H$_2$, SO$_2$R, SO$_2$NHR, SONH$_2$, CONH$_2$, CONHR, NHCOR, or a nitro group present in one, two or three locations on the ring to which it is attached and where R is an alkyl of 1-4 carbons or aryl;

R3 is a group individually present in one, two or three locations on the ring, wherein the group is halo, hydrogen, CN, CF$_3$, CO$_2$H, SO$_3$H, PO$_3$H$_2$, SO$_2$R, SO$_2$NHR, SONH$_2$, N=NR, CONH$_2$, CONHR, NHCOR, conjugated or unconjugated aryl or heteroaryl, a alicyclic, heterocyclic or polycyclic group, or a conjugated ring structure when taken with the ring to which R$_3$ is attached, where R is an alkyl of 1-4 carbons or aryl;

R4 is hydrogen, lower hydroxyalkyl, carboxyl, a lower alkyl ester, tetrazole, SO$_3$H or PO$_3$H$_2$; or a pharmaceutically acceptable salt thereof.

20. The method of claim 1 wherein the compound is an isolated, pure, stable Z isomer compound of the formula

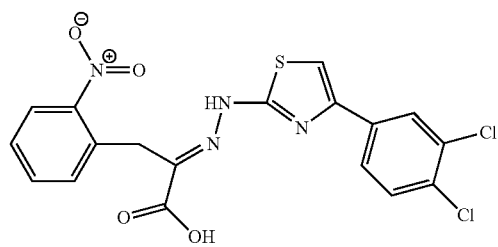

or a pharmaceutically acceptable salt thereof.

21. A method of inhibiting preferentially cap-dependent protein synthesis in a breast cancer cell, a prostate cancer cell, a lung cancer cell, a pancreatic cancer cell or a colon cancer cell, comprising contacting said cell with an isolated, pure, stable E isomer compound of the formula

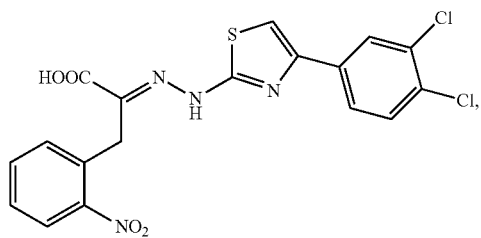

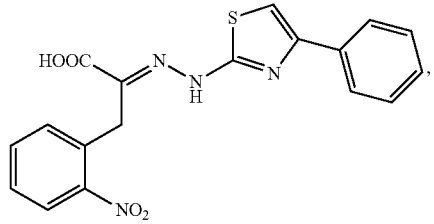

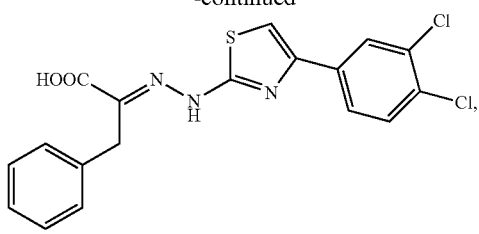

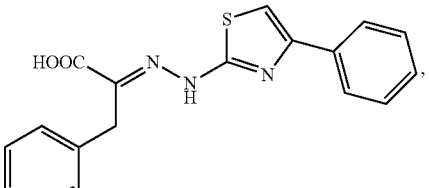

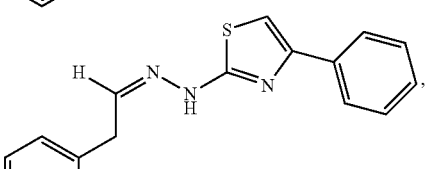

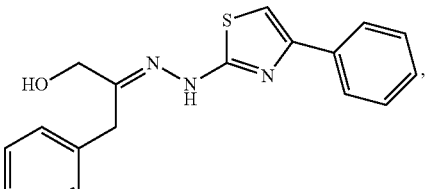

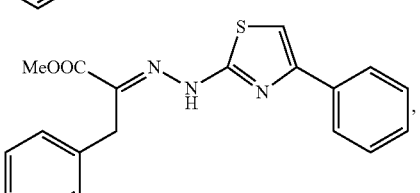

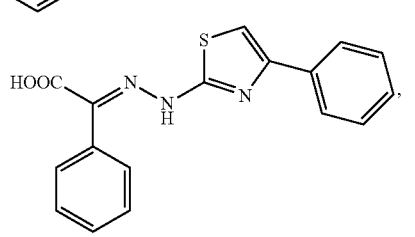

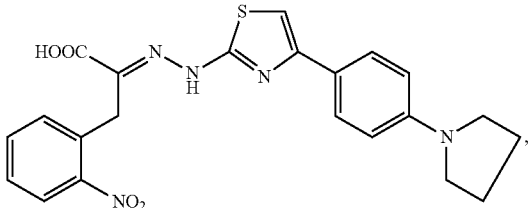

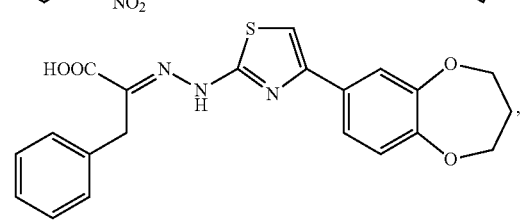

101

-continued

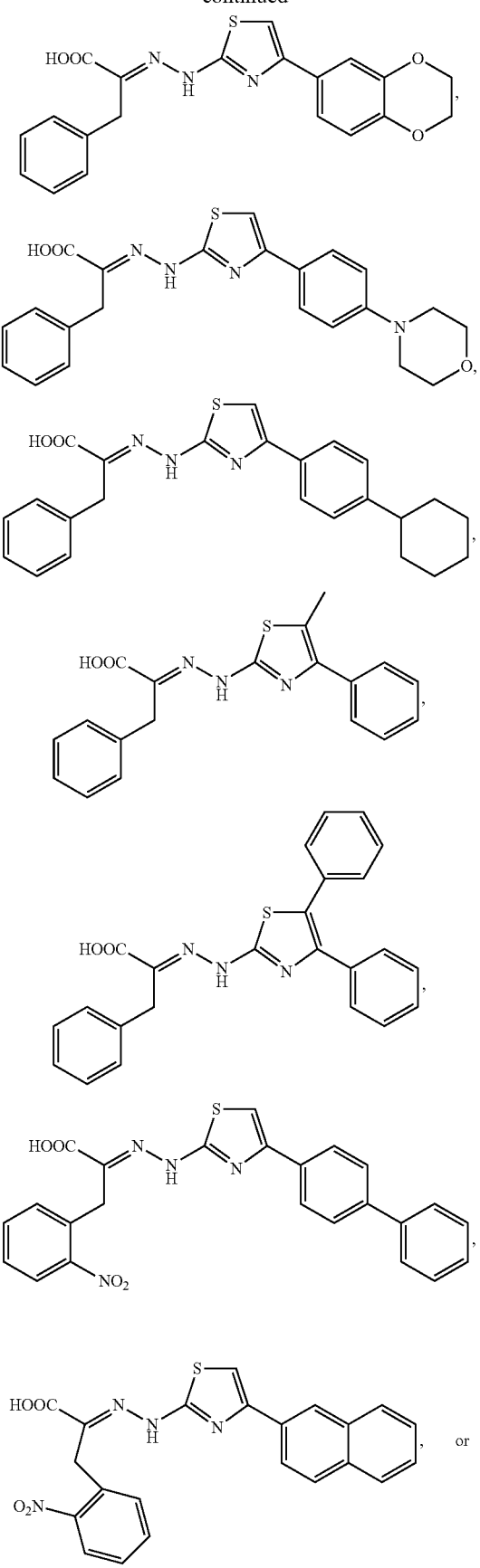

102

-continued

or a pharmaceutically acceptable salt thereof.

22. The method of claim 21 wherein the compound is in a pharmaceutical composition including a pharmaceutically acceptable carrier.

23. A method of inhibiting preferentially cap-dependent protein synthesis in a breast cancer cell, a prostate cancer cell, a lung cancer cell, a pancreatic cancer cell or a colon cancer cell, comprising contacting said cell with an-isolated, pure, stable Z isomer compound of the formula

103
-continued
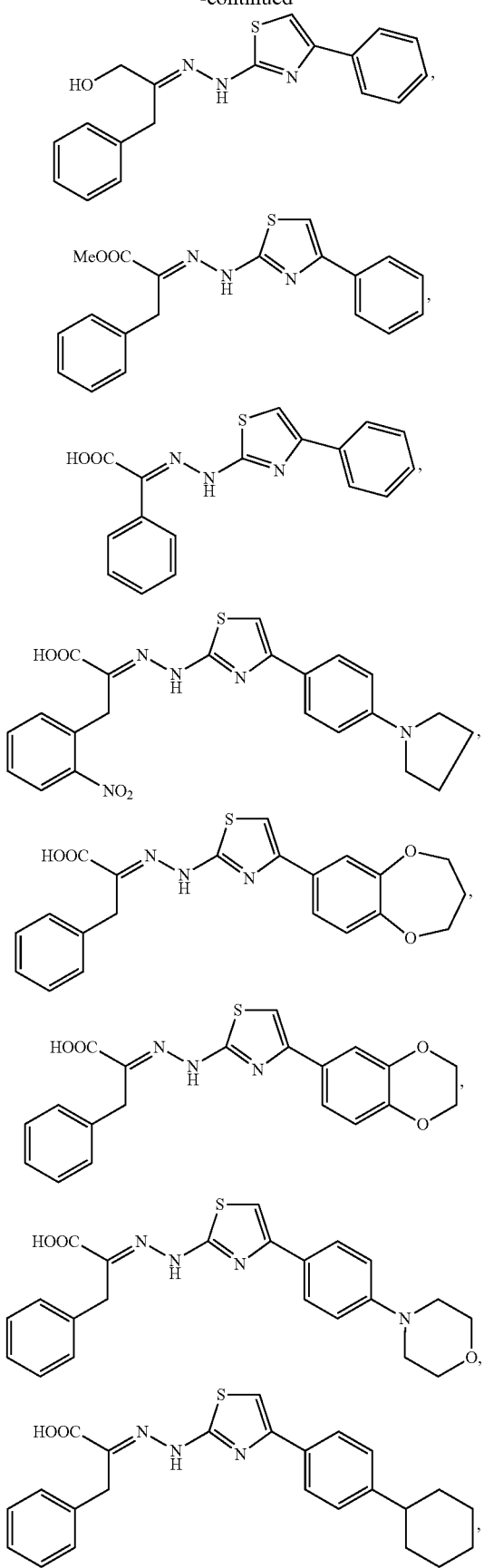
104
-continued
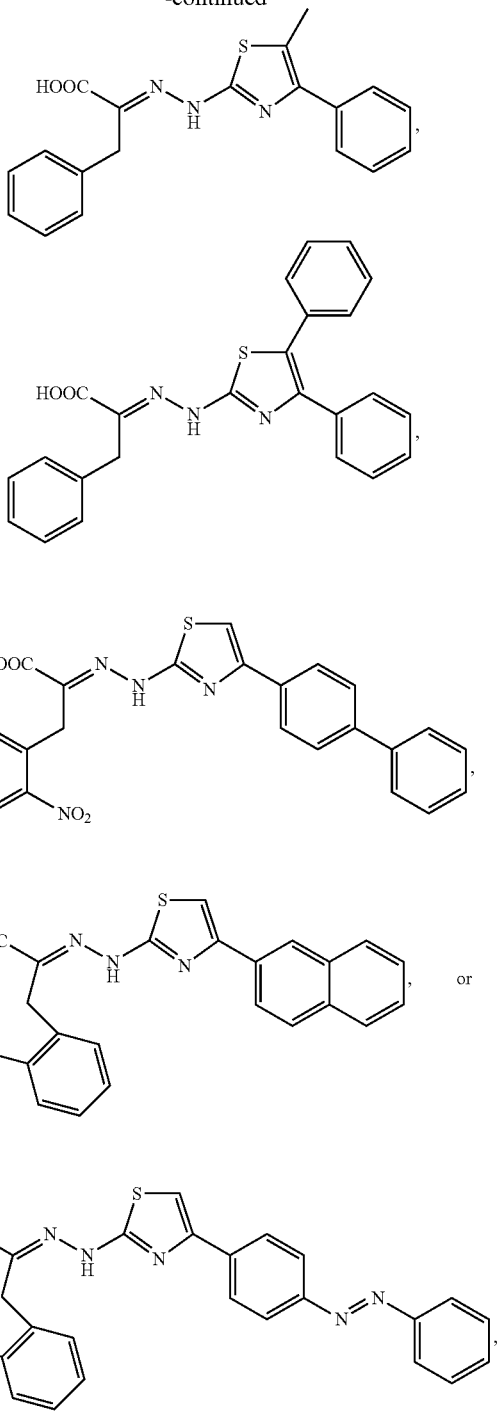
or a pharmaceutically acceptable salt thereof.
24. The method of claim 23 wherein the compound is in a pharmaceutical composition including a pharmaceutically acceptable carrier.
25. A method of inhibiting proliferation of a breast cancer cell, a prostate cancer cell, a lung cancer cell, a pancreatic cancer cell or a colon cancer cell, comprising contacting said cell with a compound of the formula

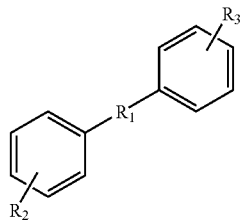 (I)

wherein
R₁ is a hydrazone thiazole moiety of the structure

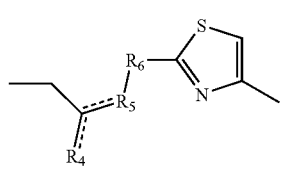 (II)

R₂ is hydrogen, hydroxyl or a nitro group present in one, two or three locations on the ring to which it is attached;
R₃ is a group individually present in one, two or three locations on the ring, wherein the group may be halo, hydrogen, conjugated or unconjugated aryl or heteroaryl, a alicyclic or polycyclic group, or R₃, taken with the ring to which it is attached, forms a conjugated ring structure, e.g., a naphthalene ring;
R₄ is hydrogen, carboxyl, a lower alkyl ester or carbonyl, in which case the dotted bond is present;
R₅ is N, in which case the dotted bond is present, NH; and
R₆ is NH.

26. The method of claim 25, wherein said compound is

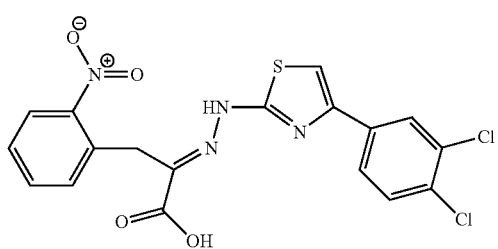

27. A method of inhibiting proliferation of a breast cancer cell, a prostate cancer cell, a lung cancer cell, a pancreatic cancer cell or a colon cancer cell, comprising contacting said cell with an isolated, pure, stable E isomer compound of the formula

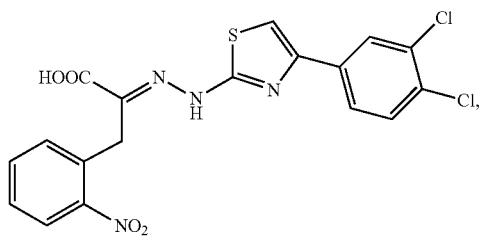

-continued

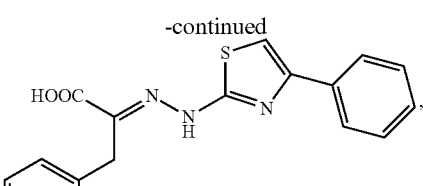

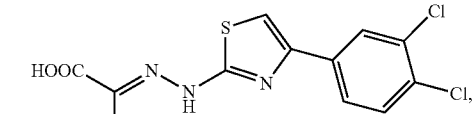

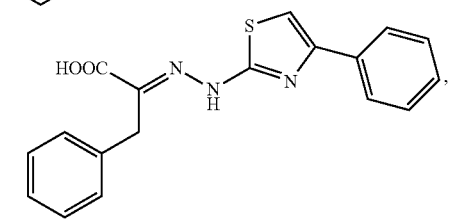

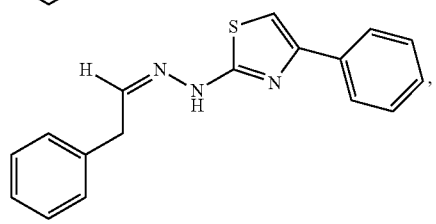

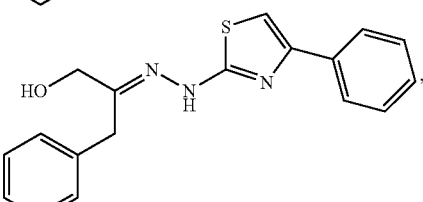

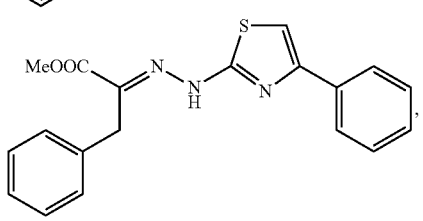

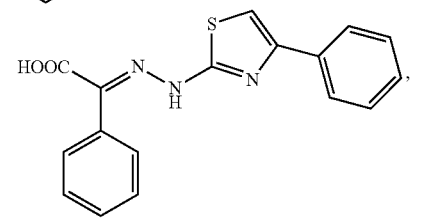

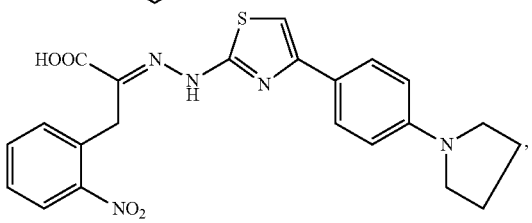

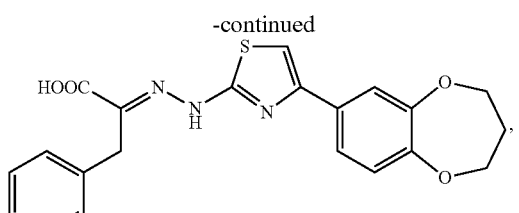

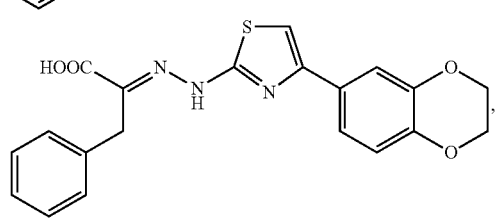

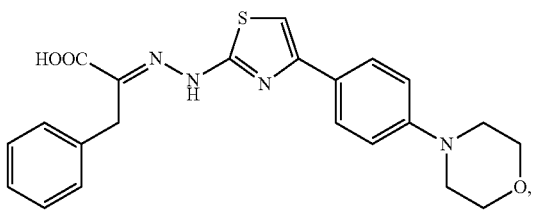

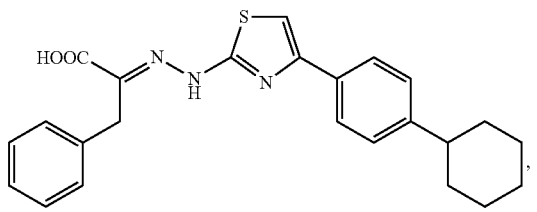

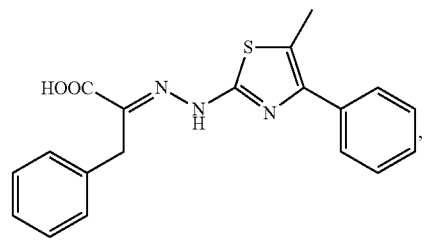

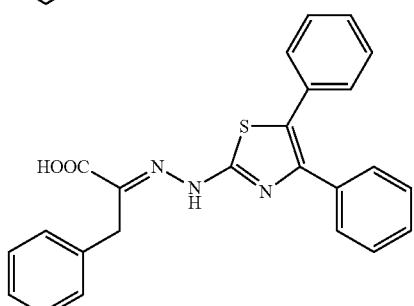

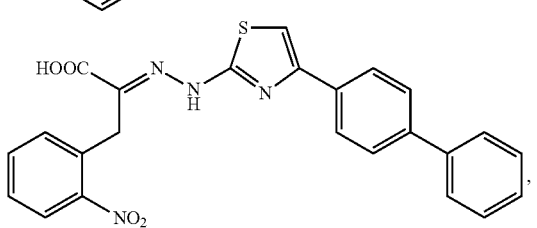

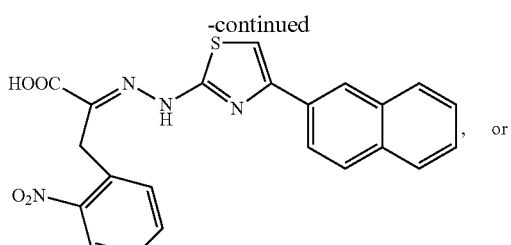, or

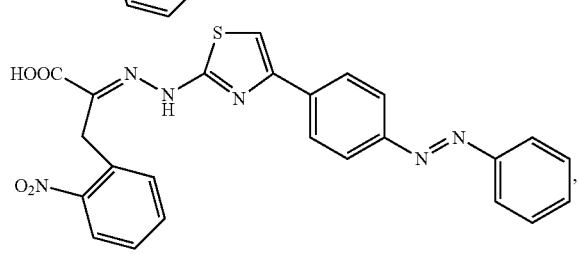

or a pharmaceutically acceptable salt thereof.

28. The method of claim 25 wherein the compound is in a pharmaceutical composition including a pharmaceutically acceptable carrier.

29. A method of inhibiting proliferation of a breast cancer cell, a prostate cancer cell, a lung cancer cell, a pancreatic cancer cell or a colon cancer cell, comprising contacting said cell with an-isolated, pure, stable Z isomer compound of the formula

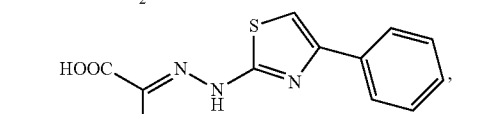

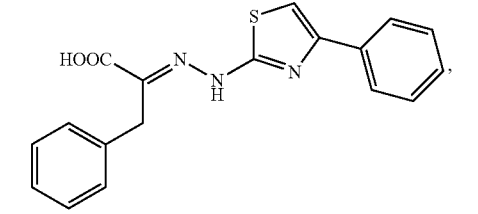

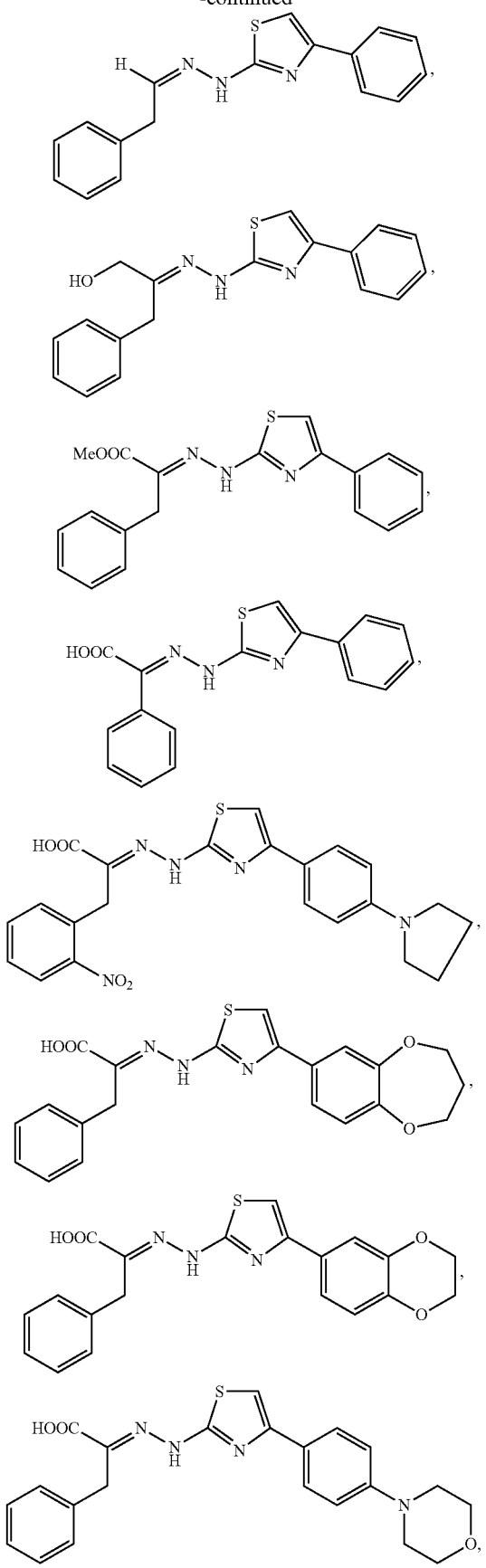
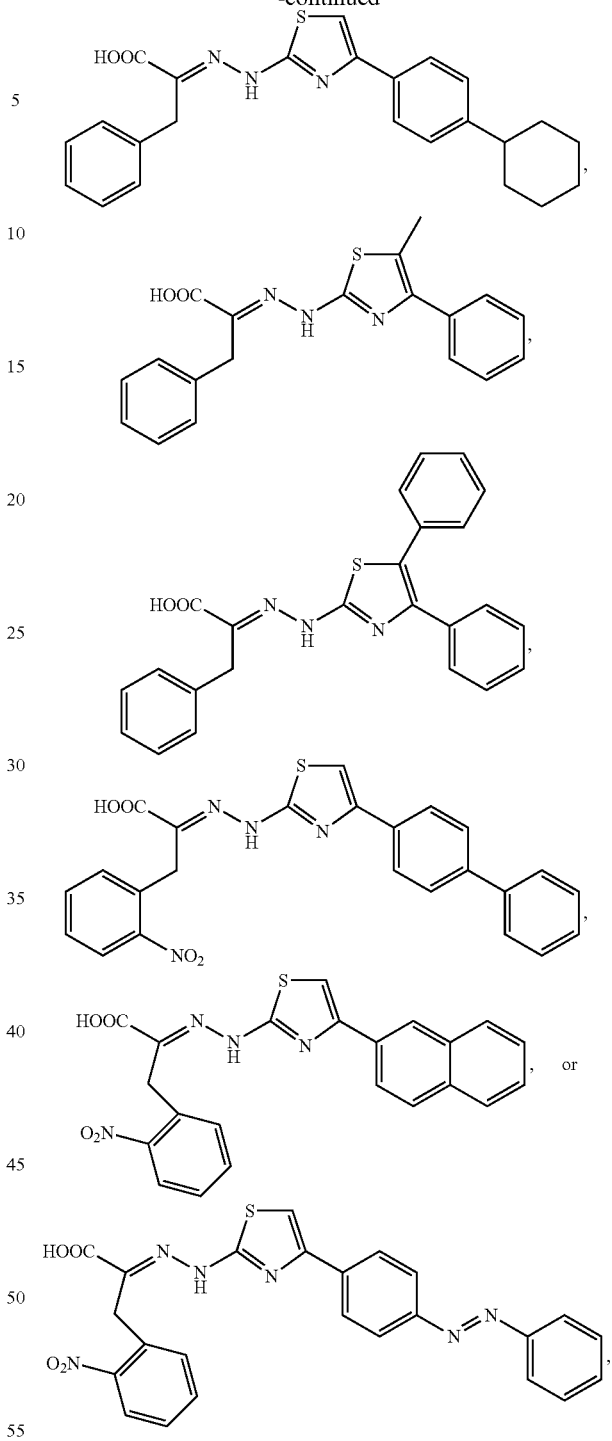
or a pharmaceutically acceptable salt thereof.
30. The method of claim 1 wherein the conjugated ring structure is a naphthalene ring.
31. The method of claim 1 wherein the lower alkyl ester is
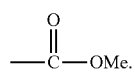

32. The method of claim 6 wherein the conjugated ring structure is a naphthalene ring.

33. The method of claim 6 wherein the lower alkyl ester is

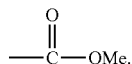

34. The method of claim 14 wherein the conjugated ring structure is a naphthalene ring.

35. The method of claim 14 wherein the lower alkyl ester is

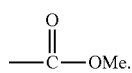

36. The method of claim 25 wherein the conjugated ring structure is a naphthalene ring.

37. The method of claim 25 wherein the lower alkyl ester is

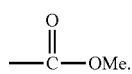

38. A method of inhibiting preferentially cap-dependent protein synthesis in a breast cancer cell, a prostate cancer cell, a lung cancer cell, a pancreatic cancer cell or a colon cancer cell, comprising contacting said cell with a compound of the formula

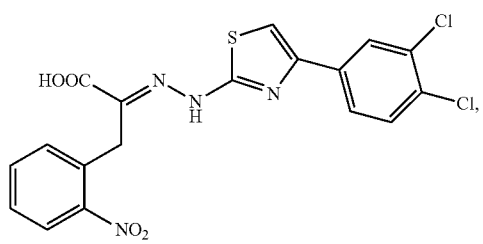

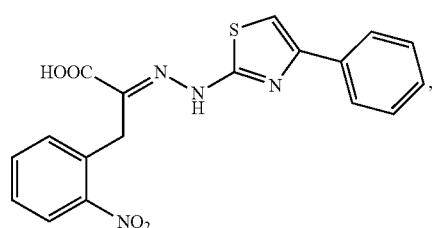

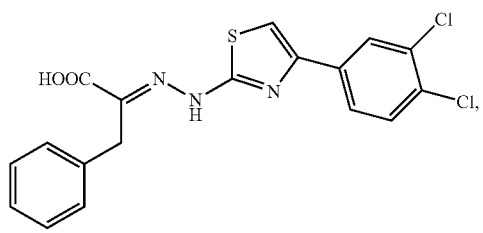

-continued

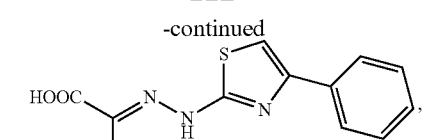

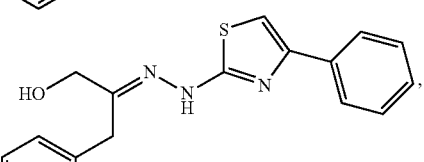

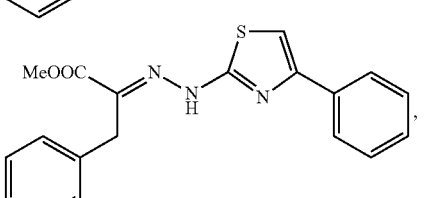

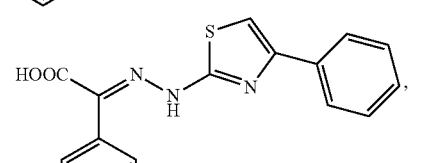

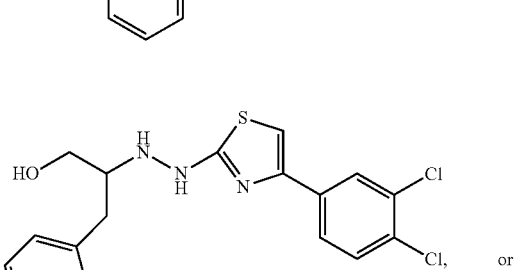

or a pharmaceutically acceptable salt thereof.

39. A method of inhibiting proliferation of a breast cancer cell, a prostate cancer cell, a lung cancer cell, a pancreatic cancer cell or a colon cancer cell in an individual in need of such inhibition, comprising administering to a patient a pharmaceutical composition comprising a compound of the formula
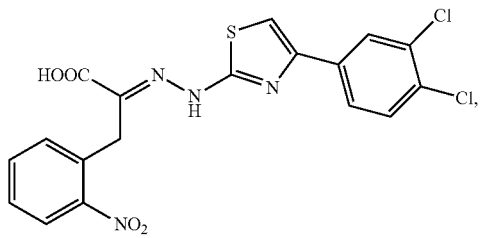
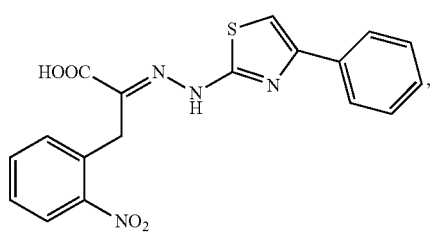
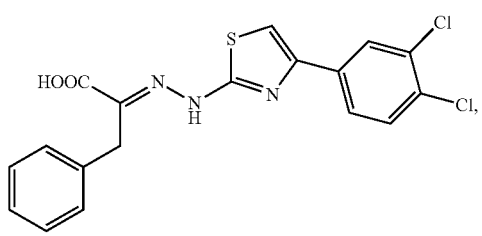
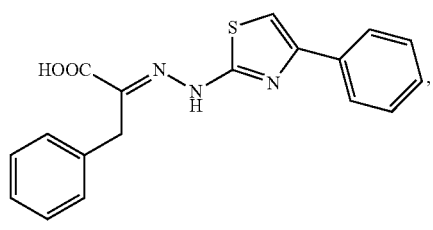
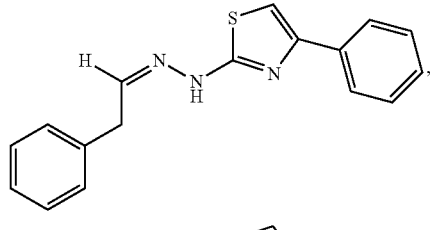
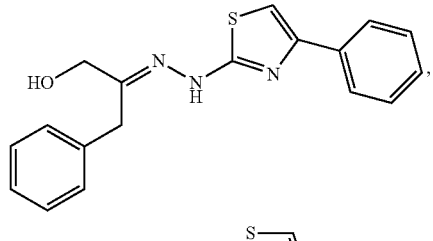
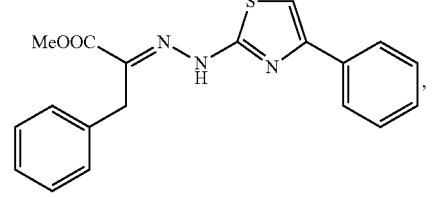
-continued
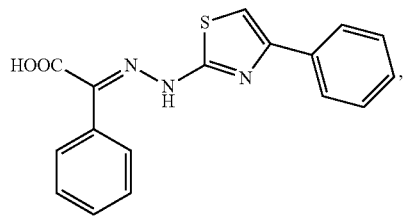
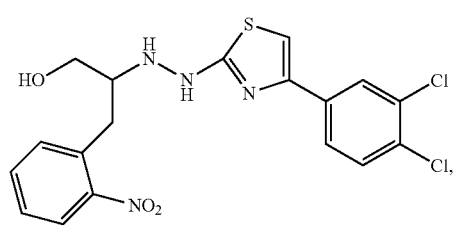, or
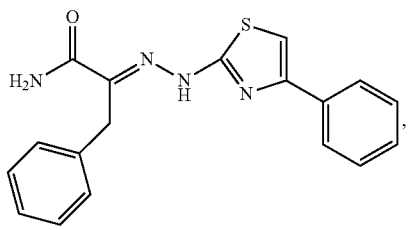,
or a pharmaceutically acceptable salt thereof.
40. A method of inhibiting proliferation of a breast cancer cell, a prostate cancer cell, a lung cancer cell, a pancreatic cancer cell or a colon cancer cell, comprising contacting said cell with a compound of the formula
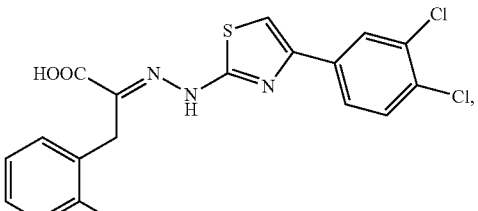
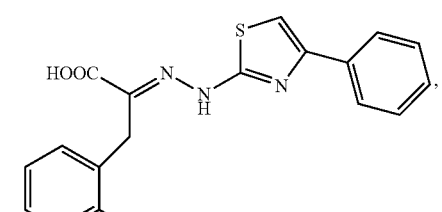,
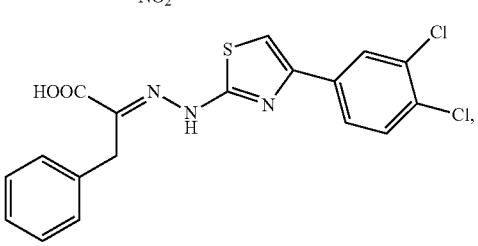,

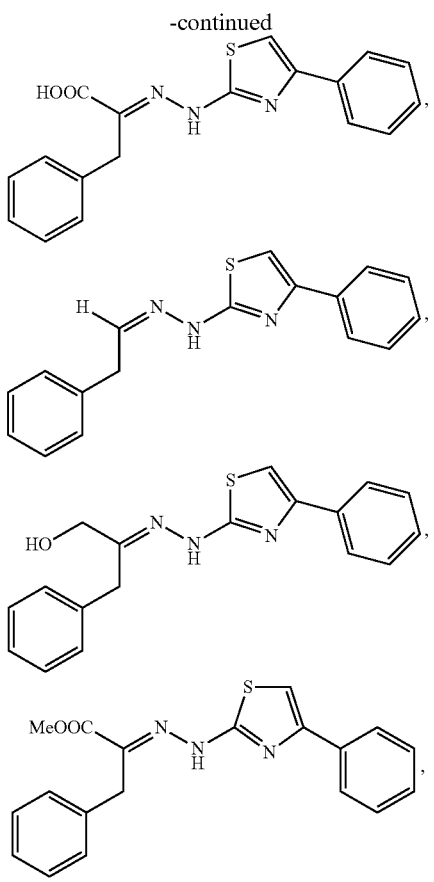
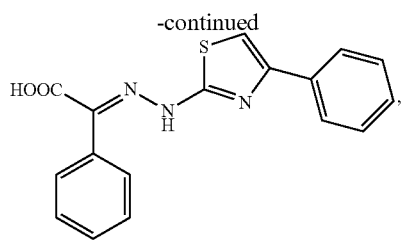
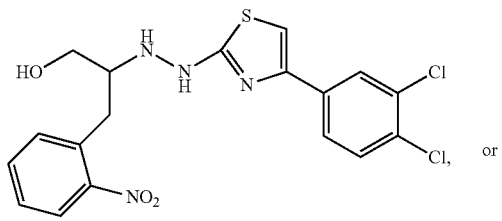
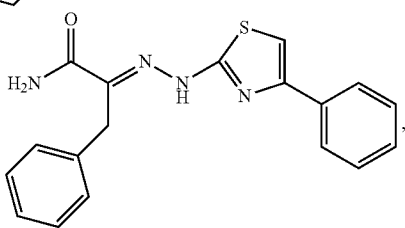
or a pharmaceutically acceptable salt thereof.
* * * * *

UNITED STATES PATENT AND TRADEMARK OFFICE
CERTIFICATE OF CORRECTION

Page 1 of 1

PATENT NO. : 8,257,931 B2
APPLICATION NO. : 11/795078
DATED : September 4, 2012
INVENTOR(S) : Wagner et al.

It is certified that error appears in the above-identified patent and that said Letters Patent is hereby corrected as shown below:

In the Specification

Under STATEMENT AS TO FEDERALLY SPONSORED RESEARCH Column 1, Line 13:
Please delete "This invention was funded in part by the U.S. Government under grant numbers U19-CA87427 and RO1-CA68262 awarded by the National Institutes of Health. The Government has certain rights in the invention."
And insert --This invention was made with government support under CA068262 and CA087427 awarded by the National Institutes of Health. The government has certain rights in the invention.--

Signed and Sealed this
Second Day of June, 2020

Andrei Iancu
*Director of the United States Patent and Trademark Office*